US011464747B2

(12) United States Patent
Wengner

(10) Patent No.: US 11,464,747 B2
(45) Date of Patent: Oct. 11, 2022

(54) ABUSE RESISTANT CAPSULE

(71) Applicant: R.P. Scherer Technologies, LLC, Las Vegas, NV (US)

(72) Inventor: Simone Wengner, Eberbach (DE)

(73) Assignee: R.P. Scherer Technologies, LLC, Las Vegas, NV (US)

( * ) Notice: Subject to any disclaimer, the term of this patent is extended or adjusted under 35 U.S.C. 154(b) by 57 days.

(21) Appl. No.: 16/572,148

(22) Filed: Sep. 16, 2019

(65) Prior Publication Data

US 2020/0009064 A1 Jan. 9, 2020

Related U.S. Application Data

(60) Continuation of application No. 15/257,274, filed on Sep. 6, 2016, now Pat. No. 10,744,097, which is a division of application No. 14/204,259, filed on Mar. 11, 2014, now Pat. No. 10,420,729.

(60) Provisional application No. 61/794,714, filed on Mar. 15, 2013.

(51) Int. Cl.
| | |
|---|---|
| *A61P 25/36* | (2006.01) |
| *A61K 9/48* | (2006.01) |
| *A61K 31/137* | (2006.01) |
| *A61K 31/485* | (2006.01) |
| *A61K 9/06* | (2006.01) |
| *A61K 9/08* | (2006.01) |
| *A61K 9/10* | (2006.01) |
| *A61K 47/14* | (2017.01) |
| *A61K 47/26* | (2006.01) |
| *A61K 47/36* | (2006.01) |
| *A61K 47/44* | (2017.01) |
| *A61K 31/196* | (2006.01) |

(52) U.S. Cl.
CPC .............. *A61K 9/4866* (2013.01); *A61K 9/06* (2013.01); *A61K 9/08* (2013.01); *A61K 9/10* (2013.01); *A61K 9/4825* (2013.01); *A61K 9/4858* (2013.01); *A61K 9/4875* (2013.01); *A61K 9/4891* (2013.01); *A61K 31/137* (2013.01); *A61K 31/196* (2013.01); *A61K 31/485* (2013.01); *A61K 47/14* (2013.01); *A61K 47/26* (2013.01); *A61K 47/36* (2013.01); *A61K 47/44* (2013.01); *A61K 9/485* (2013.01)

(58) Field of Classification Search
None
See application file for complete search history.

(56) References Cited

U.S. PATENT DOCUMENTS

| | | | |
|---|---|---|---|
| 6,340,471 B1 | 1/2002 | Kershman et al. | |
| 6,509,040 B1 | 1/2003 | Murray et al. | |
| 6,541,025 B1 | 4/2003 | Kershman et al. | |
| 7,230,005 B2 | 6/2007 | Shafer et al. | |
| 7,399,488 B2 | 7/2008 | Hirsh et al. | |
| 7,510,726 B2 | 3/2009 | Kumar et al. | |
| 7,776,314 B2 | 8/2010 | Bartholomaus et al. | |
| 7,842,307 B2 | 11/2010 | Oshlack et al. | |
| 8,202,542 B1 | 6/2012 | Mehta et al. | |
| 8,252,326 B2 | 8/2012 | Lin | |
| 8,273,798 B2 | 9/2012 | Bausch et al. | |
| 8,333,989 B2 | 12/2012 | Sukuru | |
| 8,420,700 B1 | 4/2013 | Bausch et al. | |
| 9,622,972 B2 | 4/2017 | Bredenberg et al. | |
| 10,420,729 B2 | 9/2019 | Wengner | |
| 2003/0059397 A1 | 3/2003 | Hughes | |
| 2005/0152843 A1 | 7/2005 | Bartholomaus et al. | |
| 2005/0163856 A1 | 7/2005 | Maloney et al. | |
| 2005/0191244 A1 | 9/2005 | Bartholomaus et al. | |
| 2005/0271594 A1 | 12/2005 | Groenewoud | |
| 2007/0092560 A1 | 4/2007 | Sukuru | |
| 2007/0215511 A1 | 9/2007 | Mehta et al. | |
| 2008/0027011 A1 | 1/2008 | Nached et al. | |
| 2009/0082466 A1 | 3/2009 | Babul | |
| 2009/0123386 A1 | 5/2009 | Young | |
| 2009/0215808 A1 | 8/2009 | Yum et al. | |
| 2009/0232887 A1 | 9/2009 | Odidi et al. | |
| 2010/0099696 A1 | 4/2010 | Soscia et al. | |
| 2010/0203124 A1 | 8/2010 | Modliszewski et al. | |

(Continued)

FOREIGN PATENT DOCUMENTS

| | | | |
|---|---|---|---|
| CN | 101400343 A | 4/2009 | |
| CN | 101484135 A | 7/2009 | |

(Continued)

OTHER PUBLICATIONS

"EVONIK Aerosil® fumed silica," accessed from the Internet at https://www.aerosil.com/product/aerosil/en/Pages/-default.aspx on May 15, 2017 (Year: 2017).*
Search Report and Written Opinion for Brazilian application No. BR112015022583; dated Nov. 21, 2019 (6 pages).
Communication pursuant to Article 94(3) EPC for European application No. 18190832.8; dated Dec. 11, 2019 (5 pages).
Results of Substantive Examination for Mexican application No. MX/a/2015/012742; dated Oct. 30, 2019 (2 pages).

(Continued)

*Primary Examiner* — David J Blanchard
*Assistant Examiner* — Daniel F Coughlin
(74) *Attorney, Agent, or Firm* — Mendelsohn Dunleavy, P.C.

(57) ABSTRACT

The present invention is directed to an immediate release and extended release capsule or capsule fill which mitigates the abuse of abuse-susceptible active pharmaceutical ingredients by direct intravenous injection. The fill comprises a parenteral abuse resistant liquid formulation which when mixed with water and heated, results in a turbid, viscous or bubbling mixture that is not injectable with a standard insulin syringe. The abuse-susceptible active pharmaceutical ingredient is selected from the group consisting of opiates, opioids, tranquilizers, stimulants and narcotics.

15 Claims, No Drawings

(56) References Cited

U.S. PATENT DOCUMENTS

| | | |
|---|---|---|
| 2010/0249045 A1 | 9/2010 | Babul |
| 2010/0260833 A1 | 10/2010 | Bartholomaus et al. |
| 2011/0092583 A1 | 4/2011 | Murty et al. |
| 2011/0207761 A1 | 8/2011 | Losev et al. |
| 2012/0015031 A1 | 1/2012 | Sesha |
| 2012/0148672 A1 | 6/2012 | Mehta et al. |
| 2012/0171277 A1 | 7/2012 | Royds |
| 2013/0287843 A1 | 10/2013 | Young |

FOREIGN PATENT DOCUMENTS

| | | |
|---|---|---|
| CN | 102026618 A | 4/2011 |
| CN | 102341096 A | 2/2012 |
| EP | 1611880 B1 | 11/2008 |
| GB | 2238478 A | 6/1991 |
| JP | 2003113119 A | 4/2003 |
| JP | 2005500364 A | 1/2005 |
| JP | 2009530298 A | 8/2009 |
| JP | 2009-536927 A | 10/2009 |
| JP | 2012140393 A | 7/2012 |
| JP | 2016-510792 A | 4/2016 |
| WO | 03013476 A1 | 2/2003 |
| WO | WO2007109104 A2 | 9/2007 |
| WO | 2007131357 A1 | 11/2007 |
| WO | WO2009114118 A2 | 9/2009 |
| WO | WO2010044842 A1 | 4/2010 |
| WO | WO2010063909 A2 | 6/2010 |
| WO | WO2010066034 A1 | 6/2010 |
| WO | WO2010099508 A1 | 9/2010 |
| WO | WO2010105672 A1 | 9/2010 |
| WO | WO2013003845 A1 | 1/2013 |
| WO | 2014140231 A1 | 9/2014 |

OTHER PUBLICATIONS

Final Rejection for U.S. Appl. No. 15/257,74; dated Dec. 6, 2019; (18 pages).
Notice of Reasons for Refusal for corresponding Japanese Application No. 2018-159092; dated Sep. 17, 2019 (12 pages).
"Examiners Opinion" and Search Report for corresponding Colombian Application No. NC2019/0000388; dated Aug. 29, 2019 (8 pages).
Examination Report for corresponding Australian application No. 2019264648; dated Aug. 11, 2020 (4 pages).
Examiner's Opinion from corresponding Colombian application No. NC2019/0000388; dated Feb. 28, 2020 (15 pages).
"EVONIK Aerosil® fumed silica," accessed from the Internet at https://www.aerosil.com/product/aerosil/en/Pages/default.aspx on May 15, 2017.
Result of Substantive Examination for Mexican Patent Application No. MX2015/012742; dated May 20, 2019.
Australian Examination Report; dated Mar. 15, 2019 for AU Application No. 2018214110.
European Search Report; dated Jan. 24, 2019 for EP Application No. 18190832.8.
Chinese Office Action; dated Nov. 14, 2018 for CN Application No. 201480014915.6.
Chinese Office Action; dated Apr. 24, 2018 for CN Application No. 201480014915.6.
Japanese Final Notification of Reasons for Refusal; dated Feb. 13, 2018 for JP Application No. 2015-562169.
Australian Examination Report; dated Dec. 22, 2017 for AU Application No. 2014230481.
Japanese Office Action; dated Sep. 12, 2017 for JP Application No. 2015-562169.
Colombian Office Action; dated Aug. 24, 2017 for CO Application No. 15-218.009.
Chinese Office Action; dated Jul. 31, 2017 for CN Application No. 201480014915.6.
European Office Action: dated Mar. 24, 2017 for EP Application No. 14711201.5.
Opposition Report; dated Feb. 6, 2017 for CO Application No. 15-218.009 (concise explanation of oppositions).
Laboratorio Franco Colombiano Lafrancol S.A.S. Opposition; Received Jan. 18, 2017 in opposition to CO Application 15-218.009.
Tecnoquimicas S.A. Opposition and Supplement; Received Jan. 18, 2017 in opposition to CO Application 15-218.009.
Laboratorios Legrand SA Opposition; Received Jan. 18, 2017 in opposition to CO Application 15-218.009.
Park, K., PhD, "Solid Dosage Forms: Capsules," Chapter 3, Lecture, retrieved from www.kinam.com/Lectures/363/3.Capsules%20Text.pdf on May 8, 2014.
International Search Report and Written Opinion; dated Jun. 26, 2014 for related PCT Application No. PCT/EP2014/055045.
LABRASOL®, as accessed from the Internet on Aug. 3, 2017 from <https://www.gattefosse.com/labrasol>.
First Office Action for corresponding Chinese application No. 201910975199.2; dated Mar. 30, 2021 (33 pages).
Extended European Search Report for corresponding European application No. 20216392.9; dated Mar. 18, 2021 (10 pages).
Examination Report for corresponding Mexican application No. MX/a/2020/009411; dated Feb. 23, 2021 (5 pages).
Office Action for corresponding Argentinian application No. 20140101047; dated Jan. 26, 2022 (13 pages) Machine Translation.
Notice of Reasons for Refusal for corresponding Japanese application No. 2020-219732; dated Feb. 15, 2022 (8 pages) Machine Translation.
Third Office Action for corresponding Chinese application No. 201910975199.2; dated Mar. 15, 2022 (10 pages).
Second Office Action for corresponding Chinese application No. 201910975199.2; dated Oct. 19, 2021 (25 pages).
Decision of Refusal for corresponding Japanese application No. 2020-219732; dated Aug. 9, 2022 (4 pages) Machine Translation.

* cited by examiner

ABUSE RESISTANT CAPSULE

CONTINUITY DATA

This application is a continuation of U.S. patent application Ser. No. 15/257,274 filed on Sep. 6, 2016, which in turn, is a divisional of U.S. patent application Ser. No. 14/204,259, filed on Mar. 11, 2014, now U.S. Pat. No. 10,420,729, issued on Sep. 24, 2019, which, in turn, claims the benefit of U.S. provisional application No. 61/794,714, field on Mar. 15, 2013, the disclosures of which each hereby incorporated by reference in their entirety.

FIELD OF THE INVENTION

The present invention relates generally to an immediate release or an extended release capsule formulation that is resistant to parenteral abuse of abuse-susceptible active pharmaceutical ingredients such as opiates, opioids, tranquilizers, stimulants, and narcotics.

DESCRIPTION OF THE RELATED TECHNOLOGY

Many active pharmaceutical ingredients, in addition to having an excellent activity in their appropriate application, also have potential for abuse, i.e. they can be used by an abuser to bring about effects other than those intended. For example, opioid analgesics, which are highly active in combating severe to very severe pain, are frequently used by abusers to induce a state of narcosis or euphoria. Typically, a particular dose of an opioid analgesic is more potent when administered parenterally as compared to the same dose administered orally. One popular mode of abuse of oral opioid formulations involves the extraction of the opioid from the dosage form, and the subsequent injection of the opioid (using any suitable vehicle for injection such as an insulin syringe) in order to achieve a "high".

This abuse problem is well known to the pharmaceutical and medical industries, and various methods of obviating such abuse have been devised.

U.S. Pat. No. 7,842,307 (to Purdue Pharma L.P.) discloses oral dosage forms comprising a therapeutically effective amount of an opioid analgesic, an opioid antagonist and one or more pharmaceutically acceptable excipients. The dosage form further includes a gelling agent in an effective amount to impart a viscosity unsuitable for administration selected from the group consisting of parenteral and nasal administration to a solubilized mixture formed when the dosage form is crushed and mixed with from about 0.5 to about 10 mL of an aqueous liquid. The active pharmaceutical ingredient that is suspended in high viscosity solutions is unsuitable for abuse via intravenous injections.

UK Patent Application GB 2 238 478 A (to Farmitalia Carlo Erba Ltd and RP Scherer Limited) is directed to a pharmaceutical unit dosage form which comprises a soft gelatin capsule shell or a two-piece hard gelatin capsule filled with a benzodiazepine (preferably temazepam) in a gel comprising at least 63% of polyethylene glycol 600, at least 4% by weight of polyethylene glycol 4000 or 6000 and at least 21% by weight of an intermediate polyethylene glycol. This purports to solve the abuse problem by using a formulation that is too viscous to be expelled from a syringe.

U.S. Pat. No. 7,230,005 (to Controlled Chemicals, Inc.) is directed to solving the abuse problem discussed above by converting the active pharmaceutical ingredient to a poorly absorbed ester pro drug or other prodrug derivative prior to formulation. Mechanical processing of tablet or caplets containing the prodrug does not release the active API. The tablets and capsule beads containing prodrugs or other drugs can be formulated with a sufficient amount of a thickening agent to impede inappropriate intravenous administration of formulations that are not indicated for these modes of administration.

WO 2010/044842 A1 (to Univ. Tennessee) is directed to solving the abuse problem by including an effective amount of embolizing agent (i.e., coagulating agent) which causes the production of a solid or semi-solid embolus or blockage after tampering. Suitable examples of embolic agents are thrombin, cellulose diacetate polymer, albumin, gelatin, fibrinogen, lactoglobulin, immunoglobulin, actin, acrylamide, polyacrylonitrile, polyurethane, polyvinylacetate, nitrocellulose and copolymers of urethane/carbonate and copolymers of styrene/maleic acid and pH sensitive polymers consisting of copolymers of methyl and butyl methacrylate and dimethylaminoethylmethacrylates.

U.S. Pat. No. 8,202,542 (to TrisPharma) discloses a modified release tablet formulation of an opioid drug bound to an ion exchange resin, coated with a hybrid coating comprising a barrier coating containing a polyvinyl acetate polymer and a plasticizer and an enteric polymer mixed therewith.

WO 2013/003845 A1 (to Neos Therapeutics, LP) is directed to oral drug dosage forms designed to reduce the abuse potential of an oral dosage form of an opioid analgesic. The oral drug dosage form comprises a first population of drug-resin complex particles comprising an analgesically effective amount of an opioid drug coated with a water-permeable diffusion barrier coating; and a second population of ion exchange-resin complex particles comprising an aversive agent coated with a polymer coating sufficient to substantially prevent release of the aversive agent under normal use conditions. The abuse problem is addressed by using two different particles within the liquid or solid dosage form.

European Patent No. 1 611 880 B1 (to Altergon S.A.) is directed to overcoming the abuse problem by providing pharmaceutical compositions of drugs known as replacement narcotics used in drug addiction therapy, such as methadone and/or its salts, preferably its hydrochloride, in a uniform soft-gel matrix to be taken orally without chewing. The uniform matrix has the shape and size of a pill or capsule of a certain formulation. The formulation is entirely gelatinized, i.e., uniformly incorporated within the soft-gel matrix.

US 2010/0099696 A1, is directed to an oral dosage formulation containing a therapeutically effective amount of a drug susceptible to abuse and an effective amount of an embolizing agent which causes the production of a solid or semi-solid embolus or blockage after tampering. The embolizing agent is a pH dependent polymer such as methacrylate, cellulose based polymer, and phthalate.

U.S. Pat. No. 7,776,314 (to Grunenthal) relates to a solid administration form, protected from parenteral abuse and containing at least one viscosity-increasing agent in addition to one or more active substances that have parenteral abuse potential. The agent forms, when a necessary minimum amount of an aqueous liquid is added, on the basis of an extract obtained from the administration form, a preferably injectable gel that remains visually distinct when introduced into another quantity of an aqueous liquid.

U.S. Pat. No. 7,510,726 (to Acura Pharmaceuticals, Inc.) relates to an abuse deterrent dosage form of opioids, wherein an analgesically effective amount of opioid analgesic is combined with a polymer to form a matrix. The formation of a high-viscosity gel is a result of exposing the solid dosage form to water.

U.S. Pat. No. 7,399,488 (to Collegium Pharmaceutical, Inc.) is directed to an abuse-deterrent pharmaceutical composition wherein a drug is modified to increase its lipophilicity. In preferred embodiments the modified drug is homogeneously dispersed within microparticles composed of a material that is either slowly soluble or not soluble in water. In some embodiments the drug containing microparticles or drug particles are water insoluble, but enzymatically degradable by enzymes present in the human gastrointestinal tract.

U.S. Patent Application Publication No. 2009/0215808 (to Durect Corp.) is directed to oral pharmaceutical composition that is abuse-resistant, and its use to deliver the active pharmaceutical ingredient.

US 2010/0249045 (to Theraquest Biosciences, Inc.) is directed to abuse resistant pharmaceutical compositions of opioids and extended release pharmaceutical compositions. All of the formulations appear to be for caplets.

WO 2010/105672 A1 (to EvonikRöhm GmbH) relates to a controlled release pharmaceutical composition, comprising a core comprising a pharmaceutical active ingredient, whereby the core is coated by an ethanol resistance conferring coating layer which has the effect of conferring the release profile of the pharmaceutical active ingredient to be resistant against the influence of ethanol. The carious coating techniques and formulations related thereto are taught.

WO 2010/066034 A1 (to Paladin Labs Inc.) is directed to novel narcotic formulations having a decreased injection abuse potential. An oral pharmaceutical formulation is provided that makes the extraction of the active pharmaceutical ingredient more difficult, in particular in aqueous and alcohol solvents, and therefore prevents, or at least significantly reduces, the potential for abuse, while purportedly allowing the pharmaceutical formulation to release the active pharmaceutical ingredient in the gastrointestinal tract upon ingestion to allow for the desired pharmacological effect. The drug formulation is in form of a tablet, comprising a salt of the abuse-susceptible active pharmaceutical ingredient, and an alkalizing agent for reducing the solubility of the drug in no-acidic solutions.

The abuse problem that the present invention mitigates, is based on illicitly obtaining the abuse-susceptible active pharmaceutical ingredient from a capsule that comprises a fill which in turn comprises the abuse-susceptible active pharmaceutical ingredient.

Drug users are able to recover the fill and/or treat the fill to obtain the active pharmaceutical ingredient therefrom. Such treatment includes solubilizing the fill with a small amount water, such as about 5 mL of water per 1 capsule. This mixture is then heated, optionally boiled, and filtered through a filter, such as a cigarette filter, into a hypodermic syringe. Such a syringe may be an insulin syringe equipped with a needle. The syringes that are used for insulin injections typically comprise 20 to 31 gauge needles. Typically, due to viscosity challenges, the illicit drug user will select a relatively thicker gauge needles, such as a 20 gauge needle (about 0.91 mm outer diameter, 0.60 mm inner diameter).

SUMMARY OF THE INVENTION

The present invention is directed to the development of an immediate release capsule formulation or an extended release capsule formulation. More specifically, the invention is directed to an immediate release capsule formulation, which mitigates the abuse of abuse-susceptible active pharmaceutical ingredients by direct intravenous injection.

One of the aspects of the present invention is to provide for a capsule comprising a tamper resistant fill formulation which when mixed with water and heated, results in a turbid, bubbling mixture that is not injectable with a standard insulin syringe.

There are several different characteristics that may make the fill formulation abuse resistant. One characteristic that makes the fill formulation abuse resistant is that the viscosity increases upon heating or boiling of the formulation in water. The viscosity of the mixture is increased to such a level that it is difficult or impossible to fill the insulin syringe with the mixture. Under one embodiment of the invention, the viscosity of the heated mixture increases to a level that it may not be deliverable even through needles with the largest diameters commonly used in delivery of insulin.

The second characteristic that makes a fill formulation abuse resistant is that upon heating or boiling the mixture of the fill with water, bubbles occur in the mixture. The presence of such bubbles makes it more difficult to draw the mixture into the syringe. The bubbles also have a deterrent effect in that intravenous drug users tend to avoid introduction of air bubbles into their bloodstream due to their fear of air embolism.

Although there are many combinations of the fill components that may work well to deliver the active pharmaceutical ingredient, it was surprising that only certain combinations of the components result in parenteral abuse resistant fill formulations.

Generally, the present invention is directed to a parenteral abuse resistant liquid suitable for encapsulation in a capsule.

In the first aspect of the present invention, the parenteral abuse resistant liquid suitable for encapsulation in a capsule comprises: (a) an abuse-susceptible active pharmaceutical ingredient selected from the group consisting of opiates, opioids, tranquilizers, stimulants and narcotics; (b) a viscosity enhancer or an ion exchange resin; and (c) a surfactant; such that a mixture of about 250 to about 1000 milligrams of the abuse resistant liquid with 5 milliliters of water at the mixture's boiling point forms a viscous phase wherein about 33% or less of the pharmaceutically active ingredient can be recovered from the viscous phase drawn up into a 25 millimeter needle having an inner diameter of 0.60 millimeters or which cannot pass through a 25 millimeter needle having an inner diameter of 0.60 millimeters. In the second aspect of the present invention, the surfactant is a phosphatidylcholine concentrate.

In the third aspect of the present invention, the parenteral abuse resistant liquid comprises the liquid of the first aspect and (d) a stabilizer. In the fourth aspect, the stabilizer is one of a colloidal anhydrous silica, a hard fat and a glycerol ester of long chain fatty acid. In the fifth aspect, the stabilizer is a colloidal anhydrous silica.

In the sixth aspect of the present invention, the parenteral abuse resistant liquid comprises the liquid of the fifth aspect and a hydrophilic carrier. In the seventh aspect, the hydrophilic carrier is one of macrogol 400, macrogol 600, macrogol 1500, propylene glycol, glycerol and water.

In the eighth aspect of the present invention, the parenteral abuse resistant liquid comprises the liquid of the third aspect and a stabilizer selected from hard fat or a glycerol ester of long chain fatty acids. In the ninth aspect, the parenteral abuse resistant liquid comprises the liquid of the third aspect, and (e) a lipophilic carrier. In the tenth aspect of the present invention, the lipophilic carrier is one of medium chain triglycerides, medium chain partial glycerides, and a vegetable oil.

In the eleventh aspect of the present invention, the parenteral abuse resistant liquid suitable for encapsulation in a capsule comprises: (a) an abuse-susceptible active pharmaceutical ingredient selected from the group consisting of opiates, opioids, tranquilizers, stimulants and narcotics; (b) a gum selected from the group consisting of acacia, pectin, agar, tragacanth, guar gum, xanthan gum, locust bean gum, tara gum, karaya, gellan gum, welan gum, and rhamsan gum; and (c) a surfactant; such that a mixture of about 250 to about 1000 milligrams of the abuse resistant liquid with 5 milliliters of water at the mixture's boiling point forms a viscous phase wherein about 33% or less of the pharmaceutically active ingredient can be recovered from the viscous phase drawn up into a 25 millimeter needle having an inner diameter of 0.60 millimeters or which cannot pass through a 25 millimeter needle having an inner diameter of 0.60 millimeters. In the twelfth aspect of the present invention, the gum is xanthan gum.

In the thirteenth aspect of the present invention, the parenteral abuse resistant liquid suitable for encapsulation in a capsule comprises: (a) an abuse-susceptible active pharmaceutical ingredient selected from the group consisting of opiates, opioids, tranquilizers, stimulants and narcotics; (b) an ion exchange resin selected from the group consisting of polacrilex resin, sodium polystyrene sulfonate, potassium polyacrilin, and colestyramine resin; and (c) a surfactant; such that a mixture of about 250 to about 1000 milligrams of the abuse resistant liquid with 5 milliliters of water at the mixture's boiling point forms a viscous phase wherein about 33% or less of the pharmaceutically active ingredient can be recovered from the viscous phase drawn up into a 25 millimeter needle having an inner diameter of 0.60 millimeters or which cannot pass through a 25 millimeter needle having an inner diameter of 0.60 millimeters.

In the fourteenth aspect of the present invention, the parenteral abuse resistant liquid suitable for encapsulation in a capsule comprises: (a) an abuse-susceptible active pharmaceutical ingredient selected from the group consisting of opiates, opioids, tranquilizers, stimulants and narcotics; (b) a viscosity enhancer or an ion exchange resin; and (c) a polysorbate surfactant; such that a mixture of about 250 to about 1000 milligrams of the abuse resistant liquid with 5 milliliters of water at the mixture's boiling point forms a viscous wherein about 33% or less of the pharmaceutically active ingredient can be recovered from the viscous phase drawn up into a 25 millimeter needle having an inner diameter of 0.60 millimeters or which cannot pass through a 25 millimeter needle having an inner diameter of 0.60 millimeters. In the fifteenth aspect, the parenteral abuse resistant liquid comprises a polysorbate surfactant selected from polysorbate 80, polysorbate 20, polyoxyethylene (20) sorbitane monolaurate, polyoxyethylene (20) sorbitane monopalmitate, polyoxyethylene (20) sorbitane monostearate, and polyoxyethylene (20) sorbitane monooleate.

In the sixteenth aspect of the present invention, the parenteral abuse resistant liquid suitable for encapsulation in a capsule comprises: (a) an abuse-susceptible active pharmaceutical ingredient selected from the group consisting of opiates, opioids, tranquilizers, stimulants and narcotics; (b) a viscosity enhancer or an ion exchange resin; and (c) a surfactant selected from the group consisting of macrogolglycerol ricinoleate, sorbitol monolaurate, macrogolglycerol hydroxystearate and caprylocaproylmacrogol-8-glycerides; such that a mixture of about 250 to about 1000 milligrams of the abuse resistant liquid with 5 milliliters of water at the mixture's boiling point forms a viscous wherein about 33% or less of the pharmaceutically active ingredient can be recovered from the viscous phase drawn up into a 25 millimeter needle having an inner diameter of 0.60 millimeters or which cannot pass through a 25 millimeter needle having an inner diameter of 0.60 millimeters.

In the seventeenth aspect of the present invention, the parenteral abuse resistant liquid suitable for encapsulation in a capsule comprises: (a) an abuse-susceptible active pharmaceutical ingredient selected from the group consisting of opiates, opioids, tranquilizers, stimulants and narcotics; (b) a viscosity enhancer or an ion exchange resin;
(c) a surfactant; and (d) a carrier; such that a mixture of about 250 to about 1000 milligrams of the abuse resistant liquid with 5 milliliters of water at the mixture's boiling point forms a viscous phase wherein about 33% or less of the pharmaceutically active ingredient can be recovered from the viscous phase drawn up into a 25 millimeter needle having an inner diameter of 0.60 millimeters or which cannot pass through a 25 millimeter needle having an inner diameter of 0.60 millimeters.

In the eighteenth aspect of the present invention, the carrier is selected from glycerol distearate, glycerol dibehenate, medium chain triglycerides, macrogol 400, macrogol 600, propylenglycol, corn oil, corn oil monoglyceride, corn oil diglyceride, soybean oil, sesame oil, safflower oil, sunflower oil, ethanol, phospholipid concentrate, and medium chain partial glycerides.

In the nineteenth aspect of the present invention, the parenteral abuse resistant liquid suitable for encapsulation in a capsule comprises: (a) an abuse-susceptible active pharmaceutical ingredient selected from the group consisting of opiates, opioids, tranquilizers, stimulants and narcotics; (b) a viscosity enhancer or an ion exchange resin; and
(c) macrogol, caprylocaproylmacrogol-8 glycerides, water and glycerol; such that a mixture of about 250 to about 1000 milligrams of the abuse resistant liquid with 5 milliliters of water at the mixture's boiling point forms a viscous phase wherein about 33% or less of the pharmaceutically active ingredient can be recovered from the viscous phase drawn up into a 25 millimeter needle having an inner diameter of 0.60 millimeters or which cannot pass through a 25 millimeter needle having an inner diameter of 0.60 millimeters.

In the twentieth aspect of the present invention, the parenteral abuse resistant liquid suitable for encapsulation in a capsule comprises: (a) an abuse-susceptible active pharmaceutical ingredient selected from the group consisting of opiates, opioids, tranquilizers, stimulants and narcotics; (b) a viscosity enhancer or an ion exchange resin; and
(c) phosphatidylcholine, propylene glycol and caprylocaproyl macrogol-8 glycerides; such that a mixture of about 250 to about 1000 milligrams of the abuse resistant liquid with 5 milliliters of water at the mixture's boiling point forms a viscous phase wherein about 33% or less of the pharmaceutically active ingredient can be recovered from the viscous phase drawn up into a 25 millimeter needle having an inner diameter of 0.60 millimeters or which cannot pass through a 25 millimeter needle having an inner diameter of 0.60 millimeters.

In the twenty-first aspect of the present invention, the parenteral abuse resistant liquid suitable for encapsulation in a capsule comprises: (a) an abuse-susceptible active pharmaceutical ingredient selected from the group consisting of opiates, opioids, tranquilizers, stimulants and narcotics; (b) 2 to 20% ion exchange resin or 0.2 to 0.5% xanthan gum; (c) 40 to 60 wt % Macrogol 600, 3 to 6% glycerol, and 0.5 to 10% water; and 15 to 25 wt % caprylocaproylmacrogol-8 glycerides; and (d) 3 to 10% colloidal anhydrous silica; wherein the weight percentages are calculated with respect to the total weight of the parenteral abuse resistant liquid; and such that a mixture of about 250 to about 1000 milligrams of the abuse resistant liquid with 5 milliliters of water at the mixture's boiling point forms a viscous phase wherein about 33% or less of the pharmaceutically active ingredient can be recovered from the viscous phase drawn up into a 25 millimeter needle having an inner diameter of 0.60 millimeters or which cannot pass through a 25 millimeter needle having an inner diameter of 0.60 millimeters.

In the twenty-second aspect of the present invention, the parenteral abuse resistant liquid suitable for encapsulation in a capsule comprises: (a) an abuse-susceptible active pharmaceutical ingredient selected from the group consisting of opiates, opioids, tranquilizers, stimulants and narcotics; (b) 2 to 5% xanthan gum; (c) 4 to 20% glycerol stearate or glycerol dibehenate; 10 to 70% medium chain triglycerides; 4 to 50% polysorbate 80; 4 to 15% sorbitol monolaurate; and 3 to 10% macrogolglycerol ricinoleate or macrogolglycerol hydroxystearate; and (d) a stabilizer; 40 to 70% hard fat; and 1 to 5% colloidal anhydrous silica; wherein the weight percentages are calculated with respect to the total weight of the parenteral abuse resistant liquid; and such that a mixture of about 250 to about 1000 milligrams of the abuse resistant liquid with 5 milliliters of water at the mixture's boiling point forms a viscous phase wherein about 33% or less of the pharmaceutically active ingredient can be recovered from the viscous phase drawn up into a 25 millimeter needle having an inner diameter of 0.60 millimeters or which cannot pass through a 25 millimeter needle having an inner diameter of 0.60 millimeters.

In the twenty-third aspect of the present invention, the parenteral abuse resistant liquid suitable for encapsulation in a capsule comprises: (a) an abuse-susceptible active pharmaceutical ingredient selected from the group consisting of opiates, opioids, tranquilizers, stimulants and narcotics; (b) 0.2 to 5% xanthan gum; (c) 50 to 80% phosphatidylchholine concentrate; 15 to 15% caprylocaproylmacrogol 8 glycerides; 5 to 10% polysorbate 80; and 4 to 10% water; and (d) 1 to 10% colloidal anhydrous silica; wherein the weight percentages are calculated with respect to the total weight of the parenteral abuse resistant liquid; and such that a mixture of about 250 to about 1000 milligrams of the abuse resistant liquid with 5 milliliters of water at the mixture's boiling point forms a viscous phase wherein about 33% or less of the pharmaceutically active ingredient can be recovered from the viscous phase drawn up into a 25 millimeter needle having an inner diameter of 0.60 millimeters or which cannot pass through a 25 millimeter needle having an inner diameter of 0.60 millimeters.

In the twenty-fourth aspect of the present invention, the parenteral abuse resistant liquid suitable for encapsulation in a capsule comprises: (a) an abuse-susceptible active pharmaceutical ingredient selected from the group consisting of N-{1-[2-(4-ethyl-5-oxo-2-tetrazolin-1-yl)ethyl]-4-methoxymethyl-4-piperidyl}propionanilide; alfentanil; 5,5-diallylbarbituric acid; allobarbital; allylprodine; alphaprodine; 8-chloro-1-methyl-6-phenyl-4H-[1,2,4]triazolo[4,3-a][1,4]-benzodiazepine; alprazolam; 2-diethylaminopropiophenone; amfepramone, (±)-amethylphenethylamine; amphetamine; 2-(α-methylphenethylamino)-2-phenylacetonitrile; amphetaminil; 5-ethyl-5-isopentylbarbituric acid; amobarbital; anileridine; apocodeine; 5,5-diethylbarbituric acid; barbital; benzylmorphine; bezitramide; 7-bromo-5-(2-pyridyl)-1H-1,4-benzodiazepine-2 (3H)-one; bromazepam; 2-bromo-4-(2-chlorophenyl)-9-methyl-1-6H-thieno[3,2-f][1,2,4]triazolo[4,3-a][1,4] diazepine; brotizolam, 17-cyclopropylmethyl-4,5a-epoxy-7a[(S)-1-hydroxy-1,2,2-trimethyl-propyl]-6-methoxy-6,14-endo-ethanomorphinan-3-ol; buprenorphine; 5-butyl-5-ethylbarbituric acid; butobarbital; butorphanol; (7-chloro-1, 3-dihydro-1-methyl-2-oxo-5-phenyl-2H-1,4-benzodiazepin-3-yl)dimethylcarbamate; camazepam; (1S, 2S)-2-amino-1-phenyl-1-propanol; cathine; d-norpseudoephedrine; 7-chloro-N-methyl-5-phenyl-3H-1, 4-benzodiazepin-2-yl-amine 4-oxide; chlordiazepoxide, 7-chloro-1-methyl-5-phenyl-1H-1,5-benzodi-azepine-2,4 (3H,5H)-dione; clobazam, 5-(2-chlorophenyl)-7-nitro-1H-1, 4-benz-odiazepin-2(3H)-one; clonazepam; clonitazene; 7-chloro-2,3-dihydro-2-oxo-5-phenyl-1H-1,4-benzodiazepine-3-carboxylic acid; clorazepate; 5-(2-chlorophenyl)-7-ethyl-1-methyl-1H-thieno[2,3-e][1,4]diazepin-2(3H)-one; clotiazepam; 10-chloro-11b-(2-chlorophenyl)-2,3,7,11b-tetrahydrooxazolo[3,2-d][1,4]benzodiazepin-6(5H)-one; cloxazolam; (−)-methyl-[3β-benzoyloxy-2(1αH,5αH)-tropane carboxylate]; cocaine; (5α,6α)-7,8-didehydro-4,5-epoxy-3-methoxy-17-methylmorphinan-6-ol; 4,5α-epoxy-3-methoxy-17-methyl-7-morphinen-6α-ol; codeine; 5-(1-cyclohexenyl)-5-ethyl barbituric acid; cyclobarbital; cyclorphan; cyprenorphine; 7-chloro-5-(2-chlorophenyl)-1H-1,4-benzodiazepin-2(3H)-one; delorazepam; desomorphine; dextromoramide; (+)-(1-benzyl-3-dimethylamino-2-methyl-1-phenylpropyl)propionate; dextropropoxyphene; dezocine; diampromide; diamorphine; 7-chloro-1-methyl-5-phenyl-1H-1,4-benzodiazepin-2(3H)-on; diazepam; 4,5α-epoxy-3-methoxy-17-methyl-6α-morphinanol; dihydrocodeine; 4,5α-epoxy-17-methyl-3,6a-morphinandiol; dihydromorphine; dimenoxadol; dimephetamol; dimethylthiambutene; dioxaphetyl butyrate; dipipanone; (6aR,10aR)-6,6,9-trimethyl-3-pentyl-6a,7,8,10a-tetrahydro-6H-benzo[c]chromen-1-ol; dronabinol; eptazocine; 8-chloro-6-phenyl-4H-[1,2,4]-triazolo[4,3-(a)][1,4]benzodiazepine; estazolam; ethoheptazine; ethylmethylthiambutene; ethyl[7-chloro-5-(2-fluorophenyl)-2,3-dihydro-2-oxo-1H-1,4-benzodiazepine-3-carboxylate]; ethyl loflazepate; 4,5α-epoxy-3-ethoxy-17-methyl-7-morphinen-6α-ol; ethylmorphine; etonitazene; 4,5α-epoxy-7α-(1-hydroxy-1-methylbutyl)-6-methoxy-17-methyl-6,14-endo-etheno-morphinan-3-ol; etorphine; N-ethyl-3-phenyl-8,9,10-trinorbornan-2-ylamine; fencamfamine; 7-[2-(α-methylphenethylamino)ethyl]-theophylline; fenethylline; 3-(α-methylphenethylamino) propionitrile; fenproporex; N-(1-phenethyl-4-piperidyl) propionanilide; fentanyl; 7-chloro-5-(2-fluorophenyl)-1-methyl-1H-1,4-benzodiazepin-2(3H)-one; fludiazepam; 5-(2-fluorophenyl)-1-methyl-7-nitro-1H-1,4-benzodiazepin-2(3H)-one; flunitrazepam; 7-chloro-1-(2-diethylaminoethyl)-5-(2-fluorophenyl)-1H-1,4-benzodiazepin-2(3H)-one; flurazepam; 7-chloro-5-phenyl-1-(2,2,2-trifluoroethyl)-1H-1,4-benzodiazepin-2(3H)-one; halazepam; 10-bromo-11b-(2-fluorophenyl)-2,3,7,11b-tetrahydro[1,3]oxazolyl[3, 2-d][1,4]benzodiazepin-6(5H)-one; haloxazolam; heroin; 4,5α-epoxy-3-methoxy-17-methyl-6-morphinanone; hydrocodone; 4,5α-epoxy-3-hydroxy-17-methyl-6-morphinanone; hydromorphone; hydroxypethidine; isomethadone; hydroxymethylmorphinan; 11-chloro-8,12b-dihydro-2,8-dimethyl-12b-phenyl-4H-[1,3]oxazino[3,2d][1,4]benzodiazepine-4,7(6H)-dione; ketazolam; 1-[4-(3-hydroxyphenyl)-1-methyl-4-piperidyl]-1-propanone; ketobemidone; (3S,6S)-6-dimethylamino-4,4-diphenylheptan-3-yl acetate; levacetylmethadol; LAAM; (−)-6-dimethylamino-4,4-diphenol-3-heptanone; levomethadone; (−)-17-methyl-3-morphinanol; levorphanol; levophenacylmorphane; lofentanil;

6-(2-chlorophenyl)-2-(4-methyl-1-piperazinylmethylene)-8-nitro-2H-imidazo[1,2-a][1,4]-benzodiazepin-1(4H)-one; loprazolam; 7-chloro-5-(2-chlorophenyl)-3-hydroxy-1H-1,4-benzodiazepin-2(3H)-one; lorazepam; 7-chloro-5-(2-chlorophenyl)-3-hydroxy-1-methyl-1H-1,4-benzodiazepin-2(3H)-one; lormetazepam; 5-(4-chlorophenyl)-2,5-dihydro-3H-imidazo[2,1a]isoindol-5-ol; mazindol; 7-chloro-2,3-dihydro-1-methyl-5-phenyl-1H-1,4-benzodiazepine; medazepam; N-(3-chloropropyl)-α-methylphenethylamine; mefenorex; meperidine; 2-methyl-2-propyltrimethylene dicarbamate; meprobamate; meptazinol; metazocine; methylmorphine; N,α-dimethylphenethylamine; methamphetamine; (+)-6-dimethylamino-4,4-diphenol-3-heptanone; methadone; 2-methyl-3-o-tolyl-4(3H)-quinazolinone; methaqualone; methyl[2-phenyl-2-(2-piperidyl)acetate]; methylphenidate; 5-ethyl-1-methyl-5-phenylbarbituric acid; methylphenobarbital; 3,3-diethyl-5-methyl-2,4-piperidinedione; methyprylon; metopon; 8-chloro-6-(2-fluorophenyl)-1-methyl-4H-imidazo[1,5-a][1,4]benzodiazepine; midazolam; 2-(benzhydrylsulfinyl)acetamide; modafinil; (5α,6α)-7,8-didehydro-4,5-epoxy-17-methyl-7-methylmorphinan-3,6-diol; morphine; myrophine; (+)-trans-3-(1,1-dimethylheptyl)-7,8,10,10α-tetrahydro-1-hydroxy-6,6-dimethyl-6H-dibenzo-[b,d]pyran-9(6αH)one; nabilone; nalbuphene; nalorphine; narceine; nicomorphine; 1-methyl-7-nitro-5-phenyl-1H-1,4-benzodiazepin-2(3H)-one; nimetazepam; 7-nitro-5-phenyl-1H-1,4-benzodiazepin-2(3H)-one; nitrazepam; 7-chloro-5-phenyl-1H-1,4-benzodiazepin-2(-3H)-one; nordazepam; norlevorphanol; 6-dimethylamino-4,4-diphenyl-3-hexanone; normethadone; normorphine; norpipanone; opium; 7-chloro-3-hydroxy-5-phenyl-1H-1,4-benzodiazepin-2(3H)-one; oxazepam; (cis-/trans-)-10-chloro-2,3,7,11b-tetrahydro-2-methyl-11b-phenyloxazolo[3,2-d][1,4]benzodiazepin-6-(5H)-one; oxazolam; 4,5α-epoxy-14-hydroxy-3-methoxy-17-methyl-6-morphinanone; oxycodone; oxymorphone; papaveretum; 2-imino-5-phenyl-4-oxazolidinone; pernoline; 1,2,3,4,5,6-hexahydro-6,11-dimethyl-3-(3-methyl-2-butenyl)-2,6-methano-3-benzazocin-8-ol; pentazocine; 5-ethyl-5-(1-methylbutyl)-barbituric acid; pentobarbital; ethyl-(1-methyl-4-phenyl-4-piperidinecarboxylate); pethidine; phenadoxone; phenomorphane; phenazocine; phenoperidine; piminodine; pholcodeine; 3-methyl-2-phenylmorpholine; phenmetrazine; 5-ethyl-5-phenylbarbituric acid; phenobarbital; α,α-dimethylphenethylamine; phentermine; (R)-3-[-1-hydroxy-2-(methylamino)ethyl]phenol; phenylephrine, 7-chloro-5-phenyl-1-(2-propynyl)-1H-1,4-benzodiazepin-2(3H)-one; pinazepam; α-(2-piperidyl)benzhydryl alcohol; pipradrol; 1'-(3-cyano-3,3-diphenylpropyl)[1,4'-bipiperidine]-4'-carboxamide; piritramide; 7-chloro-1-(cyclopropylmethyl)-5-phenyl-1H-1,4-benzodiazepin-2(3H)-one; prazepam; profadol; proheptazine; promedol; properidine; propoxyphene; N-(1-methyl-2-piperidinoethyl)-N-(2-pyridyl)propionamide; methyl {3-[4-methoxycarbonyl-4-(N-phenylpropanamido)piperidino]propanoate}; (S,S)-2-methylamino-1-phenylpropan-1-ol; pseudoephedrine, remifentanil; 5-sec-butyl-5-ethylbarbituric acid; secbutabarbital; 5-allyl-5-(1-methylbutyl)-barbituric acid; secobarbital; N-{4-methoxymethyl-1-[2-(2-thienyl)ethyl]-4-piperidyl}propionanilide; sufentanil; 7-chloro-2-hydroxymethyl-5-phenyl-1H-1,4-benzodiazepin-2(3H)-one; temazepam; 7-chloro-5-(1-cyclohexenyl)-1-methyl-1H-1,4-benzodiazepin-2(3H)-one; tetrazepam; ethyl (2-dimethylamino-1-phenyl-3-cyclohexene-1-carboxylate; cis-/trans-tilidine; tramadol; 8-chloro-6-(2-chlorophenyl)-1-methyl-4H-[1,2,4]triazolo[4,3-a][1,4]benzodiazepine; triazolam; 5-(1-methylbutyl)-5-vinylbarbituric acid; vinylbital; (1R*,2R*)-3-(3-dimethylamino-1-ethyl-2-methylpropyl)phenol; (1R,2R,4S)-2-(dimethylamino)methyl-4-(p-fluorobenzyloxy)-1-(m-methoxyphenyl)cyclohexanol; a prodrug thereof, a pharmaceutically acceptable salt thereof, an adduct thereof, and a solvate thereof, (b) a viscosity enhancer or an ion exchange resin; and (c) a surfactant; such that a mixture of about 250 to about 1000 milligrams of the abuse resistant liquid with 5 milliliters of water at the mixture's boiling point forms a viscous phase wherein about 33% or less of the pharmaceutically active ingredient can be recovered from the viscous phase drawn up into a 25 millimeter needle having an inner diameter of 0.60 millimeters or which cannot pass through a 25 millimeter needle having an inner diameter of 0.60 millimeters.

In the twenty-fifth aspect of the present invention, the parenteral abuse resistant liquid suitable for encapsulation in a capsule comprises: (a) an abuse-susceptible active pharmaceutical ingredient selected from the group consisting of codeine, tramadol, anileridine, prodine, pethidine, hydrocodone, morphine, oxycodone, methadone, diamorphine, hydromorphone, oxymorphone, 7-hydroxymitragynine, buprenorphine, fentanyl, sufentanil, levorphanol, meperidine, dihydrocodeine, dihydromorphine, morphine, hydromorphone, oxymorphone, tilidine, a prodrug thereof, a pharmaceutically acceptable salt thereof, and a solvate thereof, (b) a viscosity enhancer or an ion exchange resin; and (c) a surfactant; such that a mixture of about 250 to about 1000 milligrams of the abuse resistant liquid with 5 milliliters of water at the mixture's boiling point forms a viscous wherein about 33% or less of the pharmaceutically active ingredient can be recovered from the viscous phase drawn up into a 25 millimeter needle having an inner diameter of 0.60 millimeters or which cannot pass through a 25 millimeter needle having an inner diameter of 0.60 millimeters.

In the twenty-sixth aspect of the present invention, the parenteral abuse resistant liquid suitable for encapsulation in a capsule comprises: (a) an abuse-susceptible active pharmaceutical ingredient selected from the group consisting of opiates, opioids, tranquilizers, stimulants and narcotics; (b) a viscosity enhancer or an ion exchange resin; and (c) a surfactant; such that a mixture of about 250 to about 1000 milligrams of the abuse resistant liquid with 5 milliliters of water at the mixture's boiling point forms a viscous phase wherein about 33% or less of the pharmaceutically active ingredient can be recovered from the viscous phase drawn up into a 25 millimeter needle having an inner diameter of 0.60 millimeters or which cannot pass through a 25 millimeter needle having an inner diameter of 0.60 millimeters; and is resistant to alcohol dose dumping.

In the twenty-seventh aspect of the present invention, the parenteral abuse resistant liquid suitable for encapsulation in a capsule comprises: (a) an abuse-susceptible active pharmaceutical ingredient selected from the group consisting of opiates, opioids, tranquilizers, stimulants and narcotics; (b) a viscosity enhancer or an ion exchange resin; and (c) a surfactant; such that a mixture of about 250 to about 1000 milligrams of the abuse resistant liquid with 5 milliliters of water at the mixture's boiling point forms a viscous phase wherein about 33% or less of the pharmaceutically active ingredient can be recovered from the viscous phase drawn up into a 25 millimeter needle having an inner diameter of 0.60 millimeters or which cannot pass through a 25 millimeter needle having an inner diameter of 0.60 millimeters; and is resistant to solvent, acidic or aqueous extraction.

Further, the present invention is directed to a parenteral abuse resistant capsule comprising the abuse resistant liquid in a form suitable for encapsulation in a capsule.

In the twenty-eighth aspect of the present invention, the parenteral abuse resistant capsule comprises: (1) a fill including: (a) an abuse-susceptible active pharmaceutical ingredient selected from the group consisting of opiates, opioids, tranquilizers, stimulants and narcotics; (b) a viscosity enhancer or an ion exchange resin; and (c) a surfactant; such that a mixture of about 250 to about 1000 milligrams of the abuse resistant liquid with 5 milliliters of water at the mixture's boiling point forms a viscous phase wherein about 33% or less of the pharmaceutically active ingredient can be recovered from the viscous phase drawn up into a 25 millimeter needle having an inner diameter of 0.60 millimeters or which cannot pass through a 25 millimeter needle having an inner diameter of 0.60 millimeters; and (2) a shell.

In the twenty-ninth aspect of the present invention, the parenteral abuse resistant capsule comprises: (1) a fill including: (a) an abuse-susceptible active pharmaceutical ingredient selected from the group consisting of opiates, opioids, tranquilizers, stimulants and narcotics; (b) an ion exchange resin; and (c) a surfactant; such that a mixture of about 250 to about 1000 milligrams of the abuse resistant liquid with 5 milliliters of water at the mixture's boiling point forms a viscous phase wherein about 33% or less of the pharmaceutically active ingredient can be recovered from the viscous phase drawn up into a 25 millimeter needle having an inner diameter of 0.60 millimeters or which cannot pass through a 25 millimeter needle having an inner diameter of 0.60 millimeters; and (2) a shell; wherein the ion exchange resin creates a drug-ion exchange complex that dissociates within 30 minutes after entry into the gastrointestinal tract.

In the thirtieth aspect of the present invention, the parenteral abuse resistant capsule comprises: (1) a fill including: (a) an abuse-susceptible active pharmaceutical ingredient selected from the group consisting of opiates, opioids, tranquilizers, stimulants and narcotics; (b) a viscosity enhancer or an ion exchange resin; and (c) a surfactant; such that a mixture of about 250 to about 1000 milligrams of the abuse resistant liquid with 5 milliliters of water at the mixture's boiling point forms a viscous phase wherein about 33% or less of the pharmaceutically active ingredient can be recovered from the viscous phase drawn up into a 25 millimeter needle having an inner diameter of 0.60 millimeters or which cannot pass through a 25 millimeter needle having an inner diameter of 0.60 millimeters; and (2) a shell; wherein the capsule releases more than 80% of the active pharmaceutical ingredient within the gastrointestinal tract within 30 minutes of administration.

In the thirty-first aspect of the present invention, the parenteral abuse resistant capsule comprises: (1) a fill including: (a) an abuse-susceptible active pharmaceutical ingredient selected from the group consisting of opiates, opioids, tranquilizers, stimulants and narcotics; (b) a viscosity enhancer or an ion exchange resin; and (c) a surfactant; such that a mixture of about 250 to about 1000 milligrams of the abuse resistant liquid with 5 milliliters of water at the mixture's boiling point forms a viscous phase wherein about 33% or less of the pharmaceutically active ingredient can be recovered from the viscous phase drawn up into a 25 millimeter needle having an inner diameter of 0.60 millimeters or which cannot pass through a 25 millimeter needle having an inner diameter of 0.60 millimeters; and (2) a shell; and the capsule provides extended release.

In the thirty-second aspect of the present invention, the parenteral abuse resistant capsule comprises: (1) a fill including: (a) an abuse-susceptible active pharmaceutical ingredient selected from the group consisting of opiates, opioids, tranquilizers, stimulants and narcotics; (b) a viscosity enhancer or an ion exchange resin; and (c) a surfactant; such that a mixture of about 250 to about 1000 milligrams of the abuse resistant liquid with 5 milliliters of water at the mixture's boiling point forms a viscous wherein about 33% or less of the pharmaceutically active ingredient can be recovered from the viscous phase drawn up into a 25 millimeter needle having an inner diameter of 0.60 millimeters or which cannot pass through a 25 millimeter needle having an inner diameter of 0.60 millimeters; and (2) a shell; wherein the capsule is a soft capsule or a hard capsule.

DETAILED DESCRIPTION

The present invention is directed to the development of an immediate release capsule formulation. More specifically, the invention is directed to an immediate release capsule formulation, which mitigates the abuse of abuse-susceptible active pharmaceutical ingredients by direct intravenous injection.

The present invention is also directed to the development of an extended release capsule formulation. More specifically, the invention is directed to an extended release capsule formulation, which mitigates the abuse of abuse-susceptible active pharmaceutical ingredients by direct intravenous injection.

The abuse problem that the present invention mitigates is the illicit isoloation of the abuse-susceptible active pharmaceutical ingredient from a capsule fill. The concern is that the user can recover the fill composition and solubilize the fill with a small amount water, such as about 5 mL of water per 1 capsule. This mixture may then be heated, optionally boiled, and filtered through a filter, such as a cigarette filter, into a hypodermic syringe. Such a syringe may be an insulin syringe equipped with a needle. The syringes that are used for insulin injections typically comprise 20 to 31 gauge needles. Typically, due to the viscosity of the material, the illicit drug user will select relatively thicker gauge needles, such as a 20 gauge needle (about 0.91 mm outer diameter, 0.60 mm inner diameter). In the alternative, a plurality of capsules containing the fill comprising the active pharmaceutical ingredient is exposed to hot or boiling water to solubilize the capsule shell to obtain the active pharmaceutical ingredient, which may be further purified.

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

As used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

One of the aspects of the present invention is to provide for an abuse resistant liquid for encapsulation in a capsule which when mixed with water and heated, results in a turbid, bubbling mixture that is not injectable with a standard insulin syringe.

Another aspect of the present invention is to provide for a capsule comprising a tamper resistant fill formulation which when mixed with water and heated, results in a turbid, bubbling mixture that is not injectable with a standard insulin syringe.

There are several different characteristics that may make the fill formulation abuse resistant. One characteristic that makes the fill formulation abuse resistant is that the viscosity increases upon heating or boiling of the formulation in water. In this embodiment, upon exposure to water, the viscosity of the mixture increases to such a level that it is difficult or impossible to fill the insulin syringe with the mixture. In one embodiment, the viscosity of the heated mixture increases to the level that it may not be deliverable even through needles with the largest diameters commonly used in delivery of insulin.

A second characteristic that makes a fill formulation abuse resistant is that upon heating or boiling the mixture of the fill with water, bubbles occur in the mixture. The presence of such bubbles makes it more difficult to draw the mixture into the syringe. The bubbles also have a deterrent effect in that intravenous drug users tend to avoid introduction of air bubbles into their bloodstream due to their fear of an air embolism.

Another aspect of the present invention is an abuse resistant liquid suitable for encapsulation in a capsule, which when mixed with water and heated, results in a mixture which when filtered to provide a liquid extract, the liquid extract comprises less than 33% of the dosage, and a capsule comprising such abuse resistant fill formulation.

Yet another aspect of the present invention is an abuse resistant liquid suitable for encapsulation in a capsule, wherein the liquid comprises an ion exchange resin that creates a drug ion exchange complex with the abuse-susceptible active pharmaceutical ingredient that dissociates within 30 minutes within the gastrointestinal tract, and a capsule comprising such abuse resistant fill formulation.

A further aspect of the present invention is an immediate release capsule. Such a capsule releases more than 80% of the active pharmaceutical ingredient within the gastrointestinal tract within 30 minutes of administration.

A still further aspect of the present invention is a controlled release capsule. An example of a controlled release capsule is an extended release capsule.

Although there are many combinations of the fill components that may work well to deliver the active pharmaceutical ingredient, it was surprising that only certain combinations of components result in parenteral abuse resistant fill formulations.

The abuse resistant capsule of the present invention comprises the shell and the fill. The "fill", as related to the present invention, is the liquid or semiliquid fluid that is encapsulated by the shell. The composition of the fill is formulated so that the fill is tamper resistant.

The fill comprises the abuse-susceptible active pharmaceutical ingredient, and a blend of inactive ingredients. The blend may comprise one or more of a solvent, a surfactant, and a viscosity enhancer. Optionally, the blend may further comprise a plasticizer. Optionally, the blend may further comprise an ion exchange resin.

The abuse-susceptible active pharmaceutical ingredient as used in herein is any pharmaceutically active ingredient that may be parenterally abused.

Abuse-susceptible active pharmaceutical ingredients include opiates, opioids, tranquilizers, stimulants and narcotics as well as active pharmaceutical ingredients that are currently commonly abused parenterally, and also any active pharmaceutical ingredient that has the potential of being abused parenterally.

In one embodiment of the present invention, the abuse-susceptible active pharmaceutical ingredient is an opioid. The term "opioid" refers to a psychoactive compound that works by binding to opioid receptors. Opioids are commonly used in the medical field for their analgesic effects. Examples of opioids include codeine, tramadol, anileridine, prodine, pethidine, hydrocodone, morphine, oxycodone, methadone, diamorphine, hydromorphone, oxymorphone, 7-hydroxymitragynine, buprenorphine, fentanyl, sufentanil, levorphanol, meperidine, tilidine, dihydrocodeine, and dihydromorphine.

Examples of the abuse-susceptible active pharmaceutical ingredient include N-{1-[2-(4-ethyl-5-oxo-2-tetrazolin-1-yl)ethyl]-4-methoxymethyl-4-piperidyl}propionanilide; alfentanil; 5,5-diallylbarbituric acid; allobarbital; allylprodine; alphaprodine; 8-chloro-1-methyl-6-phenyl-4H-[1,2,4]triazolo[4,3-a][1,4]-benzodiazepine; alprazolam; 2-diethylaminopropiophenone; amfepramone, (+)-amethylphenethylamine; amphetamine; 2-(α-methylphenethylamino)-2-phenylacetonitrile; amphetaminil; 5-ethyl-5-isopentylbarbituric acid; amobarbital; anileridine; apocodeine; 5,5-diethylbarbituric acid; barbital; benzylmorphine; bezitramide; 7-bromo-5-(2-pyridyl)-1H-1,4-benzodiazepine-2(3H)-one; bromazepam; 2-bromo-4-(2-chlorophenyl)-9-methyl-1-6H-thieno[3,2-f][1,2,4]triazolo[4,3-a][1,4] diazepine; brotizolam, 17-cyclopropylmethyl-4,5α-epoxy-7a[(S)-1-hydroxy-1,2,2-trimethyl-propyl]-6-methoxy-6,14-endo-ethanomorphinan-3-ol; buprenorphine; 5-butyl-5-ethylbarbituric acid; butobarbital; butorphanol; (7-chloro-1,3-dihydro-1-methyl-2-oxo-5-phenyl-2H-1,4-benzodiazepin-3-yl)dimethylcarbamate; camazepam; (1S,2S)-2-amino-1-phenyl-1-propanol; cathine; d-norpseudoephedrine; 7-chloro-N-methyl-5-phenyl-3H-1,4-benzodiazepin-2-yl-amine 4-oxide; chlordiazepoxide, 7-chloro-1-methyl-5-phenyl-1H-1,5-benzodi-azepine-2,4(3H,5H)-dione; clobazam, 5-(2-chlorophenyl)-7-nitro-1H-1,4-benz-odiazepin-2(3H)-one; clonazepam; clonitazene; 7-chloro-2,3-dihydro-2-oxo-5-phenyl-1H-1,4-benzodiazepine-3-carboxylic acid; clorazepate; 5-(2-chlorophenyl)-7-ethyl-1-methyl-1H-thieno[2,3-e][1,4]diazepin-2(3H)-one; clotiazepam; 10-chloro-11b-(2-chlorophenyl)-2,3,7,11b-tetrahydrooxazolo[3,2-d][1,4]benzodiazepin-6(5H)-one; cloxazolam; (−)-methyl-[3β-benzoyloxy-23(1αH,5αH)-tropane carboxylate]; cocaine; (5α,6α)-7,8-didehydro-4,5-epoxy-3-methoxy-17-methylmorphinan-6-ol; 4,5α-epoxy-3-methoxy-17-methyl-7-morphinen-6α-ol; codeine; 5-(1-cyclohexenyl)-5-ethyl barbituric acid; cyclobarbital; cyclorphan; cyprenorphine; 7-chloro-5-(2-chlorophenyl)-1H-1,4-benzodiazepin-2(3H)-one; delorazepam; desomorphine; dextromoramide; (+)-(1-benzyl-3-dimethylamino-2-methyl-1-phenylpropyl)propionate; dextropropoxyphene; dezocine; diampromide; diamorphone; 7-chloro-1-methyl-5-phenyl-1H-1,4-benzodiazepin-2(3H)-on; diazepam; 4,5α-epoxy-3-methoxy-17-methyl-6α-morphinanol; dihydrocodeine; 4,5α-epoxy-17-methyl-3,6α-morphinandiol;

dihydromorphine; dimenoxadol; dimephetamol; dimethylthiambutene; dioxaphetyl butyrate; dipipanone; (6aR,10aR)-6,6,9-trimethyl-3-pentyl-6a,7,8,10a-tetrahydro-6H-benzo[c]chromen-1-ol; dronabinol; eptazocine; 8-chloro-6-phenyl-4H-[1,2,4]-triazolo[4,3-(a)][1,4]benzodiazepine; estazolam; ethoheptazine; ethylmethylthiambutene; ethyl[7-chloro-5-(2-fluorophenyl)-2,3-dihydro-2-oxo-1H-1,4-benzodiazepine-3-carboxylate]; ethyl loflazepate; 4,5α-epoxy-3-ethoxy-17-methyl-7-morphinen-6α-ol; ethylmorphine; etonitazene; 4,5α-epoxy-7α-(1-hydroxy-1-methylbutyl)-6-methoxy-17-methyl-6,14-endo-etheno-morphinan-3-ol; etorphine; N-ethyl-3-phenyl-8,9,10-trinorbornan-2-ylamine; fencamfamine; 7-[2-(α-methylphenethylamino)ethyl]-theophylline; fenethylline; 3-(α-methylphenethylamino) propionitrile; fenproporex; N-(1-phenethyl-4-piperidyl) propionanilide; fentanyl; 7-chloro-5-(2-fluorophenyl)-1-methyl-1H-1,4-benzodiazepin-2(3H)-one; fludiazepam; 5-(2-fluorophenyl)-1-methyl-7-nitro-1H-1,4-benzodiazepin-2(3H)-one; flunitrazepam; 7-chloro-1-(2-diethylaminoethyl)-5-(2-fluorophenyl)-1H-1,4-benzodiazepin-2(3H)-one; flurazepam; 7-chloro-5-phenyl-1-(2,2,2-trifluoroethyl)-1H-1,4-benzodiazepin-2(3H)-one; halazepam; 10-bromo-11b-(2-fluorophenyl)-2,3,7,11b-tetrahydro[1,3]oxazolyl[3,2-d][1,4]benzodiazepin-6(5H)-one; haloxazolam; heroin; 4,5α-epoxy-3-methoxy-17-methyl-6-morphinanone; hydrocodone; 4,5α-epoxy-3-hydroxy-17-methyl-6-morphinanone; hydromorphone; hydroxypethidine; isomethadone; hydroxymethylmorphinan; 11-chloro-8,12b-dihydro-2,8-dimethyl-12b-phenyl-4H-[1,3]oxazino[3,2d][1,4]benzodiazepine-4,7(6H)-dione; ketazolam; 1-[4-(3-hydroxyphenyl)-1-methyl-4-piperidyl]-1-propanone; ketobemidone; (3S,6S)-6-dimethylamino-4,4-diphenylheptan-3-yl acetate; levacetylmethadol; LAAM; (−)-6-dimethylamino-4,4-diphenol-3-heptanone; levomethadone; (−)-17-methyl-3-morphinanol; levorphanol; levophenacylmorphane; lofentanil; 6-(2-chlorophenyl)-2-(4-methyl-1-piperazinylmethylene)-8-nitro-2H-imidazo[1,2-a][1,4]-benzodiazepin-1(4H)-one; loprazolam; 7-chloro-5-(2-chlorophenyl)-3-hydroxy-1H-1,4-benzodiazepin-2(3H)-one; lorazepam; 7-chloro-5-(2-chlorophenyl)-3-hydroxy-1-methyl-1H-1,4-benzodiazepin-2 (3H)-one; lormetazepam; 5-(4-chlorophenyl)-2,5-dihydro-3H-imidazo[2,1a]isoindol-5-ol; mazindol; 7-chloro-2,3-dihydro-1-methyl-5-phenyl-1H-1,4-benzodiazepine; medazepam; N-(3-chloropropyl)-α-methylphenethylamine; mefenorex; meperidine; 2-methyl-2-propyltrimethylene dicarbamate; meprobamate; meptazinol; metazocine; methylmorphine; N,α-dimethylphenethylamine; methamphetamine; (±)-6-dimethylamino-4,4-diphenol-3-heptanone; methadone; 2-methyl-3-o-tolyl-4(3H)-quinazolinone; methaqualone; methyl[2-phenyl-2-(2-piperidyl)acetate]; methylphenidate; 5-ethyl-1-methyl-5-phenylbarbituric acid; methylphenobarbital; 3,3-diethyl-5-methyl-2,4-piperidinedione; methyprylon; metopon; 8-chloro-6-(2-fluorophenyl)-1-methyl-4H-imidazo[1,5-a][1,4]benzodiazepine; midazolam; 2-(benzhydrylsulfinyl)acetamide; modafinil; (5α,6α)-7,8-didehydro-4,5-epoxy-17-methyl-7-methylmorphinan-3,6-diol; morphine; myrophine; (±)-trans-3-(1,1-dimethylheptyl)-7,8,10,10α-tetrahydro-1-hydroxy-6,6-dimethyl-6H-dibenzo-[b,d]pyran-9(6αH)one; nabilone; nalbuphene; nalorphine; narceine; nicomorphine; 1-methyl-7-nitro-5-phenyl-1H-1,4-benzodiazepin-2(3H)-one; nimetazepam; 7-nitro-5-phenyl-1H-1,4-benzodiazepin-2(3H)-one; nitrazepam; 7-chloro-5-phenyl-1H-1,4-benzodiazepin-2(-3H)-one; nordazepam; norlevorphanol; 6-dimethylamino-4,4-diphenyl-3-hexanone; normethadone; normorphine; norpipanone; opium; 7-chloro-3-hydroxy-5-phenyl-1H-1,4-benzodiazepin-2(3H)-one; oxazepam; (cis-/trans-)-10-chloro-2,3,7,11b-tetrahydro-2-methyl-11b-phenyloxazolo[3,2-d][1,4]benzodiazepin-6-(5H)-one; oxazolam; 4,5α-epoxy-14-hydroxy-3-methoxy-17-methyl-6-morphinanone; oxycodone; oxymorphone; papaveretum; 2-imino-5-phenyl-4-oxazolidinone; pemoline; 1,2,3,4,5,6-hexahydro-6,11-dimethyl-3-(3-methyl-2-butenyl)-2,6-methano-3-benzazocin-8-ol; pentazocine; 5-ethyl-5-(1-methylbutyl)-barbituric acid; pentobarbital; ethyl-(1-methyl-4-phenyl-4-piperidinecarboxylate); pethidine; phenadoxone; phenomorphane; phenazocine; phenoperidine; piminodine; pholcodeine; 3-methyl-2-phenylmorpholine; phenmetrazine; 5-ethyl-5-phenylbarbituric acid; phenobarbital; α,α-dimethylphenethylamine; phentermine; (R)-3-[-1-hydroxy-2-(methylamino)ethyl]phenol; phenylephrine, 7-chloro-5-phenyl-1-(2-propynyl)-1H-1,4-benzodiazepin-2(3H)-one; pinazepam; α-(2-piperidyl)benzhydryl alcohol; pipradrol; 1'-(3-cyano-3,3-diphenylpropyl) [1,4'-bipiperidine]-4'-carboxamide; piritramide; 7-chloro-1-(cyclopropylmethyl)-5-phenyl-1H-1,4-benzodiazepin-2 (3H)-one; prazepam; profadol; proheptazine; promedol; properidine; propoxyphene; N-(1-methyl-2-piperidinoethyl)-N-(2-pyridyl)propionamide; methyl {3-[4-methoxycarbonyl-4-(N-phenylpropanamido)piperidino]propanoate}; (S,S)-2-methylamino-1-phenylpropan-1-ol; pseudoephedrine, remifentanil; 5-sec-butyl-5-ethylbarbituric acid; secbutabarbital; 5-allyl-5-(1-methylbutyl)-barbituric acid; secobarbital; N-{4-methoxymethyl-1-[2-(2-thienyl)ethyl]-4-piperidyl}propionanilide; sufentanil; 7-chloro-2-hydroxymethyl-5-phenyl-1H-1,4-benzodiazepin-2(3H)-one; temazepam; 7-chloro-5-(1-cyclohexenyl)-1-methyl-1H-1,4-benzodiazepin-2(3H)-one; tetrazepam; ethyl (2-dimethylamino-1-phenyl-3-cyclohexene-1-carboxylate; cis-/trans-tilidine; tramadol; 8-chloro-6-(2-chlorophenyl)-1-methyl-4H-[1,2,4]triazolo[4,3-a][1,4]benzodiazepine; triazolam; 5-(1-methylbutyl)-5-vinylbarbituric acid; vinylbital; (1R*,2R*)-3-(3-dimethylamino-1-ethyl-2-methylpropyl)phenol; (1R,2R,4S)-2-(dimethylamino) methyl-4-(p-fluorobenzyloxy)-1-(m-methoxyphenyl) cyclohexanol.

In addition to the above compounds, abuse-susceptible active pharmaceutical ingredients also include a prodrug of any of these compounds. The term "prodrug" means a compound that is a metabolic precursor to the active pharmaceutical ingredient. This precursor is transformed in vivo to provide the active pharmaceutical ingredient which has the desired therapeutic effect.

Abuse-susceptible active pharmaceutical ingredients also include pharmaceutically acceptable salts of any of the above-mentioned compounds. The phrase "pharmaceutically acceptable salt" of a compound means a salt that is pharmaceutically acceptable and that possesses the desired pharmacological activity of the parent compound. Such salts include, for example, acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, tetramethylammonium, tetramethylammonium, methylamine, dimethylamine, trimethylamine, triethylamine, ethylamine, and the like.

The phrase "pharmaceutically acceptable" means that which is useful in preparing a pharmaceutical composition that is generally safe, non-toxic, and is not biologically or otherwise undesirable and is acceptable for human pharmaceutical use.

Furthermore, in addition to the above compounds, abuse-susceptible active pharmaceutical ingredients also include solvates of any of the above-mentioned compounds. The term "solvate" refers to an aggregate that comprises one or more molecules of abuse-susceptible active pharmaceutical ingredient with one or more molecules of a solvent. The solvent may be water, in which case the solvate may be a hydrate. Alternatively, the solvent may be an organic solvent. In one embodiment, "solvate" refers to the abuse-susceptible active pharmaceutical ingredient in its state prior to dissolution. Alternatively, the solid particles of a suspended abuse-susceptible active pharmaceutical ingredient may comprise a co-precipitated solvent.

The parenteral abuse resistant capsule of the present invention may comprise a liquid blend as part of the fill. The liquid blend comprises any pharmaceutically acceptable components so as to solubilize or miscibilize the abuse-susceptible active pharmaceutical ingredient. The components of the liquid blend may be compounds useful to prepare a pharmaceutical composition, generally safe, non-toxic and neither biologically nor otherwise undesirable, and includes compounds that are acceptable for veterinary use as well as human pharmaceutical use.

The phrase "liquid blend" means the fill of the capsule fill except for the abuse-susceptible active pharmaceutical ingredient. The liquid blend comprises selected pharmaceutically acceptable components such as a solvent, a surfactant, and a viscosity enhancer. The liquid blend may also comprise another active pharmaceutical ingredient that is not an abuse-susceptible active pharmaceutical ingredient.

One of the components of the liquid blend may be a solvent or a carrier. The fill may comprise more than one solvent. The solvent is any pharmaceutically acceptable solvent that solubilizes the active pharmaceutical ingredient and optionally other components of the liquid blend. The solvent can be hydrophilic, amphiphilic or lipophilic. Exemplary solvents include polyethylene glycol, propylene glycol, medium chain triglycerides, corn oil mono- and diglycerides, refined soybean oil, refined sesame oil, ethanol, phospholipid concentrates, poloxamers and medium chain partial glycerides.

Another component of the liquid blend of the present invention may be a surfactant. The liquid blend may comprise more than one surfactant.

Another optional component of the liquid blend of the present invention is a viscosity enhancer, or a gelling agent.

The liquid blend of the present invention balances at least three different properties: (1) solubilization of the active pharmaceutical; (2) abuse resistance; and (3) release profile. The release profile may be either immediate or extended. Other additional considerations include long term stability, and ease of processing.

In one embodiment of the present invention, the active pharmaceutical ingredient is dissolved or suspended in a lipophilic self-emulsifying drug delivery system that is not injectable with a standard insulin syringe. The solubility of the abuse-susceptible active pharmaceutical ingredient must be sufficient to solubilize a therapeutically effective amount of the abuse-susceptible active pharmaceutical ingredient. Alternatively, the abuse-susceptible active pharmaceutical ingredient may form a stable suspension.

The liquid blend of the present invention exhibits abuse resistance. In one embodiment, the abuse resistant fill provides no more than 33% of the abuse-susceptible active pharmaceutical ingredient for parenteral delivery, or no more than 25% of the abuse-susceptible active pharmaceutical ingredient for parenteral delivery, or no more than 15% of the abuse-susceptible active pharmaceutical ingredient for parenteral delivery, or no more than 10% of the abuse-susceptible active pharmaceutical ingredient for parenteral delivery, or no more than 5% of the abuse-susceptible active pharmaceutical ingredient for parenteral delivery or essentially none of the abuse-susceptible active pharmaceutical ingredient for parenteral delivery.

Parenteral abuse resistant capsule fill formulations that show acceptable solubility and that comprise colloidal anhydrous silica and a gum also exhibit abuse resistant properties. Such formulations include solvents such as medium chain triglycerides. Formulations that comprise medium chain triglycerides, colloidal anhydrous silica, and xanthan gum, also include a polysorbate surfactant.

Other solvent and surfactant combinations in the liquid blend that show abuse resistant properties when colloidal anhydrous silica and xanthan gum is present, include polyethylene glycol, and a surfactant selected from the group consisting of polyoxyl 40 hydrogenated castor oil, polysorbate surfactant, caprylocaproyl macrogol-8 glyceride, and glycerol. Examples of polyethylene glycol include macrogol 400 and macrogol 600.

Furthermore, it was found that a liquid blend comprising a phospholipid concentrate and a polysorbate surfactant also exhibits acceptable solubility and abuse resistance. The polysorbate surfactant may include polyoxyethylene (20) sorbitanmonolaurate, polyoxyethylene (20) sorbitan monopalmitate, polyoxyethylene (20) sorbitanmonostearate, and/or polyoxyethylene (20) sorbitanmonooleate. Examples of phospholipid concentrates include Phosal 50 PG, and Lipoid PPL 600.

Yet another combination of liquid blend components that exhibit solubility and abuse resistance is a liquid blend comprising polyethylene glycol, caprylocaproyl macrogol-8 glycerides, glycerol, and a viscosity enhancer. The viscosity enhancer may be a mixture of colloidal anhydrous silica and a gum.

In one aspect of the present invention an abuse resistant liquid suitable for encapsulation in a capsule, comprises: (a) an abuse-susceptible active pharmaceutical ingredient selected from the group consisting of opiates, opioids, tranquilizers, stimulants and narcotics; (b) a viscosity enhancer or an ion exchange resin; and (c) a surfactant; such that a mixture of about 250 milligrams to about 1000 milligrams of the abuse resistant liquid with 5 milliliters of water at the mixture's boiling point forms a viscous phase from which less than 33% of the active pharmaceutical ingredient is recovered by a 25 millimeter needle having an inner diameter of 0.60 millimeters. In particular embodiments, mixtures of about 250 mg, about 500 mg, about 750 mg or about 1000 mg of the abuse resistant liquid with 5 ml of water at the mixture's boiling point form the viscous phase.

As discussed in the experimental section below, the 1000 mg mixture has an excellent correlation to the tamper resistance characteristics of the capsule of fill weight of about 900 to 950 milligrams. All liquid mixtures, which fulfilled the tamper resistance requirement also showed good dispersability, at amounts of 250 mg and 1000 mg.

The term "parenteral" as used in the phrase "parenteral abuse resistant capsule" means that the abuse-susceptible active pharmaceutical ingredient is introduced into the human body via a parenteral route. The term "parenteral" includes introduction of the abuse-susceptible active pharmaceutical ingredient into the body via injection. Such an injection may be intradermal, subcutaneous, transdermal, intravenous, or intramuscular.

The phrase "abuse resistant" when referring to the parenteral abuse resistant capsule, means that it is difficult for an average drug abuser to take the necessary steps to isolate the abuse-susceptible active pharmaceutical ingredient from the capsule to the level necessary to introduce the abuse-susceptible active pharmaceutical ingredient parenterally. The degree of difficulty in obtaining the abuse-susceptible active pharmaceutical ingredient ranges from impossibility (0% of the abuse-susceptible active pharmaceutical ingredient is delivered parenterally) to challenging (33% of the abuse-susceptible active pharmaceutical ingredient is delivered parenterally).

The parenteral abuse resistant liquid may comprise either a viscosity enhancer or an ion exchange resin.

The viscosity enhancer, also known as a gelling agent, is selected from any pharmaceutically acceptable viscosity enhancers. The viscosity enhancer may comply with the pharmaceutical compendial standards as listed below. The fill may comprise more than one viscosity enhancer. Exemplary viscosity enhancers include gums such as acacia, agar, tragacanth, guar gum, xanthan gum, locust bean gum, tara gum, karaya, gellan gum, welan gum, and rhamsan gum.

An alternative to the viscosity enhancer is an ion exchange resin. Although the ion exchange resins generally have thickening effects on the liquid, not all ion exchange resins exhibit such a property. Examples of the ion exchange resin include polacrilex resin, sodium polystyrene sulfonate, potassium polyacrilin, and colestyramine resin. These exemplary ion exchange resins are commercially available as Amberlite® IRP64, Amberlite® IRP69, Amberlite® IRP88, and Duolite AP 143/1093. (AMBERLITE and DUOLITE are registered trademarks of Rohm & Haas Company, its subsidiaries or their successors).

A third component of the parenteral abuse resistant liquid may be a surfactant. The parenteral abuse resistant liquid may comprise more than one surfactant. The surfactant is selected from any pharmaceutically acceptable surfactants. The surfactant may comply with the pharmaceutical compendial standards as listed herein.

Exemplary surfactants include polysorbate 20, Tween® 20, polysorbate 80, Tween® 80, macrogolglycerol hydroxystearate, Cremophor® RH 40, macrogolglycerol ricinoleate, Cremophor® EL, glycerolmonooleate 40, Peceol™, macrogolglycerol linoleate, Labrafil M 2125 CS, propylene glycol monolaurate FCC, Lauroglycol FCC, polyglycerol-6-dioleate, polyglycerol-3-dioleate, Plurol® Oleique, propylene glycol monocaprylate, Capryol® 90, sorbitanmonolaurate, Span® 20, sorbitanmonooleate, Span® 80, Vitamin E-polyethylenglycol-succinate, caprylocaproyl macrogol-8 glycerides, Labrasol®, macrogol-32-glycerol-laurate, Gelucire 44/14, glycerylmonocaprate/caprylate, Capmul MCM.

In one embodiment, the parenteral abuse resistant liquid comprises a polysorbate surfactant. Examples of the polysorbate surfactant include polysorbate 80, polysorbate 20, polyoxyethylene (20) sorbitane monolaurate, polyoxyethylene (20) sorbitane monopalmitate, polyoxyethylene (20) sorbitane monostearate, and polyoxyethylene (20) sorbitane monooleate.

In another embodiment, the parenteral abuse resistant liquid comprises a surfactant selected from the group consisting of macrogolglycerol ricinoleate, macrogolglycerol hydroxystearate and caprylocaproylmacrogol-8-glycerides.

Polysorbate 20 also known as, or similar to, or related to, polyoxyethylene(20) sorbitan monolaurate or sorbitan monolaurate, that is typically sold under brand names such as Alkest® TW 20 and Tween® 20. Polysorbate 20 is a mixture of partial esters of fatty acids, mainly lauric acid, with sorbitol and its anhydrides ethoxylated with approximately 20 moles of ethylene oxide for each mole of sorbitol and sorbitol anhydrides. Polysorbate 20 is a polysorbate surfactant with stability and relatively low toxicity. CAS Number 9005-64-5.

Polysorbate 80, also known as, or similar to, or related to, polyethylene glycol sorbitan monooleate, is a common name for polyoxyethylene(20) sorbitan monooleate, that is typically sold under brand names such as Alkest TW 80 and Tween® 80. Polysorbate 80 is a mixture of partial esters of fatty acids, mainly oleic acid, with sorbitol and its anhydrides ethoxylated with approximately 20 moles of ethylene oxide for each mole of sorbitol and sorbitol anhydrides. Polysorbate 80 is a nonionic surfactant and emulsifier derived from polyethoxylated sorbitan and oleic acid. CAS Number 9005-65-6.

Macrogolglycerol hydroxystearate also known as, or similar to, or related to, PEG-40 castor oil, polyoxyl 40 hydrogenated castor oil, and is generally sold under brand names such as Cremophor® RH 40, or Kolliphor® RH 40. Macrogolglycerol hydroxystearate contains mainly trihydroxystearyl glycerol ethoxylated with 7 to 60 molecules of ethylene oxide (nominal value), with small amounts of macrogol hydroxystearate and of the corresponding free glycols. It results from the reaction of hydrogenated castor oil with ethylene oxide. CAS Number 61788-85-0.

Macrogolglycerol ricinoleate, also known as, or similar to, or related to, as PEG-35 castor oil, polyoxyl 35 hydrogenated castor oil, or polyoxyl-35 castor oil, and is generally sold under brand names such as Kolliphor EL, and Cremophor EL. Macrogolglycerol ricinoleate contains mainly ricinoleyl glycerol ethoxylated with 30 to 50 molecules of ethylene oxide (nominal value), with small amounts of macrogol ricinoleate and of the corresponding free glycols. It results from the reaction of castor oil with ethylene oxide. CAS Number 61791-12-6.

Glycerol monooleate 40, also known as, or similar to, or related to, 1,3-dihydroxy-2-propanyl (9Z)-9-octadecenoate, 2-oleoylglycerol, Peceol™. Formula: $CH_3(CH_2)_7CH=CH(CH_2)_7COO-CH_2CHOHCH_2OH$, CAS Numbers 111-03-5 and 3443-84-3.

Labrafil M 2125 CS, also known as, or similar to, or related to, linoleoyl macrogol-6 glycerides, linoleoyl polyoxyl-6 glycerides, corn oil PEG-6 esters, is a water dispersible surfactant composed of well-characterized PEG-esters and a glycerides fraction.

Propylene glycol monolaurate EP/NF, also known as, or similar to, or related to, Lauroglycol™ FCC, is a mixture of the propylene glycol mono- and di-esters of lauric acid. It is a water insoluble surfactant for use in self emulsifying systems to obtain a coarse dispersion, i.e., emulsion (SEDDS) or a fine dispersion, i.e., microemulsion (SMEDDS). CAS number 27194-74-7. Propylene glycol monolaurate, as used throughout this document, may be a Type I propylene glycol monolaurate (comprising 45.0% to 70.0% of monoesters and 30.0% to 55.0% of diesters), or Type II propylene glycol monolaurate (comprising minimum 90.0% of monoesters and maximum 10.0% of diesters).

Polyglycerol-6-dioleate, also known as, or similar to, or related to, homohexamer di[(9Z)-9-octadecenoate] 1,2,3-propanetriol, hexaglyceril dioleate, is a diester of oleic acid and a glycerin polymer containing an average of 6 glycerin units. It is available, for example, from Gattefossé under the trademark Plurol Stearique WL 1009. CAS number 76009-37-5.

Polyglyceryl-3-oleate, also known as, or similar to, or related to, polyglyceryl-3 dioleate, triglyceryl dioleate, polyglycerol oleate, polyglyceryl oleate, triglyceryl monooleate, is a diester of oleic acid and a glycerin polymer containing an average of 3 glycerin units, available from under the trademark Plurol® Oleique CC 497. CAS number 9007-48-1.

Propylene glycol monocaprylate, also known as, or similar to, or related to, 1,2-propanediol monocaprylate, Capryol™ 90, and propylene glycol caprylate, is a water insoluble surfactant for use in self emulsifying systems to obtain a coarse dispersion, i.e., emulsion (SEDDS) or a fine dispersion, i.e., microemulsion (SMEDDS). CAS numbers 31565-12-5, 132721-32-5.

Sorbitan monostearate, also known as, or similar to, or related to, octadecanoic acid [2-[(2R,3S,4R)-3,4-dihydroxy-2-tetrahydrofuranyl]-2-hydroxyethyl] ester, is an ester of sorbitan (a sorbitol derivative) and stearic acid and is sometimes referred to as a synthetic wax. Sorbitan monostearate is usually obtained by partial esterification of sorbitol and its mono- and di-anhydrides with stearic acid 50, or stearic acid 70. It is frequently used as an emulsifier to keep water and oils mixed. CAS number: 1338-41-6.

Sorbitan monolaurate, also known as, or similar to, or related to, sorbitan monododecanoate, dodecanoic acid [2-[(2R,3R,4S)-3,4-dihydroxy-2-tetrahydrofuranyl]-2-hydroxyethyl]ester, and Span® 20. CAS Number 1338-39-2.

Sorbitan monooleate, also known as, or similar to, or related to, Span 80, is a mixture of the partial esters of sorbitol and its mono- and dianhydrides with edible oleic acid. The constituent in greatest abundance is 1,4-sorbitan monooleate, with a lesser abundance of isosorbide monooleate, sorbitan dioleate and sorbitan trioleate. CAS Number 1338-43-8.

The surfactant may also be a phosphatidylcholine concentrate. One of the advantages of using phosphatidylcholine concentrate as a surfactant in the parenteral abuse resistant liquid, is that it is generally not necessary to add a stabilizer to the liquid.

A stabilizer can also be used in the parenteral abuse resistant liquid. Examples of such stabilizers include a colloidal anhydrous silica, hard fat and a glycerolester of long chain fatty acid.

For formulations comprising hydrophilic carriers or hydrophilic solvents, the data shows that colloidal anhydrous silica is generally preferred. Examples of a hydrophilic carrier or a hydrophilic solvent include macrogol 400, macrogol 600, macrogol 1500, propylene glycol, glycerol and water.

For formulations comprising lipophilic carriers or lipophilic solvents, the data shows that hard fat or glycelester of long chain fatty acid is generally preferred. Examples of a lipophilic carrier include medium chain triglycerides, medium chain partial glycerides, and a vegetable oil.

A vegetable oil is a triglyceride extracted from a plant. Examples of suitable vegetable oils include sesame oil, corn oil, sunflower oil, safflower oil and olive oil. Further, vegetable oils also include coconut oil, cottonseed oil, palm oil, peanut oil, rapeseed oil, soybean oil, and mustard oil.

The parenteral abuse resistant liquid may optionally also comprise any pharmaceutically acceptable components so as to solubilize, miscibilize, or suspend the abuse-susceptible active pharmaceutical ingredient. Such a component is a carrier, generally considered a solvent. The parenteral abuse resistant liquid may comprise more than one carrier. The carrier is any pharmaceutically acceptable carrier that solubilizes the active pharmaceutical ingredient and the other ingredients of the fill composition.

Within the scope of the present invention, some compositions act as both carriers and surfactants. Thus, the parenteral abuse resistant liquid may consist only of an abuse-susceptible active pharmaceutical ingredient; a viscosity enhancer or an ion exchange resin; and a surfactant.

The term "water" as used herein means purified water as defined by compendial standards, or any water which is appropriate for use in pharmaceutical formulations.

The carrier may comply with the pharmaceutical compendial standards. Compendial standards include those listed in a reference, such as the European Pharmacopoeia, Österreichisches Arzneibuch, Farmacopéia Brasileira, Pharmacopoeia of the People's Republic of China, Český lékopis, Pharmacopoea Bohemica, The Czech Pharmacopoeia, Egyptian Pharmacopoeia, Pharmacopée française, Deutsches Arzneibuch, Deutscher Arzneimittel Codex, Neues Rezeptur Formularium, Greek Pharmacopoeia, Pharmacopoea Hungarica, Indian Pharmacopoeia, Farmakope Indonesia, Iranian Pharmacopoeia, Farmacopea Ufficiale della Repubblica Italiana, The Japanese Pharmacopoeia, The Korean Pharmacopoeia, Farmacopea de los Estados Unidos Mexicanos, Farmakopea Polska, Farmacopeia Portuguesa, Farmacopeea Romana, State Pharmacopoeia of the Russian Federation, Pharmacopoea Slovaca, Slovenský liekopis, Real Farmacopea Española, Pharmacopoea Helvetica, Thai Pharmacopoeia, The State Pharmacopoeia of the Ukraine, British Pharmacopoeia, The United States Pharmacopeia, The National Formulary, Pharmacopoeia Vietnamica, Pharmacopoea Jugoslavica, African Pharmacopoeia, and The International Pharmacopoeia.

The carrier of the present invention may be hydrophilic, amphiphilic, or lipophilic. Exemplary solvents include polyethylene glycol, propylene glycol, medium chain triglycerides, corn oil mono- and diglycerides, poloxamers, refined soybean oil, refined sesame oil, ethanol, phospholipid concentrates, and medium chain partial glycerides.

Examples of the abuse resistant liquid of present invention include a hydrophilic formulation, lipophilic formulation, and amphiphilic phospholipid formulation.

An example of a parenteral abuse resistant liquid comprises an active pharmaceutical ingredient and (i) 40 to 60 wt % macrogol 600; (ii) 15 to 25 wt % caprylocaproylmacrogol-8 glycerides; (iii) 3 to 10 wt % colloidal anhydrous silica; (iv) 3 to 6 wt % glycerol; (v) 0.5 to 10 wt % water; and (vi) 2 to 20 wt % ion exchange resin or 0.2 to 0.5 wt % xanthan gum, wherein the weight percent are calculated with respect to the weight of the parenteral abuse resistant liquid.

Another example of a parenteral abuse resistant liquid comprises an active pharmaceutical ingredient and (i) 40 to 70 wt % hard fat; (ii) 4 to 20 wt % glycerol stearate or glycerol dibehenate; (iii) 10 to 70 wt % medium chain triglycerides; (iv) 4 to 50 wt % polysorbate 80; (v) 4 to 15 wt % sorbitol monolaurate; (vi) 3 to 10 wt % macrogolglycerol ricinoleate or macrogolglycerol hydroxystearate; (vii) 1 to 5 wt % colloidal anhydrous silica; and (viii) 2 to 5 wt % xanthan gum; wherein the weight percent are calculated with respect to the weight of the parenteral abuse resistant liquid.

Yet another example of a parenteral abuse resistant liquid comprises an active pharmaceutical ingredient and (i) 50 to 80 wt % phosphatidylcholine concentrate; (ii) 15 to 25 w % caprylocaproylmacrogol 8 glycerides; (iii) 5 to 10 wt % polysorbate 80; (iv) 0.2 to 5 wt % xanthan gum; (v) 1 to 10 wt % colloidal anhydrous silica; and (vi) 4 to 10 wt % water; wherein the weight percent are calculated with respect to the weight of the parenteral abuse resistant liquid. The phosphatidylchholine concentrate comprises more than 50 wt % phosphatidylcholine, less than 6 wt % lysophosphatidylcholine, and about 35 wt % of polypropylene glycol.

The parenteral abuse resistant liquid of the present invention balances at least three competing properties: (1) solubilization; (2) abuse resistance; and (3) its release profile. Other additional considerations include long term stability, and ease of processing.

The solubility of the abuse-susceptible active pharmaceutical ingredient may be determined by mixing equivalent of 25% of the therapeutically effective amount of the abuse-susceptible active pharmaceutical ingredient in the liquid blend. After stirring for 18 hours at 20° C. to 25° C., additional 25% of the abuse-susceptible active pharmaceutical ingredient is added. This last step is repeated until the saturation solubility is reached.

The liquid blend of the present invention exhibits abuse resistance. In one embodiment of the invention, the abuse resistant fill provides no more than 33% of the abuse-susceptible active pharmaceutical ingredient for parenteral delivery. To test the abuse resistance, a weighed aliquot corresponding to the amount of filling material in a capsule is transferred to a metal tablespoon and mixed with 5 mL of purified water to create a mixture. This mixture is stirred with a spatula and then briefly heated to boiling over an open flame. After allowing the mixture to cool for about 1 minute, the mixture is filtered through a cigarette filter. The filtrate is then aspirated into a 5 mL disposable syringe equipped with a 20 gauge, 25 mm long needle.

Another aspect of the present invention is a parenteral abuse resistant liquid that is resistant to alcohol dose dumping. Such a liquid meets the requirements on alcohol dose dumping resistance set by the European Medicines Agency or the Food and Drug Administration on selected new drug products.

In order to ascertain if simultaneous intake of alcohol and an abuse resistant softgel has an influence on the immediate release dissolution profile of the active pharmaceutical ingredient, the in vitro dissolution of selected batches of capsules was tested by exposing such capsules to (a) 5 hours 0.1N HCl with 40% absolute ethanol; or (b) 5 hours in a pH 4.6 buffer with 40% absolute ethanol; or (c) 5 hours in a pH buffer 6.8 with 40% absolute ethanol.

The immediate release in vitro dissolution profiles of Formulation A (described in detail below) over five hours in the three different dissolution media are comparable, and are not influenced in presence of 40% ethanol. Within 30 minutes at least 98% the active pharmaceutical ingredient is released in 0.1 N HCl, 96.3% in the pH 4.6 buffer and 91% in the pH 6.8 buffer. These in vitro dissolution data indicate that no in vivo dose dumping occurs in case of simultaneous intake of alcohol and the abuse resistant dosage form.

Another aspect of the present invention is a parenteral abuse resistant liquid that is resistant to solvent, acidic or aqueous extraction. In order to ascertain the resistance to solvent extraction, samples of Formulations A and B (described in detail below) were mixed thoroughly with non-polar solvents, and extracted for either 6 or 24 hours. Non-polar solvents included xylene, toluene, and a 40:60 mixture of petroleum and benzene. After decanting the non-polar solvent, the residue was not solid but a turbid slurry. Mixing and boiling the residue did not result in a solid but also in a slurry that spattered while boiling. This behavior is indicative or suggestive of resistance to solvent extraction.

In order to ascertain the resistance to aqueous and acidic extraction, the fill mass of 10 capsules was mixed with different amounts of purified water (5 mL/caps. and 10 mL/caps.) and extracted for 1, 3 or 5 days. Further, the fill mass of 10 capsules was mixed with 20 mL of methanol and was extracted for 3 days.

The fill mass of 10 capsules of Formulation A or Formulation B was mixed with 20 mL of 0.1 N hydrochloric acid and extracted for one day. Comparison solutions of Pseudoephedrine HCl (labeled as API in the table below) were prepared. After an extraction of the formulation/solvent mixture, the mixtures were centrifugated and the assay of pseudoephedrine HCl was analyzed by HPLC. Even after centrifugation the solutions were turbid. The results of the extraction are presented in the table below. The results were normalized to a capsule containing 1164.8 mg of pseudoephedrine HCl.

| Sample | Formulation | Extraction time | Solvent | Calculated Mass of recoverable Pseudoephedrine HCl |
|---|---|---|---|---|
| 1 | A | 3 days | 5 mL water/capsule | 94.8 mg |
| 2 | A | 3 days | 10 mL water/capsule | 83.6 mg |
| 3 | B | 3 days | 5 mL water/capsule | 107.2 mgl |
| 4 | B | 3 days | 10 mL water/capsule | 89.4 mg |
| 5 | API | 3 days | 50 mL water | 1243.7 mg |
| 6 | A | 5 days | 5 mL water/capsule | 105.0 mg |
| 7 | A | 5 days | 10 mL water/capsule | 100.5 mg |
| 8 | B | 5 days | 5 mL water/capsule | 106.9 mg |
| 9 | B | 5 days | 10 mL water/capsule | 112.5 mg |
| 10 | API | 5 days | 50 mL water | 1227.7 mg |
| 11 | A | 3 days | 20 mL methanol | 847.3 mg |
| 12 | B | 3 days | 20 mL methanol | 870.3 mg |
| 13 | API | 3 days | 20 mL methanol | 1165.6 mg |
| 14 | A | 1 day | 5 mL water/capsule | 94.5 mg |
| 15 | A | 1 day | 10 mL water/capsule | 94.1 mg |
| 16 | B | 1 day | 5 mL water/capsule | 97.6 mg |
| 17 | B | 1 day | 10 mL water/capsule | 71.6 mg |
| 18 | API | 1 day | 50 mL water | 1026.0 mg |
| 19 | B | 1 day | 20 mL HCl 0.1 mol/L with neutralisation | 898.6 mg |

-continued

| Sample | Formulation | Extraction time | Solvent | Calculated Mass of recoverable Pseudoephedrine HCl |
|---|---|---|---|---|
| 20 | API | 1 day | 20 mL HCl 0.1 mol/L with neutralisation | 1197.3 mg |
| 21 | B | 1 day | 20 mL HCl 0.1 mol/L without neutralisation | 493.9 mg |
| 22 | API | 1 day | 20 mL HCl 0.1 mol/L without neutralisation | 1054.7 mg |

The data in the above table indicates that aqueous extraction of the active pharmaceutical ingredient from either Formulation A or B yielded poor recovery of the active pharmaceutical ingredient, indicating that liquid is resistant to solvent, acidic or aqueous extraction. It also appears that the resistance is independent of the volume of water used to extract the liquid, and of the extraction time.

The parenteral abuse resistant liquid of the present invention is applicable for use in immediate release formulations or in extended release formulations. Usually, such formulations also include a capsule shell, and are delivered in a capsule.

The phrase "extended release" refers to a formulation designed to release a therapeutically effective amount of drug or other active agent such as a polypeptide or a synthetic compound over an extended period of time, with the result being a reduction in the number of treatments necessary to achieve the desired therapeutic effect. An example of the extended release capsule is a capsule that releases about 90% of the active pharmaceutical ingredient in the gastrointestinal tract throughout a period of about 12 hours after administration.

The phrase "extended release" also includes formulations that exhibit zero order release (see discussion of Formulation E below), and sustained release formulations. See, for example, G. M. Jantzen, J. R. Robinson *Sustained-and Controlled-Release Drug Delivery Systems* In Modern Pharmaceutics, vol. 72, Marcel Dekker Inc. (1995).

The parenteral abuse resistant liquid formulations that show acceptable solubility properties and comprise a colloidal anhydrous silica and a gum exhibit abuse resistant properties. Such formulations include solvents such as medium chain triglycerides. Formulations that comprise medium chain triglycerides, colloidal anhydrous silica, and xanthan gum, also include a polysorbate surfactant.

The polysorbate surfactants in the above formulation that exhibits the abuse resistant properties may include polyoxyethylene (20) sorbitanmonolaurate, polyoxyethylene (20) sorbitan monopalmitate, polyoxyethylene (20) sorbitanmonostearate, and polyoxyethylene (20) sorbitanmonooleate.

The formulations Examples 14, 16 to 18 comprise medium chain triglycerides (26.4%, 27.3%, 27.9% and 28.2%, respectively), polysorbate 80 (49.2%, 50.9%, 52.1%, and 52.7%), Span 20 (12.3%, 12.7%, 13.0%, and 13.2%), colloidal anhydrous silica (4.5%, 3.5%), and xanthan gum (4.5%, 2.7%). These compositions are yellowish, homogeneous, liquid suspensions, which formed a gel and non-stable bubbles at boiling with water. 250 and 1000 g of the fill could hardly be drawn up in the syringe and formed of a milky foam. Both formulations showed good dispersability after disintegration of capsules (4.5 minutes). Approximately 80% of the fill was dissolved after 20 to 25 minutes and 100% after approx. 30 minutes.

Other solvent and surfactant combinations in the liquid blend that show abuse resistant properties when colloidal anhydrous silica and xanthan gum is present, include polyethylene glycol, and a surfactant selected from the group consisting of polyoxyl 40 hydrogenated castor oil, polysorbate surfactant, caprylocaproyl macrogol-8 glyceride, and glycerol. Examples of polyethylene glycol include macrogol 400 and macrogol 600.

Caprylocaproyl macrogol-8 glycerides (Labrasol) in Examples Nos. 30, 31, and 32 and colloidal anhydrous silica/xanthan gum as gelling agents gave yellowish homogeneous suspensions, which formed a gel and a partially persisting foam at boiling in the water. The solution was not syringeable but the dispersibility of the gel was bad due to formation of a compact mass after 6 minutes in the dispersion medium.

Abuse resistant properties were also observed by replacing macrogol 400 (see Example 35) by macrogol 600 and xanthan gum. An intensive frothing milky emulsion resulted after boiling with water, which was not syringeable. Both selected formulations of Examples 35 and 36 were easily dispersible in 0.1 N HCl at 100 rpm. 80% of the fill were dissolved after 20 minutes and 100% within 30 minutes.

Furthermore, it was found that the liquid blend comprising a phospholipid concentrate and a polysorbate or caprylocaproyl macrgol glyceride surfactant also exhibited acceptable solubility and abuse resistance. The polysorbate surfactants in the above formulation that exhibited the abuse resistant properties include polyoxyethylene (20) sorbitanmonolaurate, polyoxyethylene (20) sorbitan monopalmitate, polyoxyethylene (20) sorbitanmonostearate, and polyoxyethylene(20) sorbitanmonooleate. Examples of phospholipid concentrates include Phosal 50 PG, and Lipoid PPL 600. For selected formulations, the use of a viscosity enhancer (colloidal anhydrous silica 0.5 to 1.5 wt %) was found to be necessary in formulations containing the abuse-susceptible active pharmaceutical ingredient in order to achieve tamper resistance.

Yet another combination of liquid blend components that exhibit solubility and abuse resistance is liquid blend comprising polyethylene glycol, caprylocaproyl macrogol-8 glycerides, glycerol, a viscosity enhancer, and either a gum or an ion-exchange resin. The viscosity enhancer may be a mixture of colloidal anhydrous silica and a gum.

Two examples of formulations that exhibit the desired properties include Pseudoephedrine HCl as the abuse-susceptible active pharmaceutical ingredient. One of the formulations comprises xanthan gum (Formulation B), the other pharmaceutical grade ion exchange resin Amberlite IRP64 (Formulation A).

These formulations comprise about 50% to 60% polyethylene glycol, 15% to 20% caprylocaproyl macrogol-8 glycerides, 3 to 6% colloidal anhydrous silica, 3 to 6% glycerol, 1% to 2% water.

Formulation A comprises macrogol 600 EP (479.02 mg/capsule, 51.0% of fill), caprylocaproyl macrogol-8 glycerides EP (160.00 mg, 17.0%), Colloidal anhydrous Silica EP (45.00 mg, 4.8%), Glycerol, anhydrous EP (47.00 mg, 5.0%), Water, purified, EP (12.50 mg, 1.3%), Amberlite IRP64 (80.00 mg, 8.5%) and Pseudoephedrine HCl (116.48 mg, 12.4%).

Formulation B comprises macrogol 600 EP (554.2 mg/capsule, 58.3% of fill), caprylocaproyl macrogol-8 glycerides EP (175.00 mg, 18.4%), colloidal anhydrous silica EP (40.00 mg, 4.2%), anhydrous glycerol EP (47.00 mg, 4.9%), purified water, EP (12.50 mg, 1.3%), xanthan gum (5.00 mg, 0.5%) and pseudoephedrine HCl (116.48 mg, 12.3%).

Macrogol 600 is hydrophilic solvent for the water soluble drugs. Caprylocaproylmacrogol 8 glycerides are hydrophilic surfactants (HLB 14) and solvents that improve dissolution and bioavailability, and cause bubbling at boiling of the capsule fill with water. Colloidal anhydrous silica is a viscosity enhancer in order to stabilize the hydrophile fill suspension. Glycerol is a plasticizer in the fill to reduce migration from the shell to the fill. Water increases drug solubility, reduces gelling agent concentration and has a positive effect on immediate release dissolution properties.

With respect to xanthan gum in formulation B, this hydrogelling agent is suspended in the capsule fill, but at boiling of the capsule fill with hot water, it may form a highly viscous gel. This gel formation reduces syringability and injectability.

With respect to Amberlite IRP64 in formulation A, the HCl salt of the quarternary ammonium ion of the active substance pseudoephedrine HCl may create a drug-ion exchange complex with the weak acidic catonic resin (—COOH group) on Amberlite IRP64. This ion pair complex is stable in the formulation, but is immediately released in the stomach environment, as the —COOH group of the resin has a high affinity to the $H^+$ ions present in the stomach. In addition to the fast release of the abuse-susceptible active pharmaceutical ingredient in 0.1 N HCl, an increase of the viscosity at boiling of the formulations containing the Polyacrilex resin was achieved.

The following results have been obtained for in vitro dissolution and the abuse resistance test (syringability). The immediate release dissolution (in 0.1 N HCl, at 75 rpm) showed that more than 95% of the active pharmaceutical ingredient in either of the formulations was released within 30 minutes. Both formulations showed that not more than 33% of the pharmaceutically active ingredient was detectable in syringe after boiling of the capsule fill with 5 mL water. For formulation B only about 9.8% of the pseudoephedrine was recovered, and for formulation A only about 12.2% of the pseudoephedrine was recovered.

Three further examples of formulations that exhibit the desired properties also included pseudoephedrine HCl as the abuse-susceptible active pharmaceutical ingredient. Two of the immediate release formulations contained alternative ion exchange resins. Formulation C comprised Amberlite IRP69, and Formulation D contained Duolite AP143/1093. The extended release formulation E comprised Phosal PG in combination with caprylocaproyl macrogol-8 glycerides and xanthan gum.

Formulations C and D contained about 50% to 60% polyethylene glycol, 15% to 20% caprylocaproyl macrogol-8 glycerides, 3% to 6% colloidal anhydrous silica, 3% to 6% glycerol, and 1% to 2% water.

Formulation C contained macrogol 600 EP (479.02 mg/capsule, 51.0% of fill), caprylocaproyl macrogol-8 glycerides EP (160.00 mg, 17.0%), colloidal anhydrous silica EP (85.00 mg, 9.6%), anhydrous glycerol EP (47.00 mg, 5.0%), purified water, EP (12.50 mg, 1.3%), Amberlite IRP69 (40.00 mg, 4.3%) and pseudoephedrine HCl (116.48 mg, 12.4%).

Formulation D contained macrogol 600 EP (459.02 mg/capsule, 48.8% of fill), caprylocaproyl macrogol-8 glycerides EP (160.00 mg, 17.0%), colloidal anhydrous silica EP (65.00 mg, 6.9%), anhydrous glycerol EP (47.00 mg, 5.0%), purified water EP (12.50 mg, 1.3%), Duolite AP 143/1093 (80.00 mg, 8.5%), and pseudoephedrine HCl (116.48 mg, 12.4%).

The capsule shell contained glycerol 85% EP 112.15 mg (range 103.18 mg to 121.12 mg), partially hydrated dry substance of sorbitol 31.34 mg (28.83 mg to 33.85 mg), gelatin 160 bloom EP NF (bovine, kosher, Halal) 247.96 mg (228.12 to 267.80 mg).

Amberlite IRP69, sodium polystyrene sulfonate USP, an insoluble sodium salt of a strong acid and strong base. The mobile exchangeable cation is sodium, which can be exchanged by cationic (basic) species independent of pH. The resin binds the active ingredient onto an insoluble polymeric matrix. The active pharmaceutical ingredient is released from the resin in vivo in the gastrointestinal tract with high electrolyte concentrations.

Duolite AP 143/1093 resin, colestyramine resin, is an insoluble, strongly basic, anion exchange resin and in the chloride form suitable as carrier for acidic, anionic drug substances. The ability to exchange anions from this styrene/divinylbenzene copolymer with an quarternary ammonium functionality is also largely independent of pH. In addition, colestyramine resin has adsorbative pH independent properties.

The following results of relevant parameters of in vitro dissolution and the abuse resistance test ("syringeability") have been obtained. The immediate release dissolution (in 0.1 N HCl, at 75 rpm) showed that more than 90% of the active pharmaceutical ingredient in either of the formulations was dissolved and released within 30 minutes. Both formulations showed that not more than 33% of the active pharmaceutical ingredient was detected in a syringe after boiling of the capsule fill with 5 mL water. For formulation C, only about 10.2% of the pseudoephedrine was recovered, and for formulation D, only about 12.1% of the pseudoephedrine was recovered.

Formulation E contained about 50 to 80 wt % phosphatidylcholine concentrate, 15 to 25 wt % caprylocaproyl macrogol-8 glycerides, 0.2 to 5% xanthan gum, and 4 to 10 wt % water.

Formulation F contained Phosal 50 PG (537.02 mg/capsule, 56.5% of fill), caprylocaproyl macrogol-8 glycerides EP (190.00 mg, 20.0%), purified water EP (66.50 mg, 7.0%), xanthan gum EP (40.00 mg, 4.2%) and pseudoephedrine HCl (116.48 mg, 12.3%).

The capsule shell contained propylene glycol 85% EP 78.73 mg (72.43 mg to 85.03 mg), glycerol 85% 35.64 mg (32.62 mg to 38.80 mg); gelatin 195 bloom EP NF (bovine) 304.67 mg (280.30 mg to 329.04 mg); titanium dioxide EP USP 0.96 mg (0.88 mg to 1.037 mg); red iron oxide 0.064 mg (0.059 mg to 0.069 mg), yellow iron oxide 0.90 mg (0.83 mg to 0.97 mg).

The phospholipid concentrate also exhibits gelling in presence of water. Similar to the xanthan gum in formulation B, the phospholipid concentrate may be partly dissolved in the capsule fill, and at boiling of the capsule fill with hot water it forms a highly viscous gel. Both the phospholipid concentrate and xanthan gum are susceptible to bubbling on heating with water resulting in formation of a very stable foam.

The active pharmaceutical ingredient is dissolved in the mixture of purified water, Phosal 50 PG and caprylocaproyl-macrogol glycerides. The highly concentrated xanthan gum (4.2%) forms a hydrogel with the liquid blend in the capsule that provides extended release of the active pharmaceutical ingredient over 12 hours after its administration.

The following results of the in vitro dissolution and abuse resistance test have been obtained. The extended release dissolution over a total of 12 hours (2 hours in 0.1 N HCl, 2 hours in a pH 4.6 buffer, and 8 hours in a pH 6.8 buffer) showed an extended release zero order dissolution profile. Over a period of 12 hours more than 97% of the pseudoephedrine HCl was released in the dissolution medium. Not more than 2.2% the pseudoephedrine HCl was detectable in a syringe after boiling of the capsule fill with 5 mL water.

Another aspect of the present invention is a parenteral abuse resistant capsule comprising any of the abuse resistant liquids as described above.

The capsule is an oral dosage form for delivery of an active pharmaceutical ingredient. The capsule comprises at least a shell (also known as a "capsule shell") and a fill (also known as a "capsule fill"). The shell completely surrounds the fill so as hold the fill. The composition of the capsule shell is such that it is compatible with the fill.

The parenteral abuse resistant capsule comprises a shell which may be comprised of any suitable material that is known to form a capsule. In one embodiment of the present invention, the capsule is a hard gelatin capsule. The hard gelatin capsule may be formed and filled in any manner known in the art. In one embodiment, the hard gelatin capsule is exclusively designed to optimize liquid filling.

In another embodiment, the capsule is a soft capsule, such as a soft gelatin capsule. The shell may be formed from a combination of gelatin, water, and a plasticiser. Type A gelatin, with an isoionic point of 7 to 9, is derived from collagen with acid pretreatment. Type B gelatin, with an isoionic point of 4.8 to 5.2, is the result of alkaline pretreatment of the collagen. Type A gelatin, Type B gelatin or mixtures thereof may be used to form the capsule shell.

Examples of plasticizers include propylene glycol, glycerol, glycerin, sorbitol, and Anidrisorb.

The shell may be composed of a material that does not include gelatin. Exemplary components of non-gelatin capsules include modified starch, modified cellulose, substances derived from seaweed, and carrageenan. In one embodiment, the shell is based on a modified starch and carrageenan. An example of such a shell is the OptiShell®, which is a shell derived from plant polysaccharides that are suited for the encapsulation of higher melting point fill formulations, and for soft capsules containing semi-solid matrices for modified release of poorly soluble and/or poorly permeable drug compounds. The shell may be composed of substances that meet the ethical, cultural, dietary, or religious restrictions of the target consumer of the capsule such as the Kosher standards or the Halal standards.

An exemplary capsule shell comprises glycerol 85% EP (106.43 mg, range 97.92 mg to 114.94 mg), dry substance of partially hydrogenated sorbitol (Anidrisorb 85/70, 30.87 mg, range 28.40 mg to 33.34 mg); gelatin 160 bloom. EP NF (bovine, kosher, Halal, 244.17 mg, range 224.64 mg to 263.70 mg).

An exemplary gelatin free shell comprises 142.29 mg (range of 128.06 mg to 156.518 mg) modified maize starch; 46.06 mg (41.46 mg to 50.67 mg) carrageenan, 151.64 mg (136.48 mg to 166.80 mg) partially hydrated dry substance of sorbitol, 4.17 mg (3.75 to 4.59 mg) anhydrous sodium hydrogen phosphate, and 15.84 mg (14.26 to 17.42 mg) purified water.

EXPERIMENTAL

Examples 1 to 82 relate to the formulation of the fill ingredients without the active pharmaceutical ingredient. These examples provide guidance on formulating the entire fill liquid. Examples 83 to 157 disclose abuse resistant liquid comprising various active pharmaceutical ingredients.

Unless otherwise specified, dispersability was tested in 0.1 N HCl with a paddle dissolution apparatus at 100 rpm.

One test for abuse resistance was whether a mixture with 5% water could be drawn up into a syringe. Compositions that could not be drawn up into a syringe or could hardly be drawn up into the syringe were considered to be abuse resistant. Also, compositions wherein about 33% or less of the pharmaceutically active ingredient could be recovered from the solution drawn up into the syringe also were considered to be abuse resistant.

Examples 1 to 3: Hard Fat Formulations

Examples 1 to 3 show that formulations based on hard fat are not likely to be viable abuse resistant formulations.

Example 1

15.8 g of medium chain triglycerides, 2.5 g of hydrogenated soya bean oil, 41.7 g of hard fat, 3.3 g of Povidone K 30, and 3.3 g of polyoxyl 40 hydrogenated castor oil were mixed to obtain a homogenous mixture. The mixture was firm at room temperature, and flowable and pourable at 30° C. When the mixture was boiled with water (ca. 250 mg of the mixture in 5 mL of water), hard fat separated on cooling down. No air bubbles were formed at boiling. The aqueous phase was syringeable with a 20 gauge needle, and small particles of hard fat were also observed in the syringe. After disintegration of the shell of lab filled capsules at about 25 minutes, the fill was dispersed with the remaining fat particles in the dissolution medium and an oil film on the surface.

Example 2

15.8 g of medium chain triglycerides, 2.5 g of hydrogenated soya bean oil, 41.7 g of hard fat, 3.3 g of Povidone K 30, and 3.3 g of polysorbate 80 h were mixed to obtain a homogenous mixture. The mixture was firm at room temperature, and flowable and pourable at 30° C. When the mixture was boiled with water, hard fat separated on cooling down. No air bubbles were formed at boiling and the aqueous phase was syringeable, and small particles of hard fat were also observed in the syringe. After disintegration of the shell at about 25 minutes, the fill was dispersed with the remaining fat particles in the dissolution medium and an oil film on the surface.

Example 3

15.8 g of medium chain triglycerides, 2.5 g of hydrogenated soya bean oil, 41.7 g of hard fat, 3.3 g of Povidone K 30, and 3.3 g of polyoxyl 35 castor oil were mixed to obtain a homogenous mixture. The mixture was firm at room temperature, and flowable and pourable at 30° C. When the mixture was boiled with water, hard fat separated on cooling down. No air bubbles were formed at boiling and the aqueous phase was syringeable, whereas small particles of hard fat were also observed in the syringe. After disintegration of the shell at about 25 minutes, the fill was dispersed with the remaining fat particles in the dissolution medium and an oil film on the surface.

Examples 4 to 18: Medium Chain Triglyceride Formulations (LFCS Type I, II and III)

By use of medium chain triglycerides as a solvent/carrier and Polysorbate 80 and/or Span 20, Cremophor EL/RH 40 and Labrasol as surfactants, the compositions of Examples 4 to 13 were prepared. Those formulations, which were physically stable and showed formation of little bubbles at boiling, were syringeable. The compositions of Examples 14 to 18 show the effect of the addition of gelling agents xanthan gum and/or colloidal anhydrous silica.

Example 4

45.0 g of medium chain triglycerides, 10.0 g of hydrogenated soya bean oil, and 10.0 g of polyoxyl 40 hydrogenated castor oil were mixed to obtain a homogenous mixture. The mixture was soft, flowable and pourable at room temperature. The sample exhibited a sheen of oil and sedimentation.

Example 5

45.0 g of medium chain triglycerides, 10.0 g of hydrogenated soya bean oil, and 10.0 g of polysorbate 80 were mixed to obtain a homogenous mixture. The mixture was soft, flowable and pourable at room temperature. The sample exhibited a sheen of oil and sedimentation.

Example 6

45.0 g of medium chain triglycerides, 10.0 g of hydrogenated soya bean oil, and 10.0 g of polyoxyl 35 castor oil were mixed to obtain a homogenous mixture. The mixture was soft, flowable and pourable at room temperature. The sample exhibited a sheen of oil and sedimentation.

Example 7

10.0 g of medium chain triglycerides and 40.0 g of polysorbate 80 were mixed to obtain a homogenous mixture. The mixture was a clear yellowish solution. When the solution was boiled with water, no frothing was observed.

Example 8

41.0 g of caprylocaproyl macrogol-8 glyceride, 6.5 g of medium chain triglycerides, and 2.5 g of polyglycerol-6-dioleate were mixed to obtain a clear yellowish solution. Upon addition of water, a white emulsion was obtained. No frothing was observed upon boiling with water.

Example 9

8.0 g of medium chain triglycerides, 25.6 g of polysorbate 80, and 6.4 g of sorbitan monolaurate were mixed to obtain a homogenous mixture. The mixture was a clear yellowish solution. Upon addition of water, a turbid solution was obtained. Little frothing was observed upon boiling with water. The turbid solution could be drawn up into the syringe with little frothing.

Example 10

12.0 g of medium chain triglycerides, 22.4 g of polysorbate 80, and 5.6 g of sorbitan monolaurate were mixed to obtain a homogenous mixture. The mixture was a clear yellowish solution. Upon addition of water, an almost clear solution was obtained. Little frothing was observed upon boiling with water. The solution could be drawn up into the syringe with little frothing.

Example 11

16.0 g of medium chain triglycerides, 19.2 g of polysorbate 80, and 4.8 g of sorbitan monolaurate were mixed to obtain a homogenous mixture. The mixture was a clear yellowish solution. Upon addition of water, a turbid solution was obtained. Little frothing was observed upon boiling with water. The milky solution could be drawn up into the syringe with little frothing.

Example 12

20.0 g of medium chain triglycerides, 16.0 g of polysorbate 80, and 4.0 g of sorbitan monolaurate were mixed to obtain a homogenous mixture. The mixture was a clear yellowish solution. Upon addition of water, a white emulsion was obtained. Little frothing was observed upon boiling with water. The milky emulsion could be drawn up into the syringe with little frothing.

Example 13

24.0 g of medium chain triglycerides, 12.8 g of polysorbate 80, and 3.2 g of sorbitan monolaurate were mixed to obtain a homogenous mixture. The mixture was a clear yellowish solution. Upon addition of water, a white emulsion was obtained. Little frothing was observed upon boiling with water. The milky emulsion could be drawn up into the syringe with little frothing.

Example 14

12.0 g of medium chain triglycerides, 22.4 g of polysorbate 80, 5.6 g of sorbitanmonolaurate, 1.5 g of colloidal anhydrous silica, and 4.0 g of xanthan gum were mixed to obtain a homogenous yellowish suspension that was a pourable liquid. Upon addition of water, the suspension formed a gel. Upon boiling with water, frothing was observed, but the foam does not persist. The solution could not be drawn up into the syringe.

The yellowish suspension was used to fill a tube-shaped capsule. The capsule was then tested for dispersability and after about 20 minutes, about 40% of the fill dispersed.

Example 15

12.0 g of medium chain triglycerides, 22.4 g of polysorbate 80, 5.6 g of sorbitan monolaurate, and 2.0 g of colloidal anhydrous silica were mixed to obtain a yellowish gel that was almost clear. Upon addition of water, a white emulsion formed. Upon boiling with water, little frothing was observed. The milky solution could be drawn up into the syringe.

Example 16

12.0 g of medium chain triglycerides, 22.4 g of polysorbate 80, 5.6 g of sorbitan monolaurate, 2.0 g of colloidal anhydrous silica, and 2.0 g of xanthan gum were mixed to obtain a homogenous yellowish suspension that was pourable. Upon addition of water, a gel formed. Upon boiling with water, frothing was observed and the foam does not persist. The milky solution could hardly be drawn up into the syringe. At a higher concentration of the suspension (1 g in 5 mL of water), the resulting mixture exhibits very strong frothing, and the mixture could not be drawn into the syringe. The yellowish suspension was tested for dispersability as in Example 14 and after about 4.5 minutes the capsule opened; after about 20 to 25 minutes about 80% of the fill dissolved. After about 30 to 35 minutes 100% of the fill was dissolved.

Example 17

12.0 g of medium chain triglycerides, 22.4 g of polysorbate 80, 5.6 g of sorbitan monolaurate, 1.5 g of colloidal anhydrous silica, and 1.5 g of xanthan gum were mixed to obtain a homogenous yellowish suspension that was pourable. Upon addition of water, a gel formed. Upon boiling with water, frothing was observed and the foam does not persist. The milky solution could hardly be drawn up into the syringe. At a higher concentration of the suspension, the resulting mixture exhibited very strong frothing, and the mixture would hardly be drawn into the syringe. The foam could be pressed out.

Example 18

12.0 g of medium chain triglycerides, 22.4 g of polysorbate 80, 5.6 g of sorbitan monolaurate, 1.5 g of colloidal anhydrous silica, and 1.0 g of xanthan gum were mixed to obtain a homogenous yellowish suspension that was pourable. Upon addition of water, a gel formed. Upon boiling with water, frothing was observed and the foam does not persist. The milky solution could hardly be drawn up into the syringe. At a higher concentration of the suspension, the resulting mixture exhibited very strong frothing, and the mixture could hardly be drawn into the syringe. The foam could be pressed out. The yellowish suspension was tested for dispersability as in Example 14 and after about 4.5 minutes the capsule opened; after about 20 to 25 minutes about 80% of the fill was dissolved. After about 30 to 35 minutes 100% of the fill was dissolved.

Examples 19 to 37: Macrogol Formulations (LFCS Type III and IV)

Several different formulations (Example nos. 19 to 26) based on 7:1 mixtures of macrogol 400 with medium chain triglycerides or propylene glycol, polysorbate 80, Span 20, or Cremophor RH 40/EL as surfactants and colloidal anhydrous silica were prepared. The resulting opalescent to turbid yellowish homogeneous solutions formed emulsions or clear solutions after boiling with water. No formation of bubbles was observed.

By use of xanthan gum as a gelling agent (Example nos. 27 to 29) added to the macrogol/propylene glycol mixtures, sedimentation and separation in phases resulted.

3:1 mixtures of macrogol 400 with the surfactants Cremophor RH 40, polysorbate 80 and Labrasol (Example Nos. 30 to 32) and colloidal anhydrous silica/xanthan gum as gelling agents were yellowish homogeneous suspensions, which formed a gel and a partially persisting foam at boiling in the water. The solution was not syringeable but the dispersibility of the gel was poor due to formation of a compact mass after 6 minutes in the dispersion medium.

A mixture of 30% macrogol 400 with 10% polysorbate 80 or Cremophor RH 40 and 2% colloidal silicon dioxide (Example Nos. 33 and 34) formed clear, not fluid gels. After boiling with water the resulting white non bubbling emulsions were easily syringeable with little frothing. The formulations showed a good dispersibility (80% after 20 minutes).

Replacement of Span 20 and Polysorbate 80 by Labrasol®, (Caprylo-Caproyl macrogolglycerides) in Example No. 35 gave good results. The clear to yellowish gel formed a white, little bubbling emulsion at boiling with water. The milky emulsion, though it could be drawn up with the syringe, formed intense bubbles in the syringe. The syringability was reduced by addition of xanthan gum as an additional gelling agent in Example Nos. 36 and 37. Macrogol 400 or macrogol 600 were used.

Example 19

42.5 g of macrogol 400, 6.3 g of medium chain triglycerides, 6.3 g of polysorbate 80, and 1.3 g of colloidal anhydrous silica were mixed to obtain an opalescent, yellowish solution. Upon addition of water, a white emulsion was obtained. Upon boiling with water, no frothing was observed.

Example 20

42.5 g of macrogol 400, 6.3 g of medium chain triglycerides, 6.3 g of polyoxyl 40 hydrogenated castor oil, and 1.3 g of colloidal anhydrous silica were mixed to obtain an opalescent, yellowish solution. Upon addition of water, a white emulsion was obtained. Upon boiling with water, no frothing was observed.

Example 21

42.5 g of macrogol 400, 6.3 g of medium chain triglycerides, 6.3 g of polyoxyl 35 castor oil, and 1.3 g of colloidal anhydrous silica were mixed to obtain an opalescent, yellowish solution. Upon addition of water, a white emulsion was obtained. Upon boiling with water, no frothing was observed.

Example 22

38.8 g of macrogol 400, 6.3 g of propylene glycol, 2.5 g of water, 6.3 g of polysorbate 80, and 2.5 g of Povidone K 30 were mixed to obtain a pale yellow, turbid solution that separated.

Example 23

38.8 g of macrogol 400, 6.3 g of propylene glycol, 2.5 g of water, 6.3 g of polysorbate 20, and 2.5 g of Povidone K 30 were mixed to obtain a homogenous pale yellow, turbid solution. Upon addition of water, a clear solution was obtained. Upon boiling with water, no frothing was observed.

Example 24

38.8 g of macrogol 400, 6.3 g of propylene glycol, 2.5 g of water, 6.3 g of polyoxyl 40 hydrogenated castor oil, and 2.5 g of Povidone K 30 were mixed to obtain a homogenous pale yellow, almost clear solution. Upon addition of water, a clear solution was obtained. Upon boiling with water, no frothing was observed.

Example 25

38.8 g of macrogol 600, 6.3 g of propylene glycol, 2.5 g of water, 6.3 g of polysorbate 80, and 2.5 g of Povidone K 30 were mixed to obtain a pale yellow, turbid solution that separated.

Example 26

38.8 g of macrogol 600, 6.3 g of propylene glycol, 2.5 g of water, 6.3 g of polysorbate 80, and 2.5 g of Povidone K 30 were mixed to obtain a pale yellow, turbid solution that separated.

Example 27

35.0 g of macrogol 600, 6.3 g of propylene glycol, 2.5 g of water, 6.3 g of polyoxyl 35 castor oil, and 6.3 g of xanthan gum were mixed to obtain a mixture that separated and sedimented.

Example 28

35.0 g of macrogol 600, 6.3 g of propylene glycol, 2.5 g of water, 6.3 g of polysorbate 20, and 6.3 g of xanthan gum were mixed to provide a mixture that separated and sedimented.

Example 29

35.0 g of macrogol 600, 6.3 g of propylene glycol, 2.5 g of water, 6.3 g of polyoxyl 40 hydrogenated castor oil, and 6.3 g of xanthan gum were mixed to obtain a mixture that separated and sedimented.

Example 30

30.0 g of macrogol 400, 10.0 g of polyoxyl 40 hydrogenated castor oil, 5.0 g of xanthan gum, and 1.0 g of colloidal anhydrous silica were mixed to obtain a homogeneous yellowish suspension that was pourable. The suspension formed a gel when mixed with water. Upon boiling, the gel frothed and the foam partially persisted. The resulting solution could not be drawn up in a syringe. The yellowish suspension was tested for dispersability as in Example 14 and after about 60 minutes the fill was a compact mass with less than 50% of the fill dissolved.

Example 31

30.0 g of macrogol 400, 10.0 g of polysorbate 80, 5.0 g of xanthan gum, and 1.0 g of colloidal anhydrous silica were mixed to obtain a homogeneous yellowish suspension that was pourable. The suspension formed a gel when mixed with water. Upon boiling, the gel frothed and the foam did not persist. The resulting solution could not be drawn up in a syringe. The yellowish suspension was tested for dispersability and after about 60 minutes the fill was a compact mass with less than 50% of the fill dissolved.

Example 32

30.0 g of macrogol 400, 10.0 g of caprylocaproyl macrogol-8 glyceride, 5.0 g of xanthan gum, and 1.0 g of colloidal anhydrous silica were mixed to obtain a homogeneous yellowish suspension that was pourable. The suspension formed a gel when mixed with water. Upon boiling, the gel frothed, wherein the foam partially persisted. The resulting solution could not be drawn up in a syringe. The yellowish suspension was tested for dispersability and after about 60 minutes the fill was a compact mass with less than 50% of the fill dissolved.

Example 33

30.0 g of macrogol 400, 10.0 g of polyoxyl 40 hydrogenated castor oil, and 2.0 g of colloidal anhydrous silica were mixed to obtain a colorless gel that was pourable. The gel formed a white emulsion when mixed with water. Upon boiling, no frothing was observed. The resulting solution could not be drawn up in a syringe. The formulation was tested for dispersability and after about 20 minutes, about 90% of the fill dispersed.

Example 34

30.0 g of macrogol 400, 10.0 g of polysorbate 80, and 2.0 g of colloidal anhydrous silica were mixed to obtain a turbid yellowish gel that was barely pourable. The gel formed a white emulsion when mixed with water. Upon boiling, no frothing was observed. The resulting solution could be drawn up in a syringe. The formulation was tested for dispersability and after about 20 minutes, about 80% of the fill dispersed.

Example 35

30.0 g of macrogol 400, 10.0 g of caprylocaproyl macrogol-8 glyceride, and 2.0 g of colloidal anhydrous silica were mixed to obtain a clear yellowish gel that was pourable. The gel formed a white emulsion when mixed with water. Upon boiling, strong frothing was observed. The resulting solution could be drawn up in a syringe. For the higher concentration of the formulation in water, the resulting milky emulsion exhibits strong frothing and could be drawn up into the syringe. The dispersability test showed that after about 20 minutes 80% of the fill was dissolved, and within 30 minutes the entire fill was dissolved.

Example 36

30.0 g of macrogol 600, 10.0 g of caprylocaproyl macrogol-8 glyceride, 2.0 g of colloidal anhydrous silica, and 0.8 g of xanthan gum were mixed to obtain a turbid yellowish gel that was barely pourable. The mixture formed a gel when mixed with water. Upon boiling, little frothing was observed. The resulting mixture could be drawn up in a syringe. For the higher concentration of the formulation in water, the resulting mixture could not be drawn up into the syringe, and strong frothing was observed.

Example 37

30.0 g of macrogol 400, 10.0 g of caprylocaproyl macrogol-8 glyceride, 2.0 g of colloidal anhydrous silica, and 2.0 g of xanthan gum were mixed to obtain a turbid yellowish gel that was barely pourable. The mixture formed a gel when mixed with water. Upon boiling, little frothing was observed. The resulting mixture could be drawn up in a syringe. For the higher concentration of the formulation in water, the resulting mixture could not be drawn up into the syringe, and exhibited strong frothing. The dispersability test showed that after about 20 minutes 80% of the fill was dissolved, and within 30 minutes the entire fill was dissolved.

Examples 38 to 46: Medium Chain Partial Glycerides Formulations (LFCS Type II and III a/b)

Six formulations (Example Nos. 38 to 43) were prepared based on medium chain partial glycerides as solvents in combination with different surfactants. The yellowish solutions formed white non-frothing emulsions with water. By addition of a mixture of propylene glycol and Lipoid PPL 600 (Example Nos. 44 to 46) a non-persisting foam was obtained at bubbling. However, the emulsions were easily syringeable. This demonstrates the lack of suitability of medium chain partial glycerides as suitable solvents in fills for abuse resistant capsules.

Example 38

33.8 g of medium chain partial glycerides, 6.3 g of polysorbate 80, and 3.8 g of Povidone K 30 were mixed to obtain a clear pale yellow solution. The mixture formed a grey emulsion when mixed with water. Upon boiling, no frothing was observed.

Example 39

33.8 g of medium chain partial glycerides, 6.3 g of polysorbate 20, and 3.8 g of Povidone K 30 were mixed to obtain a clear pale yellow solution. The mixture formed a grey translucent emulsion when mixed with water. Upon boiling, no frothing is observed.

Example 40

33.8 g of medium chain partial glycerides, 6.3 g of polyoxyl 40 hydrogenated castor oil, and 3.8 g of Povidone K 30 were mixed to obtain a clear pale yellow solution. The mixture formed a white emulsion when mixed with water. Upon boiling, no frothing was observed.

Example 41

25.0 g of medium chain partial glycerides, 18.0 g of polysorbate 80, and 18.0 g of propylene glycol were mixed to obtain a clear pale yellow solution. The mixture formed a white emulsion when mixed with water. Upon boiling, no frothing was observed. The milky emulsion could be drawn up into the syringe.

Example 42

25.0 g of medium chain partial glycerides, 18.0 g of polysorbate 20, and 18.0 g of propylene glycol were mixed to obtain a clear pale yellow solution. The mixture formed a white emulsion when mixed with water. Upon boiling, no frothing was observed.

Example 43

25.0 g of medium chain partial glycerides, 6.3 g of polysorbate 20, and 3.8 g of Povidone K 30 were mixed to obtain a clear pale yellow solution. The mixture formed a grey translucent emulsion when mixed with water. Upon boiling, no frothing was observed.

Example 44

35.0 g of medium chain partial glycerides and 15.0 g of lipoid PPL-600 were mixed to obtain a clear reddish brown solution. When mixed with water, the mixture spreads, but does not form an emulsion. Upon boiling, frothing was observed, but it did not persist. The milky emulsion could be drawn up into the syringe.

Example 45

25.0 g of medium chain partial glycerides, 15.0 g of lipoid PPL-600, and 10.0 g of propylene glycol were mixed to obtain a clear reddish brown solution. When mixed with water, the mixture spreads, but does not form an emulsion. Upon boiling, frothing was observed, but it did not persist. The milky emulsion could be drawn up into the syringe.

Example 46

20.0 g of medium chain partial glycerides, 10.0 g of lipoid PPL-600, and 20.0 g of propylene glycol were mixed to obtain a clear reddish brown solution. When mixed with water, the mixture spreads, but does not form an emulsion. Upon boiling, frothing was observed, but it did not persist. The milky emulsion could be drawn up into the syringe.

Examples 47 to 65: Phospholipid Formulations (LFCS Type II and III a/b)

Formulations of Example Nos. 47 to 55 were based on Lipoid PPL 600 (a mixture of phospholipids (76% PC) with medium chain triglycerides, soya bean oil, tocopherol and glycerol-fatty acid esters) Mixtures with macrogol were physically not stable and separated into two phases. In 1:1 to 6:1 mixtures with propylene glycol and polysorbate 80 (Example Nos. 52 to 55) clear reddish brown solutions resulted, and formed a white emulsion with a non-persisting foam at boiling. The emulsions of the formulations of Example Nos. 54 and 55 were not syringeable under strong foaming; both formulations were easily dispersed after about 15 minutes in the dissolution medium.

Mixtures of Lipoid PPL 600 with propylene glycol were chosen as the alternative to phospholipide concentrate Phosal 50 PG, which contains approx. 56% phospholipids and 36% propylene glycol, 3% mono- and diglycerides and 2.4% soya fatty acids plus 2% ethanol as carriers.

The formulations of Example Nos. 56 to 58 as 9:1 mixtures of Phosal 50 PG with polysorbate 80, Span 20 and Cremophor RH 40 were clear yellowish solutions which formed a gelling emulsion with a partially persisting foam at boiling. By use of 250 mg of fill mass, the fill emulsion was syringeable but exhibited intensive formation of air bubbles. 1000 mg of formulation Example No. 56 could not be drawn up in the syringe.

By addition of colloidal anhydrous silica (Example Nos. 59, 64, and 65), the frothing suspension could hardly be drawn up in the syringe due to a higher viscosity and formation of air bubbles.

Additional xanthan gum (Example No. 60) was added and the boiled emulsion separated in two phases. Based on the miscibility results of phosal (surfactant mixtures with ethanol) and water, 10% water (formulation of Example No. 61) or mixtures of ethanol and water (formulations of Example Nos. 62 and 63) were added to the Phosal 50 PG/polysorbate 80 combinations. The clear to turbid yellow solutions formed partially gelling emulsions with bubbles at boiling. The syringability of 1000 mg of these formulations was intensively reduced by formation of very strong bubbles.

Example 47

25.0 g of lipoid PPL-600, and 25.0 g of macrogol 600 were mixed to obtain a mixture that separates and solids appear within one day of standing.

Example 48

25.0 g of lipoid PPL-600, and 25.0 g of macrogol 400 were mixed to obtain a mixture that separates after one day of standing.

Example 49

25.0 g of lipoid PPL-600, and 25.0 g of propylene glycol were mixed to obtain a mixture that separates and solids appear within one day of standing.

Example 50

10.0 g of lipoid PPL-600, 10.0 g of macrogol 600, and 5.0 g of medium chain partial glycerides were mixed to obtain a mixture that separates.

Example 51

10.0 g of lipoid PPL-600, 10.0 g of macrogol 400, and 5.0 g of medium chain partial glycerides were mixed to obtain a mixture that separates.

Example 52

10.0 g of lipoid PPL-600, 10.0 g of propylene glycol, and 5.0 g of medium chain partial glycerides were mixed to obtain a clear reddish brown solution. When mixed with water, a yellowish emulsion formed. Upon boiling, frothing was observed, but it did not persist. The milky emulsion could be drawn up into the syringe.

Example 53

12.5 g of lipoid PPL-600, 18.8 g of polysorbate 80, and 18.8 g of propylene glycol were mixed to obtain a clear reddish brown solution. When mixed with water the mixture turns turbid. Upon boiling, little frothing was observed. The turbid emulsion could be drawn up into the syringe.

Example 54

25.0 g of lipoid PPL-600, 12.5 g of polysorbate 80, and 12.5 g of propylene glycol were mixed to obtain a clear yellow-brown solution. When mixed with water a white emulsion formed. Upon boiling, little frothing was observed, and the foam did not persist. The milky emulsion could be drawn up into the syringe.

Example 55

37.5 g of lipoid PPL-600, 6.3 g of polysorbate 80, and 6.3 g of propylene glycol were mixed to obtain a clear reddish-brown solution. When mixed with water a white emulsion formed. Upon boiling, frothing was observed, and the foam partially persisted. It was very difficult to draw up the milky emulsion into the syringe.

Example 56

20.0 g of Phosal 50 PG and 2.0 g of polysorbate 80 were mixed to obtain a clear yellow solution. A yellowish emulsion formed when mixed with water, partially forming a gel. Upon boiling, frothing was observed, and the foam partially persisted. Although it was possible to draw the frothy milky emulsion obtained after boiling into the syringe, for the higher concentration, very strong frothing was observed, and the milky emulsion could not be drawn into the syringe. The dispersability test showed that after about 10 to 15 minutes 100% of the fill was finely dispersed.

Example 57

20.0 g of Phosal 50 PG and 2.0 g of polyoxyl 40 hydrogenated castor oil were mixed to obtain a clear yellow solution. A yellowish emulsion formed when mixed with water, partially forming a gel. Upon boiling, frothing was observed, and the foam partially persisted. The resulting milky emulsion could be drawn into the syringe. The dispersability test showed that after about 15 minutes 100% of the fill was dispersed.

Example 58

20.0 g of Phosal 50 PG and 2.0 g of sorbitanmonolaurate were mixed to obtain a clear yellow solution. A yellowish emulsion formed when mixed with water, partially forming a gel. Upon boiling, frothing was observed, and the foam partially persisted. The resulting milky emulsion could be drawn into the syringe. The dispersability test showed that after about 15 minutes 100% of the fill was dispersed.

Example 59

20.0 g of Phosal 50 PG, 2.0 g of polysorbate 80, and 1.5 g of colloidal anhydrous silica were mixed to obtain a clear yellow solution. A yellowish emulsion formed when mixed with water, partially forming a gel. Upon boiling, frothing was observed, and the foam partially persisted. It was difficult to draw the milky emulsion into the syringe.

Example 60

20.0 g of Phosal 50 PG, 2.0 g of polysorbate 80, 1.5 g of colloidal anhydrous silica, and 1.5 g of xanthan gum were mixed to obtain a yellow suspension. A yellowish emulsion formed when mixed with water, partially forming a gel. Upon boiling, frothing was observed, and the foam partially persisted. It was difficult to draw the milky emulsion into the syringe. At the higher concentrations, the formulation separates, and the aqueous phase could be drawn into the syringe.

Example 61

9.0 g of Phosal 50 PG, 1.0 g of polysorbate 80, and 1.0 g of water were mixed to obtain a turbid yellow suspension. A yellowish emulsion formed when mixed with water, partially forming a gel. Upon boiling, frothing was observed, and the foam partially persisted. Although it was possible to draw the frothy milky emulsion obtained after boiling into the syringe, for the higher concentration, very strong frothing was observed, and the milky emulsion could not be drawn into the syringe. The dispersability test showed that after about 20 minutes 100% of the fill was finely dispersed.

Example 62

9.0 g of Phosal 50 PG, 1.0 g of polysorbate 80, 0.75 g of water, and 0.25 g of ethanol were mixed to obtain an almost clear yellow solution. A yellowish emulsion formed when mixed with water, partially forming a gel. Upon boiling, frothing was observed, and the foam partially persisted. The milky emulsion could be drawn into the syringe.

Example 63

9.0 g of Phosal 50 PG, 1.0 g of polysorbate 80, 0.5 g of water, and 0.5 g of ethanol were mixed to obtain a clear yellow suspension. A yellowish emulsion formed when mixed with water, partially forming a gel. Upon boiling, frothing was observed, and the foam partially persisted. Although it was possible to draw the frothy milky emulsion obtained after boiling into the syringe, for the higher concentration, very strong frothing was observed, and the milky emulsion could not be drawn into the syringe. The dispersability test showed that after about 10 minutes 100% of the fill was finely dispersed.

Example 64

20.0 g of Phosal 50 PG, 2.0 g of sorbitan monolaurate, and 1.5 g of colloidal anhydrous silica were mixed to obtain an almost clear yellow suspension. A yellowish emulsion formed when mixed with water, partially forming a gel. Upon boiling, frothing was observed, and the foam partially persisted. It was very difficult to draw the frothy milky emulsion into the syringe.

Example 65

20.0 g of Phosal 50 PG, 2.0 g of sorbitan monolaurate, and 1.5 g of colloidal anhydrous silica and 1.5 g of xanthan gum were mixed to obtain a yellow suspension. A yellowish emulsion formed when mixed with water, partially forming a gel. Upon boiling, frothing was observed, and the foam partially persisted. It was very difficult to draw the frothy milky emulsion into the syringe.

Example 66

10.0 g of propylene glycol monolaurate and 5.0 g of Polyoxyl 40 hydrogenated castor oil were mixed to obtain a white, turbid mixture, which separated after approximately 2 days. A flocculent emulsion formed when mixed with water. No frothing was observed upon boiling.

Example 67

10.0 g of propylene glycolmonolaurate and 5.0 g of Labrafil M 2125 CS were mixed to obtain a clear yellowish solution. The solution separates when mixed with water. No frothing was observed upon boiling.

Example 68

10.0 g of propylene glycolmonolaurate and 5.0 g of polysorbate 80 were mixed to obtain a clear yellowish solution. A white emulsion formed when the solution was mixed with water. No frothing was observed upon boiling.

Example 69

10.0 g of propylene glycolmonolaurate and 5.0 g of caprylocaproylmacrogol-8 glyceride were mixed to obtain a clear colorless solution. A white emulsion formed when the solution was mixed with water. No frothing was observed upon boiling.

Example 70

10.0 g of propylene glycolmonolaurate and 5.0 g of lipoid PPL-600 were mixed to obtain a clear yellowish solution. Upon addition of water, the solution partially formed a gel and separated. No frothing was observed upon boiling.

Example 71

10.0 g of propylene glycolmonolaurate and 5.0 g of macrogol-32-glycerollarate were mixed to obtain a white solid mass.

Example 72

2.0 g of gelucire 44/14 and 8.0 g of lipoid PPL-600 were mixed to obtain a yellow-brown solid mass.

Example 73

2.0 g of gelucire 44/14 and 8.0 g of Labrafil M 2125 CS were mixed to obtain a turbid, yellowish, pasty liquid that separated. Upon addition of water, a white emulsion formed. No frothing was observed upon boiling.

Example 74

2.0 g of gelucire 44/14 and 8.0 g of medium chain partial glycerides were mixed to obtain a clear yellowish solution. Upon addition of water, a white emulsion formed. No frothing was observed upon boiling.

Example 75

2.0 g of gelucire 44/14 and 8.0 g of macrogol 600 were mixed to obtain a white solid mass.

Example 76

2.0 g of gelucire 44/14 and 8.0 g of propylene glycolmonolaurate were mixed to obtain a white, turbid solution that separated. Upon addition of water, a white emulsion formed. No frothing was observed upon boiling.

Example 77

2.0 g of gelucire 44/14 and 8.0 g of corn oil mono-/di-/tri-glycerides were mixed to obtain a clear yellowish solution that solidifies after 1 to 2 days. Upon addition of water, a white emulsion formed. No frothing was observed upon boiling.

Example 78

25.0 g of polysorbate 80, 12.5 g of ethanol, and 12.5 g of propylene glycol were mixed to obtain a clear yellowish solution. Upon addition of water, a clear solution formed. Frothing was observed upon boiling, but the foam does not persist.

Example 79

5.0 g of macrogol-32-glycerollaurate, 37.5 g of polyglycerol-6-dioleate, and 20.0 g of propylene glycol were mixed to obtain a mixture that separates.

Example 80

10.0 g of macrogol-32-glycerollaurate, 10.0 g of polyglycerol-6-diolate, and 20.0 g of propylene glycol were mixed to obtain a mixture that separates, and partly solidifies.

Example 81

15.0 g of macrogol-32-glycerollaurate, 5.0 g of polyglycerol-6-dioleate, and 20.0 g of propylene glycol were mixed to obtain a mixture that separates, and partly solidifies.

Example 82

25.0 g of polysorbate 80 and 25.0 g of glyceryl-monocaprate/-caprylate were mixed to obtain a clear yellowish solution. Upon mixing with water, a white emulsion if obtained. Little frothing was observed upon boiling.

Examples 83 to 93: Lipophilic Pseudoephedrine HCl Formulations

Lipophilic formulations of Examples 83 to 93 provide abuse resistant softgel formulations for highly lipophilic actives. Lipid based fill formulations (LFCS I and II) were developed containing hard fat and medium chain triglycerides as a lipid matrix and xanthan gum as a viscosity enhancing agent. The formulations differed regarding their concentrations of hard fat (0 to 62.2 wt %), medium chain triglycerides (0 to 62.2 wt %), surfactant (5.0 to 45.6 wt %), xanthan gum (1.1 to 4.4 wt %), and colloidal anhydrous silica (0 to 1.7 wt %). Polysorbate 80, sorbitan monooleate, single and in mixtures and macrogolglycerol ricinoleate (Kolliphor EL) were used as surfactants.

These lipophilic formulations, especially those containing high concentrations of hard fat, were developed based on the initial results of non complaint IR dissolution properties with the objective of an extended release profile. Some formulations show unexpected IR release profiles from lab filled softgels containing 116.48 mg pseudoephedrine HCl in 870 to 900 mg of fill.

Working Example 83

14.6 g of medium chain triglycerides, 27.3 g of polysorbate 80, 6.7 g of Sorbitan monolaurate (SPAN 20), 1.0 g of colloidal anhydrous silica, 2.7 g of xanthan gum, and 7.8 g of pseudoephedrine HCl were mixed to obtain a beige, homogenous, soft, flowable, pourable suspension that frothed upon boiling, and formed a gel. It could hardly be drawn up into the syringe, 7.8% pseudoephedrine HCl was detected. Within 30 minutes, about 93.9% of pseudoephedrine HCl was released in 0.1 N HCl.

Comparative Example 84

9.2 g of medium chain triglycerides, 37.3 g of hard fat, 3.0 g of polysorbate 80, 2.7 g of xanthan gum, and 7.8 g of pseudoephedrine HCl were mixed to obtain an off-white suspension that was pourable and flowable at 30° C., but was a solid at room temperature

Comparative Example 85

14.6 g of hard fat, 27.3 g of polysorbate 80, 6.7 g of sorbitan monolaurate/SPAN 20, 1.0 g of colloidal anhydrous silica, 2.7 g of xanthan gum, and 7.8 g of pseudoephedrine HCl were mixed to obtain an off-white suspension that was pourable and flowable at 30° C., but was a solid at room temperature.

Comparative Example 86

35.2 g of hard fat, 6.7 g of polysorbate 80, 6.7 g of sorbitan monolaurate/SPAN 20, 1.0 g of colloidal anhydrous silica, 2.7 g of xanthan gum, and 7.8 g of pseudoephedrine HCl were mixed to obtain an off white suspension that was pourable and flowable at 30° C., but was firm at room temperature. After boiling with water, it could hardly be drawn up into the syringe; 5.8% pseudoephedrine HCl was detected. Within 30 minutes 87.6% of pseudoephedrine HCl was released in 0.1 N HCl.

Comparative Example 87

9.2 g of medium chain triglycerides, 34.3 g of hard fat, 6.0 g of polysorbate 80, 2.7 g of xanthan gum, and 7.8 g of pseudoephedrine HCl were mixed to obtain an off white suspension that was pourable and flowable at 30° C., but was firm at room temperature. After boiling with water, it could hardly be drawn up into the syringe; 3.2% of pseudoephedrine HCl was detected. Within 30 minutes, 100.5% of pseudoephedrine HCl was detected as released in 0.1 N HCl.

Comparative Example 88

9.2 g of medium chain triglycerides, 37.3 g of hard fat, 3.0 g of macrogol glycerol ricinoleate, 2.7 g of xanthan gum, and 7.8 g of pseudoephedrine HCl were mixed to obtain an off white suspension that was pourable and flowable at 30° C., but was firm at room temperature. It could hardly be drawn up into the syringe; 8.1% pseudoephedrine HCl was detected. Within 30 minutes, 111% of pseudoephedrine HCl was detected as released in 0.1 N HCl.

Comparative Example 89

35.2 g of hard fat, 6.7 g of polysorbate 80, 6.7 g of sorbitan monolaurate/SPAN 20, 1.0 g of colloidal anhydrous silica, 2.7 g of xanthan gum, and 7.8 g of pseudoephedrine HCl were mixed to obtain an off white suspension that was pourable and flowable at 30° C., but was firm at room temperature.

Comparative Example 90

9.2 g of medium chain triglycerides, 34.3 g of hard fat, 6.0 g of polysorbate 80, 2.7 g of xanthan gum, and 7.8 g of pseudoephedrine HCl were mixed to obtain an off white suspension that was pourable and flowable at 30° C., but was firm at room temperature.

Comparative Example 91

14.6 g of medium chain triglycerides, 27.3 g of polysorbate 80, 6.7 g of sorbitan monolaurate/SPAN 20, 1.0 g of colloidal anhydrous silica, 0.7 g of xanthan gum, and 7.8 g of pseudoephedrine HCl were mixed to obtain a beige suspension that was homogenous, soft, flowable, and pourable.

Comparative Example 92

43.7 g of medium chain triglycerides, 82.0 g of polysorbate 80, 20.0 g of sorbitan monolaurate/SPAN 20, 3.0 g of colloidal anhydrous silica, 2.0 g of xanthan gum, and 23.3 g of pseudoephedrine HCl were mixed to obtain a beige suspension that homogenous, soft, flowable, and pourable.

Working Example 93

9.2 g of medium chain triglycerides, 37.3 g of hard fat, 3.0 g of polysorbate 80, 2.7 g of xanthan gum, 7.8 g of pseudoephedrine HCl were mixed to obtain an off-white suspension that was pourable, flowable at 30° C., but firm at room temperature. After boiling with water it could hardly be drawn up into the syringe; 8.3% pseudoephedrine HCl was detected. Within 120 minutes 49.2% of pseudoephedrine HCl was released in 0.1 N HCl, after 240 minutes 92.6% of pseudoephedrine HCl was released in a pH 4.6 buffer. After 720 minutes 97.8% of pseudoephedrine HCl was released in a pH 6.8 buffer.

Examples 94 to 100: Lipophilic Formulations

In order to achieve an extended release dissolution profile mixtures of 5 to 20% Compritol 888 ATO (glycerol dibehenate) or Precirol ATO 5 (glyceryl stearate) with medium chain triglycerides were prepared by melting of such lipid components at 60° C. and cooling down by stirring to room temperature. These solid or semi-solid lipid matrices were incorporated into formulations based on medium chain triglycerides as a lipid excipient, polysorbate 80 as a surfactant and xanthan gum as a gelling, viscosity enhancing agent.

The use of Precirol ATO 5 in some of the examples below shows an excellent immediate release profile: for example, for the formulation of Example 95, within 30 minutes, about 90.7% of pseudoephedrine HCl was released.

Comparative Example 94

38.2 g of medium chain triglycerides, 8.0 g of Precirol® ATO 5 (glyceryl distearate) 2.3 g of polysorbate 80, 0.3 g of xanthan gum, and 5.8 g of pseudoephedrine HCl were mixed to obtain an off-white suspension that was pourable, flowable at 40° C., but firm at room temperature. The IR profile showed that 90.7% of pseudoephedrine HCl was released. Syringeability in subsequent work was optimized by increasing the xanthan gum loading level.

Comparative Example 95

28.7 g of medium chain triglycerides, 8.0 g of Compritol 888ATO, 2.3 g of polysorbate 80, 0.3 g of xanthan gum, and 5.8 g of pseudoephedrine HCl were mixed to obtain an off-white suspension that was pourable, flowable at 40° C., but firm at room temperature.

Comparative Example 96

34.4 g of medium chain triglycerides, 4.5 g of Compritol 888ATO, 2.3 g of polysorbate 80, 0.3 g of xanthan gum, and 5.8 g of pseudoephedrine HCl were mixed to obtain an off-white suspension that was pourable, flowable at 40° C., but firm at room temperature.

Comparative Example 97

36.7 g of medium chain triglycerides, 2.3 g of Compritol 888ATO, 2.3 g of polysorbate 80, 0.3 g of xanthan gum, and 5.8 g of pseudoephedrine HCl were mixed to obtain an off-white suspension that was pourable, flowable at 40° C., but firm at room temperature.

Comparative Example 98

13.2 g of medium chain triglycerides, 19.5 g of Hard Fat, 2.3 g of Compritol 888ATO, 2.3 g of polysorbate 80, 2.0 g of xanthan gum, and 5.8 g of pseudoephedrine HCl were mixed to obtain an off-white suspension that was pourable, flowable at 40° C., but firm at room temperature.

Comparative Example 99

43.2 g of medium chain triglycerides, 6.0 g of Compritol 888ATO, 3.0 g of polysorbate 80, 2.7 g of xanthan gum, and 7.8 g of pseudoephedrine HCl were mixed to obtain an off-white suspension that was pourable, flowable at 40° C., but firm at room temperature. The formulation could hardly be drawn up into the syringe.

Comparative Example 100

43.2 g of medium chain triglycerides, 6.0 g of Precirol ATO 5, 3.0 g of polysorbate 80, 2.7 g of xanthan gum, and 7.8 g of pseudoephedrine HCl were mixed to obtain an off-white suspension that was pourable, flowable at 40° C., but firm at room temperature. The formulation could hardly be drawn up into the syringe.

Examples 101 to 117: Phosal formulations

The compositions of Example Nos. 101, 102, 104 to 106, 108, and 109 are Phosal/polysorbate 80/colloidal anhydrous silica formulations. These formulations exhibit a release from lab filled capsules containing 116.48 mg pseudoephedrine HCl in 900 to 950 mg of fill, that was slower than immediate release, and was faster than the extended release formulations 107, 116 and 117, that exhibit a sustained release dissolution profile over 12 hours. An increase of the colloidal anhydrous silica concentration to 20 mg (2.2%) leads to a slower release profile.

Working Example 101

41.9 g of Phosal 50 PG, 4.7 g of polysorbate 80, 4.7 g of purified water, 1.0 g of colloidal anhydrous silica, and 7.8 g of pseudoephedrine HCl were mixed to obtain a yellow gel that was homogenous, soft, flowable, pourable, and almost clear. The mixture frothed on boiling, and formed a gel, which could hardly be drawn up into the syringe.

Working Example 102

41.9 g of Phosal 50 PG, 4.7 g of polysorbate 80, 4.7 g of purified water, 0.7 g of colloidal anhydrous silica, and 7.8 g of pseudoephedrine HCl were mixed to obtain a yellow gel that was homogenous, soft, flowable, pourable, and almost clear. The mixture frothed on boiling, and formed a gel, which could hardly be drawn up into the syringe. 16.7% pseudoephedrine HCl was detected. Within 30 minutes, 88.6% of pseudoephedrine HCl was released in 0.1N HCl.

Working Example 103

41.9 g of Phosal 50 PG, 5.0 g of polysorbate 80, 5.0 g of purified water, 0.3 g of xanthan gum, and 7.8 g of pseudoephedrine HCl were mixed to obtain a yellow gel that was homogenous, soft, flowable, pourable, and was turbid. The mixture frothed on boiling, and formed a gel, which could hardly be drawn up into the syringe.

Working Example 104

41.6 g of Phosal 50 PG, 4.7 g of polysorbate 80, 2.3 g of purified water, 2.3 g of Ethanol, anhydrous, 1.3 g of colloidal anhydrous silica, and 7.8 g of pseudoephedrine HCl were mixed to obtain a yellow gel that was homogenous, soft, flowable, pourable, and almost clear. The mixture frothed on boiling, and formed a gel, which could hardly be drawn up into the syringe.

Working Example 105

46.2 g of Phosal 50 PG, 4.7 g of polysorbate 80, 1.3 g of colloidal anhydrous silica, and 7.8 g of pseudoephedrine HCl were mixed to obtain a yellow gel that was homogenous, soft, flowable, pourable, and almost clear. The mixture frothed on boiling, and formed a gel, which could hardly be drawn up into the syringe.

Working Example 106

40.2 g of Phosal 50 PG, 5.0 g of polysorbate 80, 5.7 g of purified water, 1.3 g of colloidal anhydrous silica, and 7.8 g of pseudoephedrine HCl were mixed to obtain a yellow gel that was homogenous, soft, flowable, pourable, and was turbid. The mixture frothed on boiling, and formed a gel, which could hardly be drawn up into the syringe.

Working Example 107

37.6 g of Phosal 50 PG, 12.7 g of caprylocaproyl macrogol-8 glycerides, 2.7 g of purified water, 2.7 g of xanthan gum, and 7.8 g of pseudoephedrine HCl were mixed to obtain a yellow gel that was homogenous, soft, flowable, pourable, and was turbid. The mixture frothed on boiling, and formed a gel, which could hardly be drawn up into the syringe. 7.4% of pseudoephedrine HCl were detected in the syringe. 25.0% of pseudoephedrine HCl was released from a lab filled softgel capsule containing 116.48 mg of pseudoephedrine HCl in 950 mg of fill after 2 hours in 0.1 N HCl, 46.3% after 4 hours in a pH 4.6 buffer and 85.4% after 12 hours in a pH 6.8 buffer. These results prove the suitability of the formulation for an extended release profile.

Comparative Example 108

40.2 g of Phosal 50 PG, 4.7 g of polysorbate 80, 2.3 g of purified water, 2.3 g of Ethanol, anhydrous, 2.7 g of colloidal anhydrous silica, and 7.8 g of pseudoephedrine HCl were mixed to obtain a yellow gel that was homogenous, soft, flowable, pourable, and almost clear.

Comparative Example 109

38.9 g of Phosal 50 PG, 4.7 g of polysorbate 80, 2.3 g of purified water, 2.3 g of Ethanol, anhydrous, 4.0 g of colloidal anhydrous silica, and 7.8 g of pseudoephedrine HCl were mixed to obtain a yellow gel that was homogenous, soft, flowable, pourable, and almost clear.

Comparative Example 110

37.6 g of Phosal 50 PG, 12.7 g of caprylocaproyl macrogol-8 glycerides, 2.7 g of purified water, 2.7 g of xanthan gum, and 7.8 g of pseudoephedrine HCl were mixed to obtain a yellow gel that was homogenous, soft, flowable, pourable, and was turbid.

Comparative Example 111

37.6 g of Phosal 50 PG, 12.7 g of caprylocaproyl macrogol-8 glycerides, 2.7 g of purified water, 2.7 g of xanthan gum, and 7.8 g of pseudoephedrine HCl were mixed to obtain a yellow gel that was homogenous, soft, flowable, pourable, and turbid.

Comparative Example 112

37.6 g of Phosal 50 PG, 12.7 g of caprylocaproyl macrogol-8 glycerides, 2.7 g of purified water, 2.7 g of xanthan gum, and 7.8 g of pseudoephedrine HCl were mixed to obtain a yellow gel that was homogenous, soft, flowable, pourable, and turbid.

Comparative Example 113

36.9 g of Phosal 50 PG, 12.7 g of caprylocaproyl macrogol-8 glycerides, 3.3 g of purified water, 2.7 g of xanthan gum, and 7.8 g of pseudoephedrine HCl were mixed to obtain a yellow gel that was homogenous, soft, flowable, pourable, and turbid.

Comparative Example 114

36.4 g of Phosal 50 PG, 12.7 g of caprylocaproyl macrogol-8 glycerides, 3.8 g of purified water, 2.7 g of xanthan gum, and 7.8 g of pseudoephedrine HCl were mixed to obtain a yellow gel that was homogenous, soft, flowable, pourable, and turbid.

Comparative Example 115

36.4 g of Phosal 50 PG, 12.7 g of caprylocaproyl macrogol-8 glycerides, 3.8 g of purified water, 2.7 g of xanthan gum, and 7.8 g of pseudoephedrine HCl were mixed to obtain a yellow gel that was homogenous, soft, flowable, pourable, and turbid.

Working Example 116

35.8 g of Phosal 50 PG, 12.7 g of caprylocaproyl macrogol-8 glycerides, 4.4 g of purified water, 2.7 g of xanthan gum, and 7.8 g of pseudoephedrine HCl were mixed to obtain a yellow gel that was homogenous, soft, flowable, pourable, and turbid. After treatment with hot water, 3.8% pseudoephedrine HCl was detected in the mixture drawn into a syringe. After a 12 hour dissolution treatment (2 hours in 0.1N HCl, 2 hours in a pH 4.6 buffer, and 8 hours in a pH 6.8 buffer) the following percentages of the active substance was detected in the dissolution media: 35.1% in 0.1 N HCl after 120 min, and 54.2% in a pH 4.6 buffer after 4 hours. 95.5% of the pseudoephedrine HCl was released after 12 hours in a pH 6.8 buffer from 950 mg of fill.

Working Example 117

35.8 g of Phosal 50 PG, 12.7 g of caprylocaproyl macrogol-8 glycerides, 4.4 g of purified water, 2.7 g of xanthan gum, and 7.8 g of pseudoephedrine HCl were mixed to obtain a yellow gel that was homogenous, soft, flowable, pourable, and turbid. After a treatment with hot water, 4.4% pseudoephedrine HCl was detected in the mixture drawn into a syringe. The dissolution profile of the active substance from lab filled capsules was tested over 12 hours (2 hours in 0.1 N HCl, 2 hours in a pH 4.6 buffer and 8 hours in a pH 6.8 buffer). 47.4% of pseudoephedrine HCl was released after 2 hours in 0.1N HCl from lab filled softgels containing 116.48 mg pseudoephedrine HCl in 950 mg of fill suspension. After a further 2 hours in a pH 4.6 buffer 70.9% of the active substance was detected. 95.4% of oxycodone HCl was calculated to be released after 12 hours in a pH 6.8 buffer. These data demonstrate the suitability of formulations of Examples 116 and 117 to obtain a 12 hour extended release profile.

Examples 118 to 126: Macrogol/Labrasol Pseudoephedrine Formulations

Based on the immediate release xanthan gum formulation A the dosage level of xanthan gum was increased to 20 mg (2.1%) in the composition of Example 123, and 40 mg (7%) in the composition of Example 126.

Additionally two formulations (Example Nos. 118 and 119) with 85.00 mg (9.4%) xanthan gum without glycerol and water in the fill were tested for syringeability and dissolution in 0.1 N HCl over 120 and 300 minutes. The dissolution profiles over 120 min in 0.1 N HCl or 300 min in 0.1 N HCl, buffer pH 4.6 and 6.8 show, that by increasing the xanthan gum or colloidal anhydrous silica concentration the release profile was not extended. The syringeability profile appeared to be compliant (up to 12.1%).

Working Example 118

54.4 g of macrogol 600, 8.8 g of caprylocaproyl macrogol-8 glycerides, 2.4 g of anhydrous glycerol, 0.6 g of purified water, 2.5 g of colloidal anhydrous silica, 0.3 g of xanthan gum, and 5.8 g of pseudoephedrine HCl were mixed to obtain an off-white suspension that was pourable, flowable, spatters on boiling, with little foam, and formed a gel. It could hardly be drawn up into the syringe. 15.2% of pseudoephedrine HCl was detected. 100% of pseudoephedrine HCl was released within 30 minutes in 0.1 N HCl from capsules containing 116.48 mg pseudoephedrine HCl in a 940 mg of fill suspension.

Working Example 119

34.1 g of macrogol 400, 11.3 g of caprylocaproyl macrogol-8 glycerides, 5.7 g of xanthan gum, 1.1 g of colloidal anhydrous silica, and 7.8 g of pseudoephedrine HCl were mixed to obtain an off-white suspension that was pourable, thin, sedimented, that spatters on boiling, forming little foam, but formed a strong gel. This gel could not be drawn up into a syringe; no pseudoephedrine HCl was detected in the syringe after boiling of 940 mg suspension with 5 ml water. 71.2% of pseudoephedrine HCl was released within 30 minutes in 0.1 N HCl from lab filled capsules containing 116.48 mg pseudoephedrine HCl in 940 mg of fill suspension.

Working Example 120

34.1 g of macrogol 400, 11.3 g of macrogolglycerolhydroxystearate 40, 5.7 g of xanthan gum, 1.1 g of colloidal anhydrous silica, and 7.8 g of pseudoephedrine HCl were mixed to obtain an off-white suspension that was pourable, flowable, that spatters on boiling, forming little foam, but a gel formed. It could hardly be drawn up into the syringe; 0.7% of pseudoephedrine HCl was detected in the syringe after boiling of 940 mg of suspension with 5 mL of water. 84.9% of pseudoephedrine HCl was released within 30 minutes in 0.1 N HCl from lab filled capsules containing 116.48 mg pseudoephedrine HCl in 900 mg of fill suspension.

Working Example 121

54.5 g of macrogol 600, 8.8 g of caprylocaproyl macrogol-8 glycerides, 2.4 g of anhydrous glycerol, 0.6 g of purified water, 2.5 g of colloidal anhydrous silica, 0.2 g of xanthan gum, 5.8 g of pseudoephedrine HCl were mixed to obtain an off-white suspension that was pourable, thin, sedimented, that spatters on boiling, forming little foam, but formed a gel. It could not be drawn up into the syringe.

Working Example 122

54.6 g of macrogol 600, 8.8 g of caprylocaproyl macrogol-8 glycerides, 2.4 g of anhydrous glycerol, 0.6 g of purified water, 2.5 g of colloidal anhydrous silica, 0.2 g of xanthan gum, 5.8 g of pseudoephedrine HCl were mixed to obtain an off-white suspension that was pourable, flowable, that spatters on boiling, forming little foam, but formed a gel. It could not be drawn up into the syringe.

Working Example 123

52.9 g of macrogol 600, 8.8 g of caprylocaproyl macrogol-8 glycerides, 2.4 g of anhydrous glycerol, 0.6 g of purified water, 2.5 g of colloidal anhydrous silica, 1.0 g of xanthan gum, 5.8 g of pseudoephedrine HCl were mixed to obtain an off-white suspension that was pourable, flowable, spatters on boiling, forming little foam, but formed a gel. It could hardly be drawn up into the syringe.

Working Example 124

51.4 g of macrogol 600, 8.3 g of caprylocaproyl macrogol-8 glycerides, 2.4 g of anhydrous glycerol, 0.6 g of purified water, 4.5 g of colloidal anhydrous silica, 0.3 g of xanthan gum, 5.8 g of pseudoephedrine HCl were mixed to obtain an off-white suspension that was pourable, flowable, spatters on boiling, forming little foam, but formed a gel. It could hardly be drawn up into the syringe.

Comparative Example 125

27.1 g of macrogol 600, 27.0 g of Kollisolv P 124 (Lutrol F44), 8.8 g of caprylocaproyl macrogol-8 glycerides, 2.4 g of anhydrous glycerol, 0.6 g of purified water, 2.5 g of colloidal anhydrous silica, 4.0 g of xanthan gum, 5.8 g of pseudoephedrine HCl were mixed to obtain an off-white suspension that was pourable and flowable.

Working Example 126

79.8 g of macrogol 600, 25.5 g of caprylocaproyl macrogol-8 glycerides, and 7.8 g of anhydrous glycerol, 10.8 g of purified water, 8.3 g of colloidal anhydrous silica, 6.7 g of xanthan gum (Xanthural 180), 19.4 g of pseudoephedrine HCl were mixed to obtain an off-white suspension that was pourable, flowable, and exhibits sedimentation. 2.1% of pseudoephedrine HCl was detected in the syringe after boiling of 950 mg of the suspension with 5 ml water. 81.2% of the pseudoephedrine HCl was released within 30 minutes in 0.1 N HCl from lab filled capsules containing 116.48 mg pseudoephedrine HCl in 950 mg of fill suspension.

Examples 127-135 Additional Hydrophilic Pseudoephedrine Formulations Working Example 127

45.9 g of macrogol 600, 8.0 g of caprylocaproyl macrogol-8 glycerides, 2.4 g of anhydrous glycerol, 0.6 g of purified water, 3.3 g of colloidal anhydrous silica, 4.0 g of Amberlite IRP64, 5.8 g of pseudoephedrine HCl were mixed to obtain an off-white suspension that was pourable and flowable. 8.0% of pseudoephedrine HCl was detected in the syringe after boiling with 5 mL water. 97% of the pseudoephedrine HCl was released within 30 minutes in 0.1 N HCl from lab filled capsules containing 116.48 mg pseudoephedrine HCl in 940 mg of fill suspension.

Working Example 128

30.6 g of macrogol 600, 10.7 g of caprylocaproyl macrogol-8 glycerides, 3.1 g of anhydrous glycerol, 0.8 g of purified water, 4.3 g of colloidal anhydrous silica, 5.3 g of Amberlite IRP69, and 7.8 g of pseudoephedrine HCl were mixed to obtain a brownish suspension that was pourable, flowable, and exhibited sedimentation. 5.5% of pseudoephedrine HCl was detected in the syringe after boiling with 5 ml water. 91.5% of pseudoephedrine HCl was released within 30 minutes in 0.1 N HCl from lab filled capsules containing 116.48 mg pseudoephedrine HCl in 940 mg of fill suspension.

Working Example 129

30.6 g of macrogol 600, 10.7 g of caprylocaproyl macrogol-8 glycerides, 3.1 g of anhydrous glycerol, 0.8 g of purified water, 4.3 g of colloidal anhydrous silica, 5.3 g of Duolite AP143/1093, and 7.8 g of pseudoephedrine HCl were mixed to obtain an off-white suspension that was pourable and flowable. 11.0% of pseudoephedrine HCl was detected in the syringe after boiling with 5 mL of water. 95.6% of pseudoephedrine HCl was released within 30 minutes in 0.1 N HCl from lab filled capsules containing 116.48 mg pseudoephedrine HCl in 940 mg of fill suspension.

Comparative Example 130

30.6 g of macrogol 600, 10.7 g of caprylocaproyl macrogol-8 glycerides, 3.1 g of anhydrous glycerol, 0.8 g of purified water, 4.3 g of colloidal anhydrous silica, 5.3 g of Amberlite IRP69, and 7.8 g of pseudoephedrine HCl were mixed to obtain a brownish suspension that was pourable, flowable, and exhibited sedimentation.

Comparative Example 131

30.6 g of macrogol 600, 10.7 g of caprylocaproyl macrogol-8 glycerides, 3.1 g of anhydrous glycerol, 0.8 g of purified water, 4.3 g of colloidal anhydrous silica, 5.3 g of Duolite AP143/1093, and 7.8 g of pseudoephedrine HCl were mixed to obtain an off-white suspension that was viscous, pourable, and flowable.

Comparative Example 132

77.8 g of macrogol 600, 28.0 g of caprylocaproyl macrogol-8 glycerides, 9.4 g of anhydrous glycerol, 2.5 g of purified water, 9.0 g of colloidal anhydrous silica, 38.0 g of Amberlite IRP69, and 23.3 g of pseudoephedrine HCl were mixed to obtain a brownish suspension that was viscous, pourable, and flowable.

Comparative Example 133

77.8 g of macrogol 600, 28.0 g of caprylocaproyl macrogol-8 glycerides, 9.4 g of anhydrous glycerol, 2.5 g of purified water, 9.0 g of colloidal anhydrous silica, 38.0 g of Duolite AP143/1093, and 23.3 g of pseudoephedrine HCl were mixed to obtain an off-white suspension that was viscous, pourable, and flowable.

Working Example 134

79.8 g of macrogol 600, 26.7 g of caprylocaproyl macrogol-8 glycerides, 7.8 g of anhydrous glycerol, 2.1 g of purified water, 14.2 g of colloidal anhydrous silica, 6.7 g of Amberlite IRP69, and 19.4 g of pseudoephedrine HCl were mixed to obtain a brownish suspension that was viscous, pourable, and flowable. 10.2% of pseudoephedrine HCl was detected in the syringe. 93.4% of the pseudoephedrine HCl was released within 30 minutes in 0.1 N HCl from lab filled capsules containing 116.48 mg pseudoephedrine HCl in 940 mg of fill suspension.

Working Example 135

76.5 g of macrogol 600, 26.7 g of caprylocaproyl macrogol-8 glycerides, 7.8 g of anhydrous glycerol, 2.1 g of purified water, 10.8 g of colloidal anhydrous silica, 13.3 g of Duolite AP143/1093, and 19.4 g of pseudoephedrine HCl were mixed to obtain a brownish suspension that was viscous, pourable, and flowable. The liquid was bubbling under intense increase of viscosity at boiling with water. A thickened stable foam resulted, that could hardly be drawn up into a syringe. 12.1% of pseudoephedrine HCl was detected in the syringe. 96.9% of pseudoephedrine HCl was released within 30 minutes in 0.1 N HCl from lab filled capsules containing 116.48 mg pseudoephedrine HCl in 940 mg of fill suspension.

Working Example 136

76.5 g of macrogol 600, 26.7 g of caprylocaproyl macrogol-8 glycerides, 7.8 g of anhydrous glycerol, 2.1 g of purified water, 10.8 g of colloidal anhydrous silica, 13.3 g of Amberlite IRP88, and 19.4 g of pseudoephedrine HCl were mixed to obtain an off-white suspension that was viscous, pourable, and flowable. Upon boiling with water, an increase of the viscosity and foaming was exhibited. 3.4% of pseudoephedrine HCl was detected in the syringe. 95.2% of pseudoephedrine HCl was released within 30 minutes in 0.1 N HCl from lab filled capsules containing 116.48 mg pseudoephedrine HCl in 940 mg of fill suspension.

Examples 137 to 141: Immediate and Extended Release Oxycodone HCl Formulations

The compositions of Example Nos. 137 (comprising xanthan gum) and 139 (comprising Amberlite IRP64) fulfill the specifications for an immediate release profile. (>80% within 30 minutes). The use of Amberlite IRP69 and Duolite AP 143 in combination with the increased concentration of 8.5% colloidal anhydrous silica leads to a delayed dissolution profile. Within 30 minutes only 52.3% (Amberlite IRP69) or 56.5% (Duolite AP143/1093) are released. After 60 minutes 91.4% (Amberlite IRP69) or 99.7% (Duolite AP143/1093) of oxycodon HCl have be released.

Selected compositions of the Examples below were tested for syringeability and abuse resistance. A maximum of 17.6% of the API was detected in the syringe after boiling of the capsule fill with 5 mL water and filtration through a cigarette filter. The compositions of Example Nos. 140, 139, 137, and 138 showed residual levels of 12.4, 17.6, 2.6 and 4.0%, respectively, of the active pharmaceutical ingredient oxycodone in the residue after boiling and filtering the mixture.

The injectability of oxycodone HCl from all four abuse deterrent formulation types was significantly reduced, especially for the Amberlite IRP69 and Duolite formulations when used in combination with increased amounts of colloidal anhydrous silica, which showed a delayed oxycodone release after 60 minutes. By reducing the concentration of colloidal anhydrous silica to 6.9%, an immediate release dissolution profile with more than 93% of oxycodone HCl released within 30 minutes in 0.1 N HCl was obtained. At least one of the formulations below appears to meet the extended release profile requirements.

Working Example 137

27.3 g of macrogol 600, 18.1 g of caprylocaproyl macrogol-8 glycerides, 2.5 g of anhydrous glycerol, 0.7 g of purified water, 4.0 g of colloidal anhydrous silica, 2.0 g of Amberlite IRP69, and 2.0 g of oxycodone HCl were mixed to obtain a brownish suspension. After boiling of 470 mg of fill with 5 mL water, slight foaming with a viscosity increase was observed. 8.6% of oxycodone HCl was detected in the syringe. 93% of oxycodone HCl was released within 30 minutes in 0.1 N HCl from lab filled capsules containing 20.00 mg oxycodone HCl in 470 mg of fill suspension.

Working Example 138

25.3 g of macrogol 600, 8.5 g of caprylocaproyl macrogol-8 glycerides, 2.5 g of anhydrous glycerol, 0.7 g of purified water, 4.0 g of colloidal anhydrous silica, 4.0 g of Duolite AP143/1093, and 2.0 g of oxycodone HCl were mixed to obtain an off-white suspension. The liquid bubbled with an intense increase of viscosity upon boiling with water. During boiling of the liquid with 5 mL of water, a thickening stable foam resulted which could hardly be drawn up into a syringe. 14.1% of oxycodone HCl was detected in the syringe. 95.6% of the oxycodone HCl was released within 30 minutes in 0.1 N HCl from lab filled capsules containing 20.00 mg oxycodone HCl in 470 mg of fill suspension.

Working Example 139

25.3 g of macrogol 600, 8.5 g of caprylocaproyl macrogol-8 glycerides, 2.5 g of anhydrous glycerol, 0.7 g of purified water, 4.0 g of colloidal anhydrous silica, 4.0 g of Amberlite IRP64, and 2.0 g of oxycodone HCl were mixed to obtain an off-white suspension. Upon heating of 470 mg suspension with 5 mL water, a slight viscosity increase and frothing were observed. 18.9% oxycodone HCl has been detected in the syringe. 91.1% of oxycodone HCl was released within 30 minutes in 0.1 N HCl from lab filled capsules containing 20.00 mg oxycodone HCl in 470 mg of fill suspension.

Working Example 140

29.5 g of macrogol 600, 9.0 g of caprylocaproyl macrogol-8 glycerides, 2.5 g of anhydrous glycerol, 0.7 g of purified water, 4.0 g of colloidal anhydrous silica, 0.3 g of xanthan gum, and 2.0 g of oxycodone HCl were mixed to obtain an off-white suspension. Upon heating 480 mg of the suspension with 5 mL water, an intense increase of viscosity with slight foaming was observed. 12.5% of oxycodone HCl was detected in the syringe. 98.8% of oxycodone HCl was released within 30 minutes in 0.1 N HCl from lab filled capsules containing 20.00 mg oxycodone HCl in 470 mg of fill suspension.

Working Example 141

38.2 g of Phosal 50 PG, 12.7 g of caprylocaproyl macrogol-8 glycerides, 4.4 g of purified water, 2.7 g of xanthan gum, and 5.3 g of oxycodone HCl were mixed to obtain a yellow gel. An instance viscosity increase and stable frothing was observed upon heating of 950 mg of the gel with water. 7.5% of oxycodone HCl was detected in the syringe. The dissolution profile of the active substance from lab filled capsules was tested over 12 hours (2 hours in 0.1 N HCl, 2 hours in a pH 4.6 buffer and 8 hours in a pH 6.8 buffer). 33.6% of oxycodone HCl was released after 2 hours in 0.1N HCl from lab filled softgels containing 80 mg oxycodone HCl in 950 mg of fill suspension. After further 2 hours in a pH 4.6 buffer, 45.2% of the active substance was detected. 88.4% of oxycodone HCl was calculated to have been released after 12 hours in a pH 6.8 buffer. These data show the suitability of the formulation for providing an extended release profile over 12 hours.

Examples 142 to 146: Codeine Phosphate Formulations

Example Nos. 142 to 146 are directed to immediate release and extended release codeine phosphate formulations. One of the formulations below appears to meet the extended release profile requirements.

Working Example 142

26.3 g of macrogol 600, 8.5 g of caprylocaproyl macrogol-8 glycerides, 2.5 g of anhydrous glycerol, 0.7 g of purified water, 4.0 g of colloidal anhydrous silica, 2.0 g of Amberlite IRP69, and 3.0 g of codeine phosphate, hemihydrate were mixed to obtain a brownish suspension. 9.5% codeine phosphate was detected in the syringe after boiling of 470 mg suspension with 5 mL of water. 95.9% of codeine phosphate was released within 30 minutes in 0.1 N HCl from lab filled capsules containing 30.00 mg codeine phosphate, hemihydrate in a 470 mg of fill suspension.

Working Example 143

24.3 g of macrogol 600, 8.5 g of caprylocaproyl macrogol-8 glycerides, 2.5 g of anhydrous glycerol, 0.7 g of purified water, 4.0 g of colloidal anhydrous silica, 4.0 g of Duolite AP143/1093, and 3.0 g of codeine phosphate hemihydrate were mixed to obtain an off-white suspension. 97.3% of codeine phosphate was released within 30 minutes in 0.1 N HCl from lab filled capsules containing 30.00 mg codeine phosphate, hemihydrate in 470 mg of fill suspension.

Working Example 144

24.3 g of macrogol 600, 8.5 g of caprylocaproyl macrogol-8 glycerides, 2.5 g of anhydrous glycerol, 0.7 g of purified water, 4.0 g of colloidal anhydrous silica, 4.0 g of Amberlite IRP64, and 3.0 g of codeine phosphate hemihydrate were mixed to obtain an off white suspension. 11.9% of codeine phosphate was detected in a syringe after boiling of 470 mg suspension with 5 mL water. 99.0% of codeine phosphate was released within 30 minutes in 0.1 N HCl from lab filled capsules containing 30.00 mg codeine phosphate hemihydrate in a 470 mg of fill suspension.

Working Example 145

28.5 g of macrogol 600, 9.0 g of caprylocaproyl macrogol-8 glycerides, 2.5 g of anhydrous glycerol, 0.7 g of purified water, 3.0 g of colloidal anhydrous silica, 0.3 g of xanthan gum, 3.0 g of codeine phosphate hemihydrate were mixed to obtain an off-white suspension. 9.0% of codeine phosphate was detected in a syringe after boiling of 480 mg suspension with 5 mL water. 98.8% of codeine phosphate was released within 30 minutes in 0.1 N HCl from lab filled capsules containing 30.00 mg codeine phosphate hemihydrate in a 480 mg of fill suspension.

Working Example 146

39.6 g of Phosal 50 PG, 12.7 g of caprylocaproyl macrogol-8 glycerides, 4.4 g of purified water, 2.7 g of xanthan gum, 3.3 g of codeine phosphate, hemihydrate were mixed to obtain a yellow gel. 3.8% of codeine phosphate was detected in a syringe after boiling with 5 mL water. The dissolution profile of the active substance from lab filled capsules was tested over 12 hours (2 hours in 0.1 N HCl, 2 hours in a pH 4.6 buffer and 8 hours in a pH 6.8 buffer). 25.1% of codeine phosphate, hemihydrate was released after 2 hours in 0.1 N HCl from lab filled softgels containing 50 mg codeine phosphate hemihydrate in 950 mg of fill suspension. After further 2 hours in a pH 4.6 buffer, 44.7% of the active substance was detected. 86.5% of codeine phosphate hemihydrate was calculated to be released within 12 hours in a pH 6.8 buffer. This example demonstrates the suitability of the formulation for providing an extended release profile over 12 hours.

Examples 147 to 157: Immediate and Extended Release Tilidine HCl Formulations

Example Nos. 147 to 157 are directed to immediate release and extended release Tilidine HCl formulations. One of the formulations below appears to meet the extended release profile requirements.

Working Example 147

32.8 g of macrogol 600, 11.3 g of caprylocaproyl macrogol-8 glycerides, 3.1 g of anhydrous glycerol, 0.8 g of purified water, 5.0 g of colloidal anhydrous silica, 2.7 g of Amberlite IRP69, and 6.9 g of tilidine hydrochloride hemihydrate were mixed to obtain a brownish suspension that was viscous, pourable and flowable. Boiling of 940 mg of this suspension with 5 mL water yielded a mixture that bubbled slightly, and exhibited a viscosity increase. 8.9% of tilidine HCl was detected in the syringe. 96.9% tilidine HCl was released from lab filled softgels containing 100 mg of tilidine HCl in a 940 mg of fill suspension within 30 minutes in 0.1 N HCl.

Working Example 148

31.5 g of macrogol 600, 10.7 g of caprylocaproyl macrogol-8 glycerides, 3.1 g of anhydrous glycerol, 0.8 g of purified water, 4.3 g of colloidal anhydrous silica, 5.3 g of Duolite AP143/1093, 6.9 g of tilidine hydrochloride hemihydrate were mixed to obtain a brownish suspension that was viscous, pourable and flowable. Boiling of 940 mg of this suspension with 5 mL water yielded a mixture that bubbled and exhibited a high viscosity increase. A thick, stable foam resulted, which could hardly be drawn up into a syringe. 6.5% of tilidine HCl was detected in the syringe. 100.3% was detected as released from lab filled softgels containing 100 mg tilidine hydrochloride hemihydrate in 940 mg of fill suspension within 30 minutes in 0.1 N HCl.

Working Example 149

15.8 g of macrogol 600, 5.3 g of caprylocaproyl macrogol-8 glycerides, 1.6 g of anhydrous glycerol, 0.4 g of purified water, 2.2 g of colloidal anhydrous silica, 2.7 g of Amberlite IRP64, 3.4 g of tilidine hydrochloride hemihydrate were mixed to obtain an off-white suspension. Boiling of 470 mg of this suspension with 5 mL water yielded a mixture that bubbled slightly, and exhibited a viscosity increase. 2.5% of tilidine HCl was detected in a syringe after boiling with a reduced amount of 2.5 mL of water. 15.2% of tilidine HCl was detected in a syringe after boiling with 5 mL of water. 97.0% of tilidine HCl was released from lab filled softgels containing 50 mg tilidine HCl in a 470 mg of fill suspension within 30 minutes in 0.1 N HCl.

Working Example 150

31.5 g of macrogol 600, 10.7 g of caprylocaproyl macrogol-8 glycerides, 3.1 g of anhydrous glycerol, 0.8 g of purified water, 4.3 g of colloidal anhydrous silica, 5.3 g of Amberlite IRP64, 6.9 g of tilidine hydrochloride hemihydrate were mixed to obtain an off-white suspension. Boiling this suspension with 5 mL water yielded a mixture that bubbled slightly, and exhibited a viscosity increase. 6.6% of tilidine HCl was detected in a syringe after boiling with 5 mL of water. 99.9% of tilidine HCl was released from lab filled softgels containing 100 mg tilidine HCl in a 940 mg of fill suspension within 30 minutes in 0.1 N HCl.

Working Example 151

7.9 g of macrogol 600, 2.7 g of caprylocaproyl macrogol-8 glycerides, 0.8 g of anhydrous glycerol, 0.8 g of purified water, 1.1 g of colloidal anhydrous silica, 1.3 g of Amberlite IRP64, 1.7 g of tilidine hydrochloride hemihydrate were mixed to obtain an off-white suspension. Boiling of 180 mg of this suspension (corresponding to 20 mg of tilidine HCl) with water yielded a mixture that bubbled slightly, and exhibited a viscosity increase. 13.0% of tilidine HCl was detected in a syringe after boiling with a reduced amount of 2.5 mL of water. 41.4% of tilidine HCl was detected in a syringe after boiling with 5 mL of water. This behavior shows that amounts above a minimum total concentration of the ion exchange resin could be used to achieve abuse resistant properties of the fill.

Working Example 152

16.9 g of macrogol 600, 5.7 g of caprylocaproyl macrogol-8 glycerides, 1.7 g of anhydrous glycerol, 0.4 g of purified water, 2.7 g of colloidal anhydrous silica, 2.7 g of Amberlite IRP64, 1.4 g of tilidine hydrochloride hemihydrate were mixed to obtain an off-white suspension. Boiling of 470 mg of this suspension with 5 mL of water yielded a mixture that bubbled slightly, and exhibited a viscosity increase. 8.9% of tilidine HCl was detected in a syringe. 99.3% of tilidine HCl was released from lab filled softgels containing 50 mg tilidine HCl in a 470 mg of fill suspension within 30 minutes in 0.1 N HCl.

Working Example 153

37.2 g of macrogol 600, 11.7 g of caprylocaproyl macrogol-8 glycerides, 3.1 g of anhydrous glycerol, 0.8 g of purified water, 3.3 g of colloidal anhydrous silica, 0.3 g of xanthan gum, 6.9 g of tilidine hydrochloride hemihydrate were mixed to obtain an off-white suspension. Heating of 940 mg of the fill suspension with 5 mL of water showed an intense increase of viscosity with slight foaming. 3.9% of tilidine HCl was detected in a syringe. 96.9% of the tilidine hydrochloride hemihydrate was released from lab filled softgels containing 100 mg tilidine hydrochloride hemihydrate in 950 mg of fill suspension within 30 minutes in 0.1 N HCl.

Working Example 154

18.6 g of macrogol 600, 5.8 g of caprylocaproyl macrogol-8 glycerides, 2.4 g of anhydrous glycerol, 0.4 g of purified water, 1.6 g of colloidal anhydrous silica, 0.2 g of xanthan gum, 3.4 g of tilidine hydrochloride hemihydrate were mixed to obtain an off-white suspension. Heating with water results in an intense increase of viscosity with slight foaming. 0.4% of tilidine hydrochloride hemihydrate was detected in a syringe after boiling of 470 mg of fill suspension (corresponding to 50 mg tilidine HCl) with a reduced amount of 2.5 mL water. 11.0% of tilidine hydrochloride hemihydrate was detected in the syringe after boiling of 470 mg of fill suspension (corresponding to 50 mg tilidine HCl) with 5 mL water. 96.2% tilidine hydrochloride hemihydrate was released from lab filled softgels containing 50 mg tilidine hydrochloride hemihydrate in 470 mg of fill suspension within 30 minutes in 0.1 N HCl.

Working Example 155

7.4 g of macrogol 600, 2.3 g of caprylocaproyl macrogol-8 glycerides, 0.6 g of anhydrous glycerol, 0.2 g of purified water, 0.7 g of colloidal anhydrous silica, 0.1 g of xanthan gum, 1.4 g of tilidine hydrochloride hemihydrate were mixed to obtain an off-white suspension. Upon heating with water, an intense increase of viscosity with slight foaming was observed. 5.8% of tilidine HCl was detected in a syringe after boiling of 190 mg of fill suspension (corresponding to 20 mg tilidine HCl) with a reduced amount of 2.5 mL water. 38.2% of tilidine HCl was detected in the syringe after boiling of 190 mg of fill suspension (corresponding to 20 mg tilidine HCl) with 5 mL water. These results demonstrate that use of an amount of xanthan gum above a minimum total concentration of xanthan gum provided abuse resistant properties to the capsule fill.

Working Example 156

19.7 g of macrogol 600, 6.0 g of caprylocaproyl macrogol-8 glycerides, 1.7 g of anhydrous glycerol, 0.4 g of purified water, 2.0 g of colloidal anhydrous silica, 0.2 g of xanthan gum, 1.4 g of tilidine hydrochloride hemihydrate were mixed to obtain an off-white suspension. Upon heating of 470 mg of fill suspension with 5 mL water an intense increase of viscosity with slight foaming was observed. 9.6% tilidine HCl was detected in a syringe. 100.5% of tilidine hydrochloride hemihydrate was calculated to be released from lab filled softgels containing 50 mg tilidine hydrochloride hemihydrate in 470 mg of fill suspension within 30 minutes in 0.1 N HCl.

Working Example 157

36.0 g of Phosal 50 PG, 12.7 g of caprylocaproyl macrogol-8 glycerides, 4.4 g of purified water, 2.7 g of xanthan gum and 6.9 g of tilidine hydrochloride hemihydrate were mixed to obtain a yellow gel. An intense viscosity increase and stable frothing was observed at heating of 940 mg of the yellow gel with water. 2.9% of tilidine hydrochloride hemihydrate was detected in a syringe. The dissolution profile of the active substance from lab filled capsules was tested over 12 hours (2 hours in 0.1 N HCl, 2 hours in a pH 4.6 buffer and 8 hours in a pH 6.8 buffer). 42.7% of tilidine hydrochloride hemihydrate was released after 2 hours in 0.1N HCl from lab filled softgels containing 100 mg tilidine HCl in 940 mg of fill suspension. After further 2 hours in a pH 4.6 buffer, 57.1% of the active substance was detected. 85.7% of tilidine hydrochloride was calculated to be released after 12 hours in a pH 6.8 buffer. These data show the suitability of the formulation for providing an extended release profile over 12 hours.

The invention claimed is:

1. An immediate release parenteral abuse resistant capsule comprising a shell encapsulating a parenteral abuse resistant liquid comprising:
   (a) an abuse-susceptible active pharmaceutical ingredient selected from the group consisting of opiates, opioids, tranquillizers, stimulants and narcotics;
   (b) an ion exchange resin selected from the group consisting of polyacrilex resin, sodium polystyrene sulfonate, potassium polyacrilin, and colestyramine resin;
   (c) 5.0 to 45.6 wt. % of a surfactant selected from polyoxyethylene (20) sorbitan monolaurate, -polyoxyethylene (20) sorbitan monooleate, macrogolglycerol hydroxystearate, macrogolglycerol ricinoleate, glycerolmonooleate 40, macrogolglycerol linoleate, linoleoyl macrogol-6 glycerides, propylene glycol monolaurate FCC, polyglyceryl-6-dioleate, polyglycerol-3-dioleate, propylene glycol monocaprylate, sorbitanmonolaurate, sorbitanmonooleate, Vitamin E-polyethylenglycol-succinate, caprylocaproyl macrogol-8 glycerides, macrogol-32-glycerol-laurate, glycerylmonocaprate/caprylate, and a phosphatidylcholine concentrate; and
   (d) 40 wt. % to 60 wt. % of a carrier comprising a hydrophilic carrier selected from macrogol 400, macrogol 600, macrogol 1500, propylene glycol, glycerol and water, to dissolve or suspend the active pharmaceutical ingredient; wherein the parenteral abuse resistant liquid does not comprise a hydrogelling agent; the capsule releases more than 80% of the active pharmaceutical ingredient within the gastrointestinal tract within 30 minutes of administration, all weight percentages being based on a total weight of the parenteral abuse resistant liquid.

2. The immediate release parenteral abuse resistant capsule of claim 1, wherein a mixture of about 250 to about 1000 milligrams of the abuse resistant liquid with 5 milliliters of water at the mixture's boiling point forms a viscous phase, wherein about 33% or less of the pharmaceutically active ingredient can be recovered from the viscous phase drawn up into a 25 millimeter needle having an inner diameter of 0.60 millimeters.

3. The immediate release parenteral abuse resistant capsule of claim 1, wherein the surfactant is selected from sorbitanmonolaurate, sorbitanmonooleate, Vitamin E-polyethylenglycol-succinate, and caprylocaproyl macrogol-8 glycerides.

4. The immediate release parenteral abuse resistant capsule of claim 1, further comprising
(e) a stabilizer.

5. The immediate release parenteral abuse resistant capsule of claim 4, wherein the stabilizer is selected from the group consisting of colloidal anhydrous silica, hard fat and a glycerol ester of long chain fatty acid.

6. The immediate release parenteral abuse resistant capsule of claim 5, wherein the stabilizer is colloidal anhydrous silica.

7. The immediate release parenteral abuse resistant capsule of claim 1, wherein the hydrophilic carrier is macrogol 600 or water.

8. The immediate release parenteral abuse resistant capsule of claim 4, wherein the stabilizer is hard fat or a glycerol ester of long chain fatty acids.

9. The immediate release parenteral abuse resistant capsule of claim 4 comprising
(i) 40 to 60 wt % macrogol 600;
(ii) 15 to 25 wt % caprylocaproylmacrogol-8 glycerides;
(iii) 3 to 10 wt % colloidal anhydrous silica;
(iv) 3 to 6 wt % glycerol;
(v) 0.5 to 10 wt % water; and
(vi) 2 to 20 wt % ion exchange resin
wherein the weight percentages are calculated with respect to the weight of the parenteral abuse resistant liquid.

10. The immediate release parenteral abuse resistant capsule of claim 1, wherein the active pharmaceutical ingredient is selected from the group consisting of N-{1-[2-(4-ethyl-5-oxo-2-tetrazolin-1-yl)ethyl]-4-methoxymethyl-4-piperidyl}propionanilide; alfentanil; 5,5-diallylbarbituric acid; allobarbital; allylprodine; alphaprodine; 8-chloro-1-methyl-6-phenyl-4H-[1,2,4]triazolo[4,3-a][1,4]-benzodiazepine; alprazolam; 2-diethylaminopropiophenone; amfepramone, (±)-amethylphenethylamine; amphetamine; 2-(α-methylphenethylamino)-2-phenylacetonitrile; amphetaminil; 5-ethyl-5-isopentylbarbituric acid; amobarbital; anileridine; apocodeine; 5,5-diethylbarbituric acid; barbital; benzylmorphine; bezitramide; 7-bromo-5-(2-pyridyl)-1H-1,4-benzodiazepine-2(3H)-one; bromazepam; 2-bromo-4-(2-chlorophenyl)-9-methyl-1-6H-thieno[3,2-f][1,2,4]triazolo[4,3-a][1,4]diazepine; brotizolam, 17-cyclopropylmethyl-4,5a-epoxy-7a[(S)-1-hydroxy-1,2,2-trimethyl-propyl]-6-methoxy-6,14-endo-ethanomorphinan-3-ol; buprenorphine; 5-butyl-5-ethylbarbituric acid; butobarbital; butorphanol; (7-chloro-1,3-dihydro-1-methyl-2-oxo-5-phenyl-2H-1,4-benzodiazepin-3-yl) dimethylcarbamate; camazepam; (1S,2S)-2-amino-1-phenyl-1-propanol; cathine; d-norpseudoephedrine; 7-chloro-N-methyl-5-phenyl-3H-1,4-benzodiazepin-2-ylamine 4-oxide; chlordiazepoxide, 7-chloro-1-methyl-5-phenyl-1H-1,5-benzodi-azepine-2,4(3H,5H)-dione; clobazam, 5-(2-chlorophenyl)-7-nitro-1H-1,4-benz-odiazepin-2(3H)-one; clonazepam; clonitazene; 7-chloro-2,3-dihydro-2-oxo-5-phenyl-1H-1,4-benzodiazepine-3-carboxylic acid; clorazepate; 5-(2-chlorophenyl)-7-ethyl-1-methyl-1H-thieno[2,3-e][1,4]diazepin-2(3H)-one; clotiazepam; 10-chloro-11b-(2-chlorophenyl)-2,3,7,11b-tetrahydrooxazol-o[3,2-d][1,4]benzodiazepin-6(5H)-one; cloxazolam; (–)-methyl-[3β-benzoyloxy-2β(1αH,5αH)-tropane carboxylate]; cocaine; (5α,6α)-7,8-didehydro-4,5-epoxy-3-methoxy-17-methyl-morphinan-6-ol; 4,5α-epoxy-3-methoxy-17-methyl-7-morphinen-6α-ol; codeine; 5-(1-cyclohexenyl)-5-ethyl barbituric acid; cyclobarbital; cyclorphan; cyprenorphine; 7-chloro-5-(2-chloropheny-1)-1H-1,4-benzodiazepin-2(3H)-one; delorazepam; desomorphine; dextromoramide; (+)-(1-benzyl-3-dimethylamino-2-methyl-1-phenylpropyl)propionate; dextropropoxyphene; dezocine; diampromide; diamorphone; 7-chloro-1-methyl-5-phenyl-1H-1,4-benzodiazepin-2(3H)-on; diazepam; 4,5α-epoxy-3-methoxy-17-methyl-6α-morphinanol; dihydrocodeine; 4,5α-epoxy-17-methyl-3,6a-morphinandiol; dihydromorphine; dimenoxadol; dimephetamol; dimethylthiambutene; dioxaphetyl butyrate; dipipanone; (6aR,10aR)-6,6,9-trimethyl-3-pentyl-6a,7,8,10a-tetrahydro-6H-benzo[c]chromen-1-ol; dronabinol; eptazocine; 8-chloro-6-phenyl-4H-[1,2,4]-triazolo[4,3-(a)][1,4] benzodiazepine; estazolam; ethoheptazine; ethylmethylthiambutene; ethyl[7-chloro-5-(2-fluorophenyl)-2,3-dihydro-2-oxo-1H-1,4-benzodiazepine-3-carboxylate]; ethyl loflazepate; 4,5α-epoxy-3-ethoxy-17-methyl-7-morphinen-6α-ol; ethylmorphine; etonitazene; 4,5α-epoxy-7α-(1-hydroxy-1-methylbutyl)-6-methoxy-17-methyl-6,14-endo-etheno-morphinan-3-ol; etorphine; N-ethyl-3-phenyl-8,9,10-trinorbornan-2-ylamine; fencamfamine; 7-[2-(α-methylphenethylamino)ethyl]-theophylline; fenethylline; 3-(α-methylphenethylamino)propionitrile; fenproporex; N-(1-phenethyl-4-piperidyl)propionanilide; fentanyl; 7-chloro-5-(2-fluorophenyl)-1-methyl-1H-1,4-benzodiazepin-2(3H)-one; fludiazepam; 5-(2-fluorophenyl)-1-methyl-7-nitro-1H-1,4-benzodiazepin-2(3H)-one; flunitrazepam; 7-chloro-1-(2-diethylaminoethyl)-5-(2-fluorophenyl)-1H-1,4-benzodiazepin-2(3H)-one; flurazepam; 7-chloro-5-phenyl-1-(2,2,2-trifluoroethyl)-1H-1,4-benzodiazepin-2(3H)-one; halazepam; 10-bromo-11b-(2-fluorophenyl)-2,3,7,11b-tetrahydro[1,3]oxazolyl[3,2-d][1,4]benzodiazepin-6(5H)-one; haloxazolam; heroin; 4,5α-epoxy-3-methoxy-17-methyl-6-morphinanone; hydrocodone; 4,5α-epoxy-3-hydroxy-17-methyl-6-morphinanone; hydromorphone; hydroxypethidine; isomethadone; hydroxymethylmorphinan; 11-chloro-8,12b-dihydro-2,8-dimethyl-12b-phenyl-4H-[1,3]oxazino[3,2d][1,4]benzodiazepine-4,7(6H)-dione; ketazolam; 1-[4-(3-hydroxyphenyl)-1-methyl-4-piperidyl]-1-propanone; ketobemidone; (3S,6S)-6-dimethylamino-4,4-diphenylheptan-3-yl acetate; levacetylmethadol; LAAM; (–)-6-dimethylamino-4,4-diphenol-3-heptanone; levomethadone; (–)-17-methyl-3-morphinanol; levorphanol; levophenacylmorphane; lofentanil; 6-(2-chlorophenyl)-2-(4-methyl-1-piperazinylmethylene)-8-nitro-2H-imidazo[1,2-a][1,4]-benzodiazepin-1(4H)-one; loprazolam; 7-chloro-5-(2-chlorophenyl)-3-hydroxy-1H-1,4-benzodiazepin-2(3H)-one; lorazepam; 7-chloro-5-(2-chlorophenyl)-3-hydroxy-1-methyl-1H-1,4-benzodiazepin-2(3H)-one; lormetazepam; 5-(4-chlorophenyl)-2,5-dihydro-3H-imidazo[2,1a]isoindol-5-ol; mazindol; 7-chloro-2,3-dihydro-1-methyl-5-phenyl-1H-1,4-benzodiazepine; medazepam; N-(3-chloropropyl)-α-methylphenethylamine; mefenorex; meperidine; 2-methyl-2-propyltrimethylene dicarbamate; meprobamate; meptazinol; metazocine; methylmorphine; N,α-dimethylphenethylamine; methamphetamine; (±)-6-dimethylamino-4,4-diphenol-3-heptanone; methadone; 2-methyl-3-o-tolyl-4(3H)-quinazolinone; methaqualone; methyl[2-phenyl-2-(piperidyl)acetate]; methylphenidate; 5-ethyl-1-methyl-5-phenylbarbituric acid; methylphenobarbital; 3,3-diethyl-5-methyl-2,4-piperidinedione; methyprylon; metopon; 8-chloro-6-(2-fluorophenyl)-1-methyl-4H-imidazo[1,5-a][1,4]benzodiazepine; midazolam; 2-(benzhydrylsulfinyl)acetamide; modafinil; (5a,6a)-7,8-didehydro-4,5-epoxy-17-methyl-7-methylmorphinan-3,6-diol; morphine; myrophine; (±)-trans-3-(1,1-dimethylheptyl)-7,8,10,10a-tetrahydro-1-hydroxy-6,6-dimethyl-6H-dibenzo-[b,d]pyran-9(6αH)one; nabilone; nalbuphene;

nalorphine; narceine; nicomorphine; 1-methyl-7-nitro-5-phenyl-1H-1,4-benzodiazepin-2(3H)-one; nimetazepam; 7-nitro-5-phenyl-1H-1,4-benzodiazepin-2(3H)-one; nitrazepam; 7-chloro-5-phenyl-1H-1,4-benzodiazepin-2(-3H)-one; nordazepam; norlevorphanol; 6-dimethylamino-4,4-diphenyl-3-hexanone; normethadone; normorphine; norpipanone; opium; 7-chloro-3-hydroxy-5-phenyl-1H-1,4-benzodiazepin-2(3H)-one; oxazepam; (cis-/trans-)-10-chloro-2,3,7,11b-tetrahydro-2-methyl-11b-phenyloxazolo[3,2-d][1,4]benzodiazepin-6-(5H)-one; oxazolam; 4,5α-epoxy-14-hydroxy-3-methoxy-17-methyl-6-morphinanone; oxycodone; oxymorphone; papaveretum; 2-imino-5-phenyl-4-oxazolidinone; pernoline; 1,2,3,4,5,6-hexahydro-6,11-dimethyl-3-(3-methyl-2-butenyl)-2,6-methano-3-benzazocin-8-ol; pentazocine; 5-ethyl-5-(1-methylbutyl)-barbituric acid; pentobarbital; ethyl-(1-methyl-4-phenyl-4-piperidinecarboxylate); pethidine; phenadoxone; phenomorphane; phenazocine; phenoperidine; piminodine; pholcodeine; 3-methyl-2-phenylmorpholine; phenmetrazine; 5-ethyl-5-phenylbarbituric acid; phenobarbital; α,α-dimethylphenethylamine; phentermine; (R)-3-[-1-hydroxy-2-(methylamino)ethyl]phenol; phenylephrine, 7-chloro-5-phenyl-1-(2-propynyl)-1H-1,4-benzodiazepin-2(3H)-one; pinazepam; α-(2-piperidyl)benzhydryl alcohol; pipradrol; 1'-(3-cyano-3,3-diphenylpropyl)[1,4'-bipiperidine]-4'-carboxamide; piritramide; 7-chloro-1-(cyclopropylmethyl)-5-phenyl-1H-1,4-benzodiazepin-2(3H)-one; prazepam; profadol; proheptazine; promedol; properidine; propoxyphene; N-(1-methyl-2-piperidinoethyl)-N-(2-pyridyl)propionamide; methyl{3-[4-methoxycarbonyl-4-(N-phenylpropanamido)piperidino]propanoate}; (S,S)-2-methylamino-1-phenylpropan-1-ol; pseudoephedrine, remifentanil; 5-sec-butyl-5-ethylbarbituric acid; secbutabarbital; 5-allyl-5-(1-methylbutyl)-barbituric acid; secobarbital; N-{4-methoxymethyl-1-[2-(2-thienyl)ethyl]-4-piperidyl}propionanilide; sufentanil; 7-chloro-2-hydroxymethyl-5-phenyl-1H-1,4-benzodiazepin-2(3H)-one; temazepam; 7-chloro-5-(1-cyclohexenyl)-1-methyl-1H-1,4-benzodiazepin-2(3H)-one; tetrazepam; ethyl (2-dimethylamino-1-phenyl-3-cyclohexene-1-carboxylate; tilidine; tramadol; 8-chloro-6-(2-chlorophenyl)-1-methyl-4H-[1,2,4]triazolo[4,3-a][1,4]benzodiazepine; triazolam; 5-(1-methylbutyl)-5-vinylbarbituric acid; vinylbital; (1R*,2R*)-3-(3-dimethylamino-1-ethyl-2-methylpropyl)phenol; (1R,2R,4S)-2-(dimethylamino)methyl-4-(p-fluorobenzyloxy)-1-(m-methoxyphenyl)cyclohexanol; a prodrug thereof; a pharmaceutically acceptable salt thereof; an adduct thereof; and a solvate thereof.

11. The immediate release parenteral abuse resistant capsule of claim 1, wherein the active pharmaceutical ingredient is selected from the group consisting of codeine, tramadol, anileridine, prodine, pethidine, hydrocodone, morphine, oxycodone, methadone, diamorphine, hydromorphone, oxymorphone, 7-hydroxymitragynine, buprenorphine, fentanyl, sufentanil, levorphanol, meperidine, dihydrocodeine, dihydromorphine, morphine, hydromorphone, oxymorphone, tilidine, a prodrug thereof, a pharmaceutically acceptable salt thereof, and a solvate thereof.

12. The immediate release parenteral abuse resistant capsule of claim 1, that is resistant to alcohol dose dumping or is resistant to solvent, acidic or aqueous extraction.

13. The immediate release parenteral abuse resistant capsule of claim 1, wherein the ion exchange resin creates a drug-ion exchange complex that dissociates within 30 minutes of entry into the gastrointestinal tract.

14. The immediate release parenteral abuse resistant capsule of claim 1, wherein the capsule is a soft capsule or a hard gelatin capsule.

15. The immediate release parenteral abuse resistant capsule of claim 1, wherein the parenteral abuse resistant liquid further comprises polyethylene glycol.

* * * * *